(12) United States Patent
Polson et al.

(10) Patent No.: US 12,016,842 B2
(45) Date of Patent: Jun. 25, 2024

(54) METHODS OF USING ANTI-CD79b IMMUNOCONJUGATES

(71) Applicant: Genentech, Inc., South San Francisco, CA (US)

(72) Inventors: Andrew Polson, San Francisco, CA (US); Shang-Fan Yu, Millbrae, CA (US); Yu-Waye Chu, Burlingame, CA (US); Michael Wenger, Los Altos Hills, CA (US); Jamie Harue Hirata, South San Francisco, CA (US); Dan Lu, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 231 days.

(21) Appl. No.: 17/230,861

(22) Filed: Apr. 14, 2021

(65) Prior Publication Data

US 2022/0040153 A1 Feb. 10, 2022

Related U.S. Application Data

(60) Division of application No. 16/358,410, filed on Mar. 19, 2019, now Pat. No. 11,000,510, which is a continuation of application No. 15/440,917, filed on Feb. 23, 2017, now abandoned, which is a continuation of application No. 14/863,125, filed on Sep. 23, 2015, now abandoned.

(60) Provisional application No. 62/136,324, filed on Mar. 20, 2015, provisional application No. 62/076,823, filed on Nov. 7, 2014, provisional application No. 62/054,257, filed on Sep. 23, 2014.

(51) Int. Cl.
| | |
|---|---|
| A61K 39/00 | (2006.01) |
| A61K 31/4184 | (2006.01) |
| A61K 31/454 | (2006.01) |
| A61K 31/553 | (2006.01) |
| A61K 31/635 | (2006.01) |
| A61K 39/395 | (2006.01) |
| A61K 45/06 | (2006.01) |
| A61K 47/68 | (2017.01) |
| C07K 16/28 | (2006.01) |
| C07K 16/30 | (2006.01) |

(52) U.S. Cl.
CPC ........ *A61K 31/4184* (2013.01); *A61K 31/454* (2013.01); *A61K 31/553* (2013.01); *A61K 31/635* (2013.01); *A61K 39/3955* (2013.01); *A61K 39/39558* (2013.01); *A61K 45/06* (2013.01); *A61K 47/6803* (2017.08); *A61K 47/6849* (2017.08); *A61K 47/6867* (2017.08); *A61K 47/6889* (2017.08); *C07K 16/2803* (2013.01); *C07K 16/2887* (2013.01); *C07K 16/3061* (2013.01); *A61K 2039/507* (2013.01); *A61K 2039/54* (2013.01); *A61K 2039/545* (2013.01); *A61K 2300/00* (2013.01); *C07K 2317/24* (2013.01)

(58) Field of Classification Search
CPC .......... A61K 39/39558; A61K 47/6889; A61K 2300/00; C07K 16/2887; C07K 16/3061; A61P 35/00
See application file for complete search history.

(56) References Cited

U.S. PATENT DOCUMENTS

| | | |
|---|---|---|
| 3,445,518 A | 5/1969 | Shavel, Jr. |
| 4,414,205 A | 11/1983 | Pettit |
| 4,753,894 A | 6/1988 | Frankel |
| 4,764,368 A | 8/1988 | Blattler |
| 4,816,444 A | 3/1989 | Pettit |
| 4,816,567 A | 3/1989 | Cabilly |
| 4,879,278 A | 11/1989 | Pettit |
| 4,943,628 A | 7/1990 | Rosen |
| 4,975,278 A | 12/1990 | Senter |
| 4,978,744 A | 12/1990 | Pettit |
| 5,122,368 A | 6/1992 | Greenfield |
| 5,165,923 A | 11/1992 | Thorpe |
| 5,179,774 A | 1/1993 | Massie |
| 5,208,020 A | 5/1993 | Chari |
| 5,286,637 A | 2/1994 | Veronese |
| 5,410,024 A | 4/1995 | Pettit |
| 5,416,064 A | 5/1995 | Chari |
| 5,521,284 A | 5/1996 | Pettit |
| 5,553,097 A | 9/1996 | Dagher |
| 5,554,725 A | 9/1996 | Pettit |
| 5,585,089 A | 12/1996 | Queen et al. |
| 5,599,902 A | 2/1997 | Pettit |
| 5,629,197 A | 5/1997 | Ring |
| 5,635,483 A | 6/1997 | Pettit |

(Continued)

FOREIGN PATENT DOCUMENTS

| | | |
|---|---|---|
| AU | 2004213053 A1 | 9/2004 |
| CA | 2114156 C | 1/2001 |

(Continued)

OTHER PUBLICATIONS

Pascalis et al (The Journal of Immunology (2002) 169, 3076-3084) (Year: 2002).*
Casset et al. (2003) BBRC 307, 198-205, (Year: 2003).*
D'Angelo et al, Frontiers in Immunology vol. 9 p. 1 (2018) (Year: 2018).*
Anonymous (Jul. 2005). "Guidance for Industry: Estimating the Maximum Safe Starting Dose in Initial Clinical Trials for Therapeutics in Adult Healthy Volunteers," Pharmacology and Toxicology, 30 pages.

(Continued)

*Primary Examiner* — Sheela J. Huff
(74) *Attorney, Agent, or Firm* — Morrison & Foerster LLP

(57) ABSTRACT

Provided herein are methods of treating B-cell proliferative disorders in particular Follicular Lymphoma and/or Diffuse Large B-Cell Lymphoma using immunoconjugates comprising anti-CD79b antibodies in combination with additional therapeutic agents.

18 Claims, 4 Drawing Sheets

Specification includes a Sequence Listing.

(56) References Cited

U.S. PATENT DOCUMENTS

| | | |
|---|---|---|
| 5,644,033 A | 7/1997 | Seon |
| 5,654,399 A | 8/1997 | Sakakibara |
| 5,655,033 A | 8/1997 | Inoguchi |
| 5,663,149 A | 9/1997 | Pettit |
| 5,665,860 A | 9/1997 | Pettit |
| 5,708,146 A | 1/1998 | Willner |
| 5,714,586 A | 2/1998 | Kunstmann |
| 5,741,892 A | 4/1998 | Barlozzari |
| 5,767,236 A | 6/1998 | Kim |
| 5,767,237 A | 6/1998 | Sakakibara |
| 5,780,588 A | 7/1998 | Pettit |
| 5,821,337 A | 10/1998 | Carter |
| 5,840,699 A | 11/1998 | Sakakibara |
| 5,869,445 A | 2/1999 | Cheever |
| 5,965,337 A | 10/1999 | Droin |
| 6,004,934 A | 12/1999 | Sakakibara |
| 6,033,876 A | 3/2000 | Lemke |
| 6,034,065 A | 3/2000 | Pettit |
| 6,048,720 A | 4/2000 | Dalborg |
| 6,054,297 A | 4/2000 | Carter |
| 6,054,561 A | 4/2000 | Ring |
| 6,075,181 A | 6/2000 | Kucherlapati |
| 6,124,431 A | 9/2000 | Sakakibara |
| 6,143,721 A | 11/2000 | Janssen |
| 6,150,584 A | 11/2000 | Kucherlapati |
| 6,162,930 A | 12/2000 | Pinney |
| 6,172,213 B1 | 1/2001 | Lowman |
| 6,183,744 B1 | 2/2001 | Goldenberg |
| 6,214,345 B1 | 4/2001 | Firestone |
| 6,239,104 B1 | 5/2001 | Pettit |
| 6,248,564 B1 | 6/2001 | Walter |
| 6,313,276 B1 | 11/2001 | Imura |
| 6,319,688 B1 | 11/2001 | Feild |
| 6,323,315 B1 | 11/2001 | Pettit |
| 6,342,219 B1 | 1/2002 | Thorpe |
| 6,342,221 B1 | 1/2002 | Thorpe |
| 6,399,063 B1 | 6/2002 | Hudziak |
| 6,407,213 B1 | 6/2002 | Carter |
| 6,458,356 B1 | 10/2002 | Arakawa |
| 6,569,834 B1 | 5/2003 | Pettit |
| 6,620,911 B1 | 9/2003 | Pettit |
| 6,639,055 B1 | 10/2003 | Carter |
| 6,884,869 B2 | 4/2005 | Senter |
| 6,913,748 B2 | 7/2005 | Widdison |
| 7,052,873 B2 | 5/2006 | Tsuchiya |
| 7,053,186 B2 | 5/2006 | Afar |
| 7,090,843 B1 | 8/2006 | Francisco |
| 7,091,186 B2 | 8/2006 | Senter |
| 7,097,840 B2 | 8/2006 | Erickson |
| 7,098,305 B2 | 8/2006 | Deghenghi |
| 7,098,308 B2 | 8/2006 | Senter |
| 7,202,346 B2 | 4/2007 | Payne |
| 7,276,372 B2 | 10/2007 | Law |
| 7,288,248 B2 | 10/2007 | Bhaskar |
| 7,303,749 B1 | 12/2007 | Chari |
| 7,312,343 B2 | 12/2007 | Schmid |
| 7,375,078 B2 | 5/2008 | Feng |
| 7,399,469 B2 | 7/2008 | Zhang |
| 7,498,298 B2 | 3/2009 | Doronina |
| 7,521,541 B2 | 4/2009 | Eigenbrot |
| 7,553,816 B2 | 6/2009 | Senter |
| 7,601,354 B2 | 10/2009 | Chari |
| 7,659,241 B2 | 2/2010 | Senter |
| 7,662,387 B2 | 2/2010 | Law |
| 7,662,936 B2 | 2/2010 | Kadkhodayan |
| 7,737,259 B2 | 6/2010 | Chen |
| 7,745,394 B2 | 6/2010 | Doronina |
| 7,750,116 B1 | 7/2010 | Doronina |
| 7,754,681 B2 | 7/2010 | Feng |
| 7,803,915 B2 | 9/2010 | Cairns |
| 7,829,531 B2 | 11/2010 | Senter |
| 7,837,980 B2 | 11/2010 | Alley |
| 7,851,437 B2 | 12/2010 | Senter |
| 7,855,275 B2 | 12/2010 | Eigenbrot |
| 7,892,550 B2 | 2/2011 | Dennis |
| 7,947,839 B2 | 5/2011 | Gazzard |
| 7,964,566 B2 | 6/2011 | Doronina |
| 7,964,567 B2 | 6/2011 | Doronina |
| 7,968,687 B2 | 6/2011 | Mcdonagh |
| 7,989,434 B2 | 8/2011 | Feng |
| 7,994,135 B2 | 8/2011 | Doronina |
| 8,067,544 B2 | 11/2011 | Landes |
| 8,088,378 B2 | 1/2012 | Chen |
| 8,088,387 B2 | 1/2012 | Steeves |
| 8,142,784 B2 | 3/2012 | Ebens, Jr. |
| 8,198,417 B2 | 6/2012 | Steeves |
| 8,263,083 B2 | 9/2012 | Oflazoglu |
| 8,288,352 B2 | 10/2012 | Doronina |
| 8,309,300 B2 | 11/2012 | Junutula |
| 8,343,928 B2 | 1/2013 | Doronina |
| 8,455,622 B2 | 6/2013 | Carter |
| 8,470,329 B2 | 6/2013 | Oflazoglu |
| 8,512,707 B2 | 8/2013 | Doronina |
| 8,545,850 B2 | 10/2013 | Chen |
| 8,557,780 B2 | 10/2013 | Doronina et al. |
| 8,663,642 B2 | 3/2014 | Law |
| 8,691,531 B2 | 4/2014 | Chen |
| 8,703,714 B2 | 4/2014 | Doronina |
| 8,722,857 B2 | 5/2014 | Chen |
| 8,742,076 B2 | 6/2014 | Cohen |
| 8,906,376 B2 | 12/2014 | Senter |
| 9,345,785 B2 | 5/2016 | Law |
| 9,845,355 B2 | 12/2017 | Chen |
| 9,896,506 B2 | 2/2018 | Chen |
| 9,975,949 B2 * | 5/2018 | Sun ................. A61P 43/00 |
| 10,077,318 B2 * | 9/2018 | Bhakta ................. C07K 16/28 |
| 10,494,432 B2 | 12/2019 | Chen |
| 10,544,218 B2 | 1/2020 | Chen |
| 10,981,987 B2 | 4/2021 | Chen et al. |
| RE48,558 E | 5/2021 | Chen et al. |
| 11,000,510 B2 | 5/2021 | Polson et al. |
| 11,648,317 B2 | 5/2023 | Patel et al. |
| 2001/0018422 A1 | 8/2001 | Ritter |
| 2002/0001587 A1 | 1/2002 | Erickson |
| 2002/0150573 A1 | 10/2002 | Nussenzweig |
| 2003/0045682 A1 | 3/2003 | Afar |
| 2003/0083263 A1 | 5/2003 | Doronina |
| 2003/0096743 A1 | 5/2003 | Senter |
| 2003/0103970 A1 | 6/2003 | Tsuchiya |
| 2003/0130189 A1 | 7/2003 | Senter |
| 2004/0001827 A1 | 1/2004 | Dennis |
| 2004/0018194 A1 | 1/2004 | Francisco |
| 2004/0057952 A1 | 3/2004 | Payne |
| 2004/0096392 A1 | 5/2004 | Bhaskar |
| 2004/0141983 A1 | 7/2004 | Law |
| 2004/0191328 A1 | 9/2004 | Warrell |
| 2004/0197325 A1 | 10/2004 | Law |
| 2004/0235068 A1 | 11/2004 | Levinson |
| 2005/0009751 A1 | 1/2005 | Senter |
| 2005/0014687 A1 | 1/2005 | Anderson |
| 2005/0084449 A1 | 4/2005 | Landes |
| 2005/0106644 A1 | 5/2005 | Cairns |
| 2005/0107595 A1 | 5/2005 | Cairns |
| 2005/0113308 A1 | 5/2005 | Senter |
| 2005/0123536 A1 | 6/2005 | Law |
| 2005/0169933 A1 | 8/2005 | Steeves |
| 2005/0180972 A1 | 8/2005 | Wahl |
| 2005/0232929 A1 | 10/2005 | Kadkhodayan |
| 2005/0238649 A1 | 10/2005 | Doronina |
| 2005/0238650 A1 | 10/2005 | Crowley |
| 2005/0256030 A1 | 11/2005 | Feng |
| 2005/0260212 A1 | 11/2005 | Zhang |
| 2005/0272665 A1 | 12/2005 | Schmid |
| 2005/0276812 A1 | 12/2005 | Ebens, Jr. |
| 2006/0008456 A1 | 1/2006 | Tsuchiya |
| 2006/0073152 A1 | 4/2006 | Dennis |
| 2006/0074008 A1 | 4/2006 | Senter |
| 2006/0128970 A1 | 6/2006 | Bliss |
| 2006/0182751 A1 | 8/2006 | Gazzard |
| 2006/0204496 A1 | 9/2006 | Kojima et al. |
| 2006/0233794 A1 | 10/2006 | Law |
| 2007/0092520 A1 | 4/2007 | Dennis |
| 2007/0092940 A1 | 4/2007 | Eigenbrot |
| 2007/0098715 A1 | 5/2007 | Ettenberg |

(56) References Cited

U.S. PATENT DOCUMENTS

| | | |
|---|---|---|
| 2007/0134243 A1 | 6/2007 | Gazzard |
| 2007/0160617 A1 | 7/2007 | Ma |
| 2007/0207142 A1 | 9/2007 | Crowley |
| 2007/0212356 A1 | 9/2007 | Chen |
| 2007/0258987 A1 | 11/2007 | Francisco |
| 2008/0089885 A1 | 4/2008 | Smith |
| 2008/0171040 A1 | 7/2008 | Ebens |
| 2008/0213289 A1 | 9/2008 | Francisco |
| 2008/0226657 A1 | 9/2008 | Doronina |
| 2008/0248051 A1 | 10/2008 | Doronina |
| 2008/0248053 A1 | 10/2008 | Doronina |
| 2009/0028856 A1 | 1/2009 | Chen |
| 2009/0041791 A1 | 2/2009 | Feng |
| 2009/0047296 A1 | 2/2009 | Doronina |
| 2009/0053226 A1 | 2/2009 | Crowley |
| 2009/0068178 A1 | 3/2009 | Crowley |
| 2009/0068202 A1 | 3/2009 | Chen |
| 2009/0175865 A1 | 7/2009 | Eigenbrot |
| 2009/0202536 A1 | 8/2009 | Ebens, Jr. |
| 2009/0226465 A1 | 9/2009 | Jackson |
| 2009/0324621 A1 | 12/2009 | Senter |
| 2010/0003766 A1 | 1/2010 | Eigenbrot |
| 2010/0062008 A1 | 3/2010 | Senter |
| 2010/0111856 A1 | 5/2010 | Gill |
| 2010/0150925 A1 | 6/2010 | Law |
| 2010/0158909 A1 | 6/2010 | Mcdonagh |
| 2010/0158910 A1 | 6/2010 | Law |
| 2010/0183636 A1 | 7/2010 | Law |
| 2010/0215669 A1 | 8/2010 | Chen |
| 2010/0260786 A1 | 10/2010 | Doronina |
| 2010/0273843 A1 | 10/2010 | Feng |
| 2011/0042260 A1 | 2/2011 | Crowley |
| 2011/0045005 A1 | 2/2011 | Crowley |
| 2011/0064753 A1 | 3/2011 | Senter |
| 2011/0070243 A1 | 3/2011 | Crowley |
| 2011/0070248 A1 | 3/2011 | Ichikawa |
| 2011/0076287 A1 | 3/2011 | Cohen |
| 2011/0135667 A1 | 6/2011 | Chen |
| 2011/0137017 A1 | 6/2011 | Eigenbrot |
| 2011/0150908 A1 | 6/2011 | Law |
| 2012/0003247 A1 | 1/2012 | Doronina |
| 2012/0003248 A1 | 1/2012 | Doronina |
| 2012/0027783 A1 | 2/2012 | Doronina |
| 2012/0027784 A1 | 2/2012 | Doronina |
| 2012/0034246 A1 | 2/2012 | Doronina |
| 2012/0034247 A1 | 2/2012 | Doronina |
| 2012/0035134 A1 | 2/2012 | Diebold et al. |
| 2012/0087915 A1 | 4/2012 | Buggy |
| 2012/0141508 A1 | 6/2012 | Doronina |
| 2012/0141509 A1 | 6/2012 | Doronina |
| 2012/0141510 A1 | 6/2012 | Doronina |
| 2012/0148600 A1 | 6/2012 | Chen |
| 2012/0148608 A1 | 6/2012 | Doronina |
| 2012/0148610 A1 | 6/2012 | Doronina |
| 2014/0030280 A1 | 1/2014 | Polakis |
| 2014/0099260 A1 | 4/2014 | Chen |
| 2014/0220047 A1 | 8/2014 | Doronina |
| 2014/0248262 A1 | 9/2014 | Sampath |
| 2014/0335107 A1 | 11/2014 | Chen |
| 2014/0356352 A1 | 12/2014 | Klein et al. |
| 2015/0017094 A1 | 1/2015 | Gill |
| 2015/0017188 A1 | 1/2015 | Eigenbrot, Jr. |
| 2015/0125446 A1* | 5/2015 | Klein .......... A61K 45/06 424/174.1 |
| 2015/0314016 A1 | 11/2015 | Chen |
| 2016/0082120 A1 | 3/2016 | Polson |
| 2016/0130358 A1 | 5/2016 | Bhakta et al. |
| 2016/0159906 A1 | 6/2016 | Sun |
| 2017/0000897 A1 | 1/2017 | Doronina |
| 2017/0058032 A1 | 3/2017 | Chen |
| 2017/0304438 A1 | 10/2017 | Polson |
| 2018/0127512 A1 | 5/2018 | Doronina |
| 2018/0133315 A1 | 5/2018 | Klein et al. |
| 2018/0201679 A1 | 7/2018 | Chen |
| 2018/0327492 A1 | 11/2018 | Sun |
| 2018/0344848 A1 | 12/2018 | Klein et al. |
| 2019/0201382 A1 | 7/2019 | Polson |
| 2019/0276550 A9 | 9/2019 | Chen |
| 2019/0314517 A1 | 10/2019 | Patel et al. |
| 2020/0079852 A1 | 3/2020 | Chen |
| 2020/0247887 A1 | 8/2020 | Chen et al. |
| 2021/0115141 A1 | 4/2021 | Hernandez Montalvo et al. |
| 2021/0138065 A1 | 5/2021 | Klein et al. |
| 2021/0346352 A1 | 11/2021 | Polson et al. |
| 2022/0023437 A1 | 1/2022 | Chen et al. |
| 2022/0031861 A1 | 2/2022 | Hirata et al. |
| 2022/0125942 A1 | 4/2022 | Musick et al. |
| 2022/0251197 A1 | 8/2022 | Chen et al. |
| 2023/0099756 A1 | 3/2023 | Hirata et al. |
| 2023/0270875 A1 | 8/2023 | Hirata et al. |

FOREIGN PATENT DOCUMENTS

| | | |
|---|---|---|
| CA | 2580141 A1 | 3/2006 |
| CA | 2712518 A1 | 8/2009 |
| CL | 2008002083 A1 | 11/2008 |
| CL | 2008002085 A1 | 11/2008 |
| CN | 101065151 A | 10/2007 |
| EP | 0598129 A1 | 5/1994 |
| EP | 0603735 A2 | 6/1994 |
| EP | 0695757 A2 | 2/1996 |
| EP | 0695758 A2 | 2/1996 |
| EP | 0695759 A2 | 2/1996 |
| EP | 0425235 B1 | 9/1996 |
| EP | 1391213 A1 | 2/2004 |
| EP | 1013761 B1 | 8/2007 |
| EP | 1689432 B1 | 12/2009 |
| EP | 2301568 A1 | 3/2011 |
| EP | 2295073 B1 | 4/2014 |
| EP | 2161283 B1 | 6/2014 |
| JP | H06234790 A | 8/1994 |
| JP | H08059693 A | 3/1996 |
| JP | H0977791 A | 3/1997 |
| JP | 2008500017 A | 1/2008 |
| JP | 2010533496 A | 10/2010 |
| PE | 09432009 A1 | 8/2009 |
| RU | 2221809 C2 | 1/2004 |
| RU | 2285541 C2 | 10/2006 |
| WO | 1993003054 A1 | 2/1993 |
| WO | 1995009864 A1 | 4/1995 |
| WO | 1996014856 A1 | 5/1996 |
| WO | 1996022384 A1 | 7/1996 |
| WO | 1996033212 A1 | 10/1996 |
| WO | 1997025068 A2 | 7/1997 |
| WO | 1999035164 A1 | 7/1999 |
| WO | 1999042075 A2 | 8/1999 |
| WO | 200012130 A1 | 3/2000 |
| WO | 2001018032 A2 | 3/2001 |
| WO | 200131065 A1 | 5/2001 |
| WO | 200145746 A2 | 6/2001 |
| WO | 2001040276 A2 | 6/2001 |
| WO | 2001057188 A2 | 8/2001 |
| WO | 200171005 A2 | 9/2001 |
| WO | 200174388 A1 | 10/2001 |
| WO | 2002043661 A2 | 6/2002 |
| WO | 2002083866 A2 | 10/2002 |
| WO | 2002088172 A2 | 11/2002 |
| WO | 2002098883 A1 | 12/2002 |
| WO | 2003008378 A1 | 1/2003 |
| WO | 2003022995 A2 | 3/2003 |
| WO | 2003024392 A2 | 3/2003 |
| WO | 2003034903 A2 | 5/2003 |
| WO | 2003043583 A2 | 5/2003 |
| WO | 2003062401 A2 | 7/2003 |
| WO | 2003072036 A2 | 9/2003 |
| WO | 2003074567 A2 | 9/2003 |
| WO | 2003105758 A2 | 12/2003 |
| WO | 2004001004 A2 | 12/2003 |
| WO | 2004006955 A1 | 1/2004 |
| WO | 2004010957 A2 | 2/2004 |
| WO | 2004016225 A2 | 2/2004 |
| WO | 2004032828 A2 | 4/2004 |
| WO | 2004045516 A2 | 6/2004 |
| WO | 2004050849 A2 | 6/2004 |

(56) References Cited

FOREIGN PATENT DOCUMENTS

| | | |
|---|---|---|
| WO | 2004060919 A1 | 7/2004 |
| WO | 2004073656 A2 | 9/2004 |
| WO | 2005037992 A2 | 4/2005 |
| WO | 2005044859 A2 | 5/2005 |
| WO | 2005049075 A2 | 6/2005 |
| WO | 2005081711 A2 | 9/2005 |
| WO | 2005084390 A2 | 9/2005 |
| WO | 2005101017 A1 | 10/2005 |
| WO | 2005117986 A2 | 12/2005 |
| WO | 2006002114 A2 | 1/2006 |
| WO | 2006014335 A2 | 2/2006 |
| WO | 2006017173 A1 | 2/2006 |
| WO | 2006034488 A2 | 3/2006 |
| WO | 2006060533 A2 | 6/2006 |
| WO | 2006071441 A2 | 7/2006 |
| WO | 2006073941 A2 | 7/2006 |
| WO | 2006083936 A2 | 8/2006 |
| WO | 2007001851 A2 | 1/2007 |
| WO | 2007008603 A1 | 1/2007 |
| WO | 2007008848 A2 | 1/2007 |
| WO | 2007030642 A2 | 3/2007 |
| WO | 2007059082 A1 | 5/2007 |
| WO | 2007062138 A2 | 5/2007 |
| WO | 2007064345 A2 | 6/2007 |
| WO | 2007100385 A2 | 9/2007 |
| WO | 2007109567 A1 | 9/2007 |
| WO | 2007140371 A2 | 12/2007 |
| WO | 2008150494 A1 | 12/2008 |
| WO | 2007070538 A2 | 1/2009 |
| WO | 2009012256 A1 | 1/2009 |
| WO | 2009012268 A1 | 1/2009 |
| WO | 2009099719 A2 | 8/2009 |
| WO | 2009099728 A1 | 8/2009 |
| WO | 2009099741 A1 | 8/2009 |
| WO | 2011018224 A1 | 2/2011 |
| WO | 2011056983 A1 | 5/2011 |
| WO | 2014177615 A2 | 11/2014 |
| WO | 2015084892 A1 | 6/2015 |
| WO | 2016049214 A1 | 3/2016 |

OTHER PUBLICATIONS

FDA (Jun. 2019). "POLIVY—Highlights of Prescribing Information," FDA, 19 pages.
Lu, D. et al. (2017, e-pub. Mar. 8, 2017). "Time-to-Event Analysis of Polatuzumab Vedotin-Induced Peripheral Neuropathy to Assist in the Comparison of Clinical Dosing Regiments," CPT Pharmacometrics Sys. Pharmacol. 6:401-408.
Lu, D. et al. (Feb. 2015). "Population Pharmacokinetics and Exposure-Response Assessment of Anti-CD79B Antibody Drug Conjugate in Patients: Interim Analysis Results," Poster Session II, 97(suppl. 1):S60-S96, Abstract No. PII-095, 37 pages.
Lu, T. et al. (2020, e-pub. Jul. 24, 2020). "Exposure-Safety and Exposure-Efficacy Analyses of Polatuzumab Vedotin in Patients With Relapsed or Refractory Diffuse Large B-Cell Lymphoma," Leukemia & Lymphoma 61(12):2905-2914.
Morschhauser, F. et al. (May 2019, e-pub. Mar. 29, 2019). "Polatuzumab Vedotin or Pinatuzumab Vedotin Plus Rituximab in Patients With Relapsed or Refractory Non-Hodgkin Lymphoma: Final Results From a Phase 2 Randomized Study (ROMULUS)," Lancet Haematol. 6:e254-e265, with Supplement, 29 pages.
Palanca-Wessels, M.C. et al. (Jun. 2015, e-pub. Apr. 27, 2015). "Safety and Activity of the Anti-CD79B Antibody-Drug Conjugate Polatuzumab Vedotin in Relapsed or Refractory B-Cell Non-Hodgkin Lymphoma and Chronic Lymphocytic Leukaemia: A Phase 1 Study," Lancet Oncol. 16:704-715.
Sehn, L.H. et al. (Jan. 10, 2020, e-pub. Nov. 6, 2019). "Polatuzumab Vedotin in Relapsed or Refractory Diffuse Large B-Cell Lymphoma," Journal of Clinical Oncology 38(2):155-165, 22 pages.
Tilly, H. et al. (Jul. 2019, e-pub. May 14, 2019). "Polatuzumab Vedotin in Combination With Immunochemotherapy in Patients With Previously Untreated Diffuse Large B-Cell Lymphoma: An Open-Label, Non-Randomised, Phase 1b-2 Study," Lancet Oncol. 20:998-1010.
U.S. Appl. No. 18/048,986, filed Oct. 24, 2022, Hirata, J.H. (Copy not submitted herewith pursuant to the waiver of 37 C.F.R. 1.98(a)(2)(iii) issued by the Office dated Sep. 21, 2004).
Afar, D.E.H. et al. (Aug. 2004). "Preclinical Validation Of Anti-TMEFF2-Auristatin E-Conjugated Antibodies In The Treatment Of Prostate Cancer," Molecular Cancer Therapeutics 3(8):921-932.
Aherne, G.W. et al. (1996). "Antitumour evaluation of dolastatins 10 and 15 and their measurements in plasma by radioimmunoassay," Cancer Chemother. Pharmacol. 38:225-323.
Ahmed, S.I. et al. (2000). "Studies on the Expression of Endothelin, Its Receptor Subtypes, and Converting Enzymes in Lung Cancer and in Human Bronchial Epithelium," Am. J. Respir. Cell. Mol. 22:422-431.
Alfarano, A. et al. (Apr. 1, 1999). "An Alternatively Spliced Form Of CD79b Gene May Account For Altered B-Cell Receptor Expression In B-Chronic Lymphocytic Leukemia," Blood 93(7):2327-2335.
Alley, S. et al. (2004). "Controlling The Location Of Drug Attachment In Antibody-Drug Conjugates," Proceedings of the AACR, vol. 45, Abstract # 627, 1 page.
Almagro, J.C. et al. (Jan. 1, 2008). "Humanization of Antibodies," Front. Biosci. 13:1619-1633.
Anonoymous. (Feb. 19, 2013). "A Randomized, Open-Label, Multicenter, Phase II Trial Evaluating the Safety and Activity of DCDT2980S in Combination With Rituximab or DCDS4501A in Combination With Rituximab in Patients With Relapsed or Refractory Bcell Non Hodgkin's Lymphoma," located at http://clinicaltrials.gov.archieve/NCT01691898/2013_02_19, last visited on Mar. 22, 2019, 3 pages.
Asundi, J. et al. (Jan. 18, 2011). "An Antibody-Drug Conjugate Targeting the Endothelin B Receptor for the Treatment of Melanoma," Clin. Cancer Res 17:965-975.
Baldwin, R.W. et al. (Mar. 15, 1986). "Monoclonal Antibodies in Cancer Treatment," Lancet 1(8481)603-605.
Barbas III, C.F. et al. (Apr. 1994). "In Vitro Evolution Of A Neutralizing Human Antibody To Human Immunodeficiency Virus Type 1 To Enhance Affinity and Broaden Strain Cross-Reactivity," Proc Nat. Acad. Sci. USA 91:3809-3813.
Beerli, R.R. et al. (Jul./Aug. 2010). "Mining Human Antibody Repertoires," MAbs 2:365-378.
Bernhard, S.L. et al. (1994). "Cysteine Analogs Of Recombinant Barley Ribosome Inactivating Protein Form Antibody Conjugates With Enhanced Stability and Potency In Vitro," Bioconjug. Chem. 5(2):126-132.
Better, M. et al. (Apr. 1, 1994). "Gelonin Analogs With Engineered Cysteine Residues Form Antibody Immunoconjugates With Unique Properties," J. Biol. Chem. 269(13):9644-9650.
Bhaskar, V. et al. (Oct. 1, 2003). "E-Selectin Up-Regulation Allows for Targeted Drug Delivery in Prostate Cancer," Cancer Research 63:6387-6394.
Boerner, P. et al. (Jul. 1, 1991). "Production of a Antigen-Specific Human Monoclonal Antibodies from In Vitro-Primed Human Splenocytes," J. Immunol. 147(1):86-95.
Boring, C.C. et al. (Jan.-Feb. 1993). "Cancer Statistics, 1993," CA Cancer J. Clin. 43(1):7-26.
Bowman, R.E. et al. (Feb. 13, 1950). "N-Substituted Amino-Acids. Part I. A New Method of Preparation of Dimethylamino-Acids," J. Chem. Soc. pp. 1342-1351.
Bradley, C.M. et al. (2002). "Limits of Cooperativity in a Structurally Modular Protein: Response of the Notch Ankyrin Domain to analogous Alanine Substitutions in Each Request," J. Mol. Biol. 324:373-386.
Cabezudo, E. et al. (May 1999). "Quantitative Analysis Of CD79b, CDS and CD19 In Mature B-Cell Lymphoproliferative Disorders," Haematologica 84(5):413-418.
Carayannopoulos, L. et al. (1993). "Chapter 9 Immunoglobulins—Structure and Function", Fundamental Immunology, 3rd Edition, Edited by William E. Paul, pp. 283-295.

(56) References Cited

OTHER PUBLICATIONS

Carl, P.L. et al. (May 1981). "A Novel Connector Linkage Applicable in Prodrug Design," Journal of Medicinal Chemistry 24(5):479-480.
Carter, P. et al. (May 1992). "Humanization of an Anti-p185HER2 Antibody For Human Cancer Therapy," Proc. Natl. Acad. Sci. USA 89:4285-4289.
Carter, P. et al. (Nov. 2001). "Improving the Efficacy of Antibody-Based Cancer Therapies," Nature Reviews, (1):118-129.
Carter, P.J. et al. (May/Jun. 2008). "Antibody-Drug Conjugates for Cancer Therapy," The Cancer Journal 14(3):154-169.
Chari, R.V.J. et al. (Jan. 1, 1992). "Immunoconjugates Containing Noveal maytansinoids: Promising Anticancer Drugs," Cancer Res. 52:127-131.
Chen, Y. et al. (1999). "Selection and Analysis of an Optimized Anti-VEGF Antibody: Crystal Structure of an Affinity-Matured Fab In Complex With Antigen," J. Mol. Biol 293:865-881.
Chen, Y. et al. (May 15, 2007). "Armed Antibodies Targeting The Mucin Repeats Of The Ovarian Cancer Antigen, MUC16, Are Highly Efficacious In Animal Tumor Models," Cancer Res. 67(10):4924-4932.
Chmura, A.J. et al. (Jul. 17, 2001). "Antibodies With Infinite Affinity," Proc. Natl. Acad. Sci. USA 98(15):8480-8484.
Chothia, C. et al. (Aug. 20, 1987). "Canonical Structures for the Hypervariable Regions of Immunoglobulins," J. Mol. Biol. 196(4):901-917.
Chu, Y-W. et al. (Mar. 1, 2013). "Antibody-Drug Conjugates for the Treatment of B-cell Non-Hodgkin's Lymphoma and Leukemia," Future Oncol. 9(3):355-368.
Cole, S.P.C. et al. (1985). "The EBV-Hybridoma Technique and Its Applicaton to Human Lung Cancer," in Monoclonal Antibodies and Cancer Therapy, Alan R. Liss, p. 77-96.
Coleman, P.M. (1994). "Effects Of Amino Acid Sequence Changes On Antibody-Antigen Interactions" Research in Immunology 145:33-36.
Cragg, M.S. et al. (Nov. 1, 2002). "The-Alternative Transcript Of CD79b Is Overexpressed In B-CLL and Inhibits Signaling For Apoptosis," Blood 100(9):3068-3076.
Cruse, J.M. et al. (2003). "Hybridomas, T cell," in Illustrated Dictionary of Immunology Second Edition CRC Press, LLC. pp. 294.
Davies, J. et al. (1996) "Affinity Improvement Of Single Antibody VH Domains: Residues In All Three Hypervariable Regions Affect Antigen Binding," Immunol. 2:169-179.
De Pascalis, R. et al. (2002). "Grafting of "Abbreviated" Complementarity-Determining Regions Containing Specificity-Determining Residues Essential for Ligand Contact to Engineer A Less Immunogenic Humanized Monoclonal Antibody," Journal of Immunology 169:3076-3084.
Demunter, A. et al. (2001, e-pub. Feb. 15, 2001). "Expression of the Endothelin-B Receptor in Pigment Cell Lesions of the Skin Evidence for its Role as Tumor Progression Marker in Malignant Melanoma," Virchows Arch. 438:485-491.
Dennis, M.S. et al. (Sep. 20, 2002). "Albumin Binding as a General Strategy for Improving the Pharmacokinetics of Proteins," J Biol Chem. 277(38):35035-35043.
Dermer, G.B. (Mar. 12, 1994). "Another Anniversary for the War on Cancer," Bio/Technology 12:320.
Dillman, R.O. (Oct. 1989). "Monoclonal Antibodies for Treating Cancer", Ann. Int. Med., 111:592-603.
Dornan, D. et al. (Sep. 24, 2009, e-pub. Jul. 24, 2009). "Therapeutic Potential of an Anti-CD79b Antibody-Drug Conjugate, Anti-CD79b-vc-MMAE, for the Treatment of Non-Hodgkin Lymphoma," Blood 114(13):2721-2729.
Doronina, S.O. et al. (Jul. 2003). "Development of Potent Monoclonal Antibody Auristatin Conjugates for Cancer Therapy," Nat. Biotechnol. 21(7):778-784.
Doronina, S.O. et al. (Aug. 2004). "Immunoconjugates Comprised of Drugs With Impaired Cellular Permeability: A New Approach to Targeted Therapy," SciFinder search result, abstract of paper from 228th ACS National Meeting held in Philadelphia, PA, Aug. 22-26, 2004, 1 page.
Doronina, S.O. et al. (Jan. 2006). "Enhanced Activity Of Monomethylauristatin F Through Monoclonal Antibody Delivery: Effects Of Linker Technology On Efficacy And Toxicity," Bioconjug. Chem. 17(1):114-124.
Doronina, S.O. et al. (Jul. 2003). "Potent Monoclonal Antibody-Drug Conjugates: The Role of Linker Stability in Efficacy, Toxicity and Specificity," Poster #6425 at the annual meeting of the American Association for Cancer Research, AACR, Washington, D.C., Jul. 11-14, 2003, Proceeding of the American Association for Cancer Research 44:1285-1286.
Dubowchik, G.M. et al. (Oct. 12, 1998). "Cathepsin B-Sensitive Dipeptide Prodrugs. 2. Models of Anticancer Drugs Paclitaxel (Taxol®), Mitomycin C and Doxorubicin," Bioorganic & Medicinal Chemistry Letters 8:3347-3352.
D' Arena, G. et al. (Aug. 2000). "Quantitative Flow Cytometry For The Differential Diagnosis Or Leukemic B-.Cell Chronic Lymphoproliferative Disorders," Am. J. Hematol. 64(4):275-281.
Egidy, G. et al. (Dec. 2000). "Modulation of Human Colon Tumor-Stromal Interactions by the Endothelin System," American Journal of Pathology 157(6):1863-1874.
Elkins, K. et al. (Jul. 17, 2012). "FcRL5 as a Target of Antibody-Drug Conjugates for the Treatment of Multiple Myeloma," Mol. Cancer Ther. 11:2222-2232.
Emery, S.C. et al. (1994). "Humanised Monoclonal Antibodies For Therapeutic Applications," Exp. Opin. Invest. Drugs, 3(3):241-251.
Engert, A. et al. (Jan. 1, 1990). "Evaluation of Ricin A Chain-Containing Immunotoxins Directed Against the CD30 Antigen as Potential Reagents for the Treatment of Hodgkin's Disease," Cancer Research 50:84-88.
Erickson, H. et al. (Apr. 15, 2006) "Antibody-Maytansinoid Conjugates are Activated in Targeted Cancer Cells by Lysosomal Degradation and Linker-Dependent Interacellular Processing," Cancer Res. 66(8):4426-4433.
Extended European Search Report and Search Opinion dated Oct. 13, 2017, for European Patent Application No. 17174600.1, filed on Jun. 6, 2017, "Anti-CD79B Antibodies and Immunoconjugates and Methods if Use," Applicant Genentech, Inc., 10 pages.
Extended European Search Report dated Jul. 12, 2012, for EP Patent Application No. 12157788.6, filed Nov. 5, 2004, 7 pages.
Extended European Search Report dated Jul. 25, 2012, for EP Patent Application No. 12157783.7, dated Nov. 5, 2004, 7 pages.
Extended European Search Report dated Jun. 25, 2012, for EP Patent Application No. 12157776.1, filed on Nov. 5, 2004, 5 pages.
Extended European Search Report dated Nov. 7, 2011, for EP Patent Application No. 10175437.2, filed on Nov. 5, 2004, 25 pages.
Extended European Search Report dated Oct. 6, 2016, for EP Patent Application No. 16184693.6, filed on Nov. 5, 2004, 6 pages.
Extended European Search Report dated Sep. 1, 2009, for European Patent Application No. 04821486.0, filed on Nov. 5, 2004, 3 pages.
Falini, B. et al. (May 16, 1992). "Responses of Refractory Hodgkin's Disease to Monoclonal Anti-CD30 Immunotoxin," The Lancet 339:1195-1196.
Fathi, A.T. et al. (Dec. 3, 2015). "A Phase 1 Study of Denintuzumab Mafodotin (SGN-CD19A) in Adults with Relapsed or Refractory B-Lineage Acute Leukemia (B-ALL) and Highly Aggressive Lymphoma," Blood 126(23):1328, 4 pages.
Fennell, B. J. et al. (2003, e-pub. Mar. 13, 2003). "Effects of the Antimitotic Natural Product Dolastatin 10, and Related Peptides, on the Human Malarial Parasite Plasmodium Falciparum," Journal of Microbial Chemotherapy 51:833-841.
Fisher, R.I. (2000). "Current Therapeutic Paradigm For The Treatment Of Non-Hodgkin's Lymphoma," Semin Oncol. 27(6 Suppl 12):2-8.
Foote, J. et al. (1992). "Antibody Framework Residues Affecting the Conformation of the Hypervariable Loops," J Mol Biol. 224(2):487-499.
Francisco, J.A. et al. (Aug. 15, 2003, e-pub. May 8, 2003). "cAC10-vcMMAE, An Anti-CD30-Monomethyl Auristatin E Conjugate With Potent and Selective Antitumor Activity," Blood 102:1458-1465.

(56) References Cited

OTHER PUBLICATIONS

Francisco, J.A. et al. (Jul. 2003). "SGN-35, an Anti-CD30 Antibody-Drug Conjugate with Potent Antitumor Activity," Poster #770 at the annual meeting of the American Association for Cancer Research, AACR, Washington, D.C. Jul. 11-14, 2003, p. 149.
Frisch, B. et al. (1996, e-pub Feb. 1, 1996). "Synthesis of Short Polyoxyethylene-Based Heterobifunctional Cross-Linking Reagents. Application to the Coupling o Peptides to Liposomes," Bioconjugate Chem. 7(2):180-186.
Gaertner, H.F. et al. (1996, e-pub. Nov. 1, 1995). "Site-Specific Attachment of Functionalized Poly(ethylene glycol) to the Amino Terminus of Proteins," Bioconjugate Chem. 7(1):38-44.
Garman, A.J. (1997). "Fluorescent Labelling Of Proteins and Peptides," in Chapter 4 Biological Techniques Non-Radioactive Labelling, Academic Press Limited, London, pp. 51-63.
Garteiz, D.A. et al. (1998). "Quantitation of Dolastatin-10 Using HPLC/Electrospray Ionization Mass Spectrometry: Application in a Phase I Clinical Trial," Cancer Chemother. Pharmacol. 41:299-306.
Gasdaska, J.R. et al. (2012, e-pub. Feb. 2, 2012). "An Afucosylated Anti-CD20 Monoclonal Antibody With Greater Antibody-Dependent Cellular Cytotoxicity and B-cell Depletion and Lower Complement-Dependent Cytotoxicity Than Rituximab," Molecular Immunology 50(3):134-141.
Genentech, Inc. (Dec. 10, 2017). "Phase II Data Showed Genentech's Investigational Polatuzumab Vedotin Plus Bendamustine and Rituxan (BR) Increased Complete Response Rates Compared to BR Alone in Previously Treated Aggressive Lymphoma," Genentech, Inc., 8 pages.
Genet, J.P. (Jan. 2002). "Recent Studies on Asymmetric Hydrogenation. New Catalysts and Synthetic Applications in Organic Synthesis," Pure Appl. Chem. 74(1):77-83.
Ghetie, V. et al. (Sep. 1994). "Immunotoxins In The Therapy Of Cancer: From Bench To Clinic," Pharmacology and Therapeutics 63(3):209-234.
Gilbert, C.W. et al. (2003). "Targeted Prodrug Treatment of HER-2-Positive Breast Tumor Cells Using Trastuzumab and Paclitaxel Linked by A-Z-CINNTM Linker," Journal of Experimental Therapeutics and Oncology 3:27-35.
Golden, F. (May 18, 1989). "Of Mice and Men: Don't Blame the rodents," Time Australia, May 18, 1998, Issue 20, p. 26, 1/3p, 1c; Accession No. 647245; Database: Business Source Corporate; 2 pages.
Greenwood, J. et al. (Oct. 1994). "Engineering Multiple-Domain Forms Of The Therapeutic Antibody CAMPATH-1H: Effects On Complement Lysis," Therapeutics Immunology 1(5):247-255.
Gura, T. (1997). "Systems for identifying new drugs are often faulty," Science 278(5340):1041-1042.
Hamann, P.R. et al. (2002, e-pub. Dec. 19, 2001). "Gemtuzumab Ozogamicin, A Potent and Selective Anti-CD33 Antibody-Calicheamicin Conjugate for Treatment of Acute Myeloid Leukemia," Bioconjugate Chem. 13(1):47-58.
Hamblett, K.J. et al. (Mar. 2004). "Effect of Drug Loading on the Pharmacology, Pharmacokinetics, and Toxicity of an Anti-CD30 Antibody-Drug Conjugate," Proceedings of the AACR, vol. 45, Abstract # 624, 2 pages.
Harris, N.L. et al. (2000). "The World Health Organization Classification Or Neoplasms Or The Hematopoietic and Lymphoid Tissues: Report of the Clinical Advisory Committee meeting—Airlie House, Virginia, Nov. 1997," Hematol J. 1:53-66.
Hashimoto, S. et al. (Jun. 1995). "Alternative Splicing Of CD79a (Ig-Alpha/mb-I) and CD79b (Ig-Beta/B29) RNA Transcripts In Human B Cells," Mol. Immunol. 32(9):651-659.
Hassan, R. et al. (Jul.-Aug. 2000). "Anti-Tumor Activity of K1-LysPE38QQR, an Immunotoxin Targeting Mesothelin, a Cell-Surface Antigen Overexpressed in Ovarian Cancer and Malignant Mesothelioma," Journal of Immunotherapy 23(4):473-479.
Hatzivassiliou, G. et al. (Mar. 2001). "IRTA1 and IRTA2, Novel Immunoglobulin Superfamily Receptors Expressed in B Cells and Involved in Chromosome 1q21 Abnormalities in B Cell Malignancy," Immunity 14:277-289.

Hawkins, R.E. et al. (1992). "Selection of Phage Antibodies by Binding Affinity: Mimicking Affinity Maturations," J. Mol. Biol. 226:889-896.
Hermanson, G.T. (1996). "Antibody Modification and Conjugation," Bioconjugate Techniques, Pierce Chemical Company, pp. 456-493.
Herrera, L. at al. (Feb. 2003). "Treatment Of SCID/Human B Cell Precursor ALL With Anti-CD19 and Anti-CD22 Immunotoxins," Leukemia 17(2):334-338.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.
Holt, L.J. et al. (Nov. 2003) "Domain Antibodies: Proteins For Therapy," Trends in Biotechnology 21(11):484-490.
Hoogenboom, H.R. et al. (1992). "By-Passing Immunisation. Human Antibodies From Synthetic Repertoires of Germline VH Gene Segments Rearranged in Vitro," J. Mol. Biol. 227:381-388.
Hubert, R.S. et al. (Dec. 7, 1999). "STEAP: A Prostate-Specific Cell-Surface Antigen Highly Expressed in Human Prostate Tumors," Proc. Natl. Acad. Sci. U.S.A. 96(25):14523-14528.
Ide, H. et al. (1997). "Cloning of Human Bone Morphogenetic Protein Type IB Receptor (BMPR-IB) and its Expression in Prostate Cancer in Comparison With Other BMPRs," Oncogene 14:1377-1382.
Inada, Y. et al. (1994). "Modification of Proteins with Polyethylene Glycol Derivatives," Methods in Enzymology 242:65-90.
International Preliminary Report On Patentability, dated Jan. 19, 2010, for PCT Application No. PCT/US2008/070061, filed Jul. 15, 2008, 11 pages.
International Preliminary Report On Patentability, dated Mar. 28, 2017, for PCT Application No. PCT/US2015/051760, filed Sep. 23, 2015, 7 pages.
International Search Report & Written Opinion for PCT Application No. PCT/US04/38392, dated Oct. 2, 2006, filed on Nov. 5, 2004, 11 pages.
International Search Report, dated Dec. 23, 2015, for PCT Application No. PCT/US2015/051760, filed Sep. 23, 2015, 4 pages.
Jackson, J.R. et al. (Apr. 1, 1995). "In Vitro Antibody Maturation. Improvement Of A High Affinity, Neutralizing Antibody Against IL-1 Beta," J. Immunol. 154(7):3310-3319.
Jansen, F.K. et al. (1982). "Immunotoxins: Hybrid Molecules Combining High Specificity and Potent Cytotoxicity," Immunol. Rev. 62:185-216.
Jemal, A. et al. (2002). "Cancer Statistics, 2002" CA Cancer Journal for Physicians 52:23-47.
Jones, P.T. et al. (May 29, 1986). "Replacing the Complementarity-Determining Regions in a Human Antibody With Those From a Mouse," Nature 321:522-525.
Jung, S. et al. (Jun. 8, 2001). "The Importance Of Framework Residues H6, H7 and H10 In Antibody Heavy Chains: Experimental Evidence For A New Structural Subclassification Of Antibody V(H) Domains," J. Mol. Biol. 309(3):701-716.
Junutula, J.R. et al. (2008), "Site-specific conjugation of cytotoxic drug to an antibody improves the therapeutic index," Nat Biotechnol. 26(8):925-932.
Junutula, J.R. et al. (2008). "Rapid Identification Or Reactive Cysteine Residues For Site-Specific Labeling Of Antibody-Fabs," J. Immunol. Methods 332:41-52.
Kabat, E.A. (1991). Sequences of Proteins of Immunological Interest, 5th ed., Public Health Service, National Institutes of Health, Bethesda, MD, pp. 647-723.
Kanno, S. et al. (Jan. 21, 2000). "Assembling Of Engineered IgG-Binding Protein On Gold Surface For Highly Oriented Antibody Immobilization," J. Biotechnol. 76(2-3):207-214.
Kim, I.Y. et al. (Jun. 1, 2000). "Expression of Bone Morphogenetic Protein Receptors Type-IA, -IB, and -II Correlates with Tumor Grade in Human Prostate Cancer Tissues," Cancer Research 60:2840-2844.
King, H.D. et al. (1999, e-pub. Feb. 24, 1999). "Monoclonal Antibody Conjugates of Doxorubicin Prepared with Branched Linkers: A Novel Method for Increasing the Potency of Doxorubicin Immunoconjugates," Bioconjugate Chem. 10(2):279-288.

(56) References Cited

OTHER PUBLICATIONS

King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.
Kline, T. et al. (2004, e-pub. Jan. 12, 2004). "Novel Antitumor Prodrugs Designed for Activation by Matrix Metalloproteinases-2 and -9," Molecular Pharmaceutics 1(1):9-22.
Klussman, K. et al. (2004, e-pub. Jun. 18, 2004). "Secondary mAb--vcMMAE Conjugates are Highly Sensitive Reporters of Antibody Internalization Via the Lysosome Pathway," Bioconjugate Chemistry 15(4):765-773.
Krauss, J. et al. "Impact Of Antibody Framework Residue VH-71 On The Stability Of A Humanized Anti-MUCI scFv and Derived Immunoenzyme," British J. of Cancer 90:1863-1870, (2004, e-pub. Apr. 6, 2004).
Kumagi et al. "Generation Of Novel Functional Antibody Molecules With An In Vitro Selection System," Protein, Nucleic Acid and Enzyme, 43(2):159-167, (Feb. 1998). English Translation.
Kunkel, T.A. et al. (1987). "Rapid and Efficient Site-Specific Mutagenesis without Phenotypic Selection," Meth. Enzymology 154:367-382.
Lambert, J. (2005), "Drug-Conjugated Monoclonal Antibodies for The Treatment of Cancer," Current Opinion in Pharmacology 5:543-549.
Law, C.L. et al. "Lymphocyte Activation Antigen CD70 Expressed by Renal Cell Carcinoma Is a Potential Therapeutic Target for Anti-CD70 Antibody-Drug Conjugates," Cancer Res., 2006; 66(4):2328-2337.
Law, C.L. et al. (Mar. 2004). "CD70 is expressed on renal cell carcinoma and is a potential target for tumor cell elimination by antibody-drug conjugates," Abstract No. 625, Proceedings of the AACR, 95th Annual Meeting, Mar. 27-31, 2004, Orlando, Florida, 45:abstract # 625, 3 pages.
Li, D. et al. (Apr. 18, 2013). "DCDT2980S, an Anti-CD22-Monomethyl Auristatin E Antibody-Drug Conjugate, Is a Potential Treatment for Non-Hodgkin Lymphoma," Mol. Cancer Ther. 12:1255-1265, 37 pages.
Li, J. et al. (Mar. 7, 2006). Human Antibodies for Immunotherapy Development Generated Via a Human B Cell Hybridoma Technology, Proc. Natl. Acad. Sci. USA 103(10):3557-3562.
Liu, C. et al. (Aug. 1996). "Eradication of Large Colon Tumor Xenografts by Targeted Delivery of Maytansinoids," Proc. Natl. Acad. Sci. USA 93:8618-8623.
Lo, B.C.K. (2004). "Antibody Humanization By CDR Grafting," in Methods in Molecular Biology, vol. 248: Antibody Engineering: Methods and Protocols, ed. B.K.C. Lo, Humana Press Inc., Totowa, NJ, pp. 135-159.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lu, D. et al. (Feb. 2013). "Pharmacokinetics (Pk) Of Anti-Cd22 And Anti-Cd79b Antibody Drug Conjugates (Adcsj In Relapsed Or Refractory B-Cell Non-Hodgkin's Lymphoma (Nhl) Patients: Results From Phase I Dose-Escala-Tion Studies," Clinical Pharmacology 93(1):S77-S78, Abstract No. PII-72.
Maccallum, R.M. et al. (Oct. 1996). "Antibody-Antigen Interactions: Contact Analysis and Binding Site Topography," J. Mol. Biol. 262(5):732-745.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002, e-pub. Jun. 19, 2002). "Modifications in Synthesis Strategy Improve the Yield and Efficacy of Geldanamycin-Herceptin Immunoconjugates," Bioconjugate Chem. 13:786-791.
Mandler, R. et al. (Oct. 2000). "Immunoconjugates of Geldananlycin and Anti-HER2 Monoclonal Antibodies: Antiproliferative Activity on Human Breast Carcinoma Cell Lines," J. Nat. Cancer Inst. 92(19):1573-1581.
Mao, W. et al. (Feb. 1, 2004). "EphB2 As A Therapeutic Antibody Drug Target For The Treatment Of Colorectal Cancer," Cancer Research 64:781-788.
Marks, J.D. et al. (1991). "By-Passing Immunization. Human Antibodies From V-Gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Matsuuchi, L. et al. (Jun. 2001). "New views of BCR structure and organization," Curr. Opin. Immunol. 13(3):270-277.
May, R.D. et al. (May 1, 1990). "Evaluation of Ricin a Chain-Containing Immunotoxins Directed Against Different Epitopes On the σ-Chain of Cell Surface-Associated IgD on Murine B Cells," The Journal of Immunology 144(9):3637-3642.
Maynard, J. et al. (2000). "Antibody Engineering," Annu Rev Biomed Eng 2:339-376.
Maškovskij, M.D. Lekarstvennye sredstva. 2 vol.-vol. 1, 12th ed., Moscow: Medicina, 1998—736 pages. (only 16 pages Table of Contents in Russian Only).
Mcdonagh, C.F. et al. (Sep. 2008). "Engineered Anti-CD70 Antibody-Drug Conjugate With Increased Therapeutic Index," Mol. Cancer Ther. 7(9):2913-2923.
Mehta, A. et al. (Jul. 21, 2015). "Development and Integration Of Antibody-Drug Conjugate In Non-Hodgkin Lymphoma," Current Oncology Reports, Current Science, 17(9):41.
Meyer, D. et al. (2002). "Proteolytic vs. Hydrolytic Released Drug from Anti-Tumor Immunochemotherapeutic Agents." Poster Presentation at Gordon Research Conference on Drug Carriers In Medicine & Biology, Feb. 24-Mar. 1, 2002, Ventura, California, USA; 1 page.
Meyer, D.L. et al. (2003). "Recent Advances in Antibody Drug Conjugates for Cancer Therapy," Chapter 23 in Annual Reports in Medical Chemistry 38:229-237.
Miura, Y. et al. (Dec. 15, 1996). "Molecular Cloning Of A Human RP105 Homologue and Chromosomal Localization Of The Mouse and Human RP105 Genes (Ly64 and LY64)," Genomics 38(3):299-304.
Miyake, K. et al. (Apr. 1, 1995). "RP105, A Novel B cell Surface Molecule Implicated In B Cell Activation, Is A Member Of The Leucine-Rich Repeat Protein Family," J. Immunol. 154(7):3333-3340.
Miyazaki, K. et al. (1995). "Synthesis and Antitumor Activity of Novel Dolastatin 10 Analogs," Chem. Pharm. Bull. 43(10):1706-1718.
Mohammad, R.M. et al. (Apr. 1998). "An Orthotopic Model of Human Pancreatic Cancer in Severe Combined Immunodeficient Mice: Potential Application for Preclinical Studies1," Clinical Cancer Research 4:887-894.
Monaghan, S.A. et al. (2003). "Pan B Cell Markers Are Not Redundant in Analysis of Chronic Lymphocytic Leukemia (CLL)," Cytometry Part B (Clinical Cytometry) 56B:30-42.
Morschhauser, F. et al. "Preliminary Results Of A Phase II Randomized Study (ROMULUS) Of Polatuzumab Vedotin (poV) or Pinatuzumab Vedotin (PiV) Plus Rituzimab (RTX) In Patients (pts) With Relapsed/Refractory (R/R) No- Hodgkin Lyphoma (NHL)," J. of Clinical Oncology 32(15-suppl):8519, (May 20, 2014), 5 pages.
Mössner et al. (Jun. 3, 2010). "Increasing the Efficacy of CD20 Antibody Therapy Through the Engineering of a New Type II Anti-CD20 Antibody With Enhanced Direct and Immune Effector Cell-Mediated B-Cell Cytotoxicity," Blood 115(22):4393-4402.
Natsume, T. et al. (Jul. 2000). "Characterization of the Interaction of TZT-1027, a Potent Antitumor Agent, with Tubulin," Jpn. J. Cancer 91:737-747.
Niculesu-Duvaz, I. et al. (1997). "Antibody-Directed Enzyme Prodrug Therapy (ADEPT): A Review," Adv. Drug Del. Rev. 26:151-172.
Noguchi, H. (1993). "Rationale and Clinical Application Of Chimeric and Humanized Antibodies (abstract translated)," J. Clin. Experimental Medicine 167(5): 457-462.
Ohno, S. et al. (May 1985). "Antigen-Binding Specificities Of Antibodies Are Primarily Determined By Seven Residues Of VH," Proc. Natl. Acad. Sci. USA 82:2945-2949.

(56) References Cited

OTHER PUBLICATIONS

Okazaki, M. et al. (Jan. 1, 1993). "Three New Monoclonal Antibodies that Define a Unique Antigen Associated with Prolymphocytic Leukemia/Non-Hodgkin's Lymphoma and are Effectively Internalized After Binding to the Cell Surface Antigen," Blood 81(1):84-94.
Olejniczak, S.H. et al., (2006). "A Quantitative Exploration Of Surface Antigen Expression In Common B-Cell Malignancies Using Flow Cytometry," Immunol. Invest. 35(1):93-114.
Palanca-Wessels, M.C. et al. (2012). "A Phase I Study of the Anti-CD79b Antibody-Drug Conjugate(ADC) DCDS4501A Targeting CD79b in Relapsed or Refractory B-Cell Non-Hodgkin's Lymphoma (NHL)," 54th Annual Meeting and Exposition of the American Society of Hematology (ASH), Atlanta, GA, USA, Dec. 8-11, 2012, Blood 120(21):Abstract No. 56, 3 pages.
Paul, W.E. (1993). "Structure and Function of Immunoglobulins," Chapter 9 in Fundamental Immunology, 3rd Edition, pp. 292-295.
Payne, G. (2003). "Progress In Immunoconjugate Cancer Therapeutics," Cancer Cell vol. 3, pp. 207-212.
Pettit, G.R. (1997). "The Dolastatins," Progress in the Chemistry of Organic Natural Products, Springer-Verlag, New York, 70:1-79.
Pettit, G.R. et al. (1989). "The Absolute Configuration and Synthesis of Natural (-)-Dolastatin 10," J. Am. Chem. Soc. 111(14):5463-5465.
Pettit, G.R. et al. (1994). "The Dolastatins. 17. Synthesis of Dolaproine and Related Diastereoisomers," J. Org. Chem. 59(21):6287-6295.
Pettit, G.R. et al. (1994). "The Dolastatins. 19. Synthesis of Dolaisoleuine," J. Org. Chem. 59(7):1796-1800.
Pettit, G.R. et al. (1996). "Dolastatins 24. Synthesis of (-)-Dolastatin 10. X-Ray Molecular Structure of N,N-Dimethylvalyl-Valyl-Dolaisoleuine Tert-butyl Ester," J. Chem. Soc. Perkin Trans.1 5:859-863.
Pettit, G.R. et al. (1996). "Dolastatins. 23: Stereospecific Synthesis of Dolaisoleuine," J. Chem Soc. Perkin. Trans. 1:853-858.
Pettit, G.R. et al. (1998). "Antineoplastic Agents 365. Dolastatin 10 SAR probes," Anti-Cancer Design 13:243-277.
Pettit, G.R. et al. (2001, e-pub. Nov. 9, 2001). "A Cobalt—Phosphine Complex Directed Reformatsky Approach to a Stereospecific Synthesis of the Dolastatin 10 Unit Dolaproine (Dap)1," J. Org. Chem. 66(25):8640-8642.
Pettit, G.R. et al. (Jun. 1996). "The Dolastatins. 18. Stereospecific Synthesis of Dolaproine," Synthesis 6:719-725.
Pettit, G.R. et al. (Oct. 1995). "Antineoplastic Agents 337. Synthesis of Dolastatin 10 Structural Modifications," Anti-Cancer Drug Design 10(7):529-544.
Pettit, R.K. et al. (Nov. 1998). "Specific Activities of Dolastatin 10 and Peptide Derivatives Against Cryptococcus neoformans," Antimicrobial Agents and Chemotherapy 42(11):2961-2965.
Pini, A. et al. (Aug. 21, 1998). "Design and Use Of A Phage Display Library," J. Biol. Chemistry 273(34):21769-21776.
Polson, A.G. et al. (2007). "Antibody-Drug Conjugates Targeted To CD79 For The Treatment Of Non-Hodgkin Lymphoma," Blood 110(2):616-623.
Polson, A.G. et al. (2011). "Investigational Antibody-Drug Conjugates for Hematological Malignancies," Expert Opin. Investig. Drugs 20(1):75-85.
Pre-Grant Opposition mailed on Dec. 2, 2014, for Indian Patent Application No. 2111/DELNP/2006, 587 pages.
Press Release. (Mar. 24, 2004). "Seattle Genetics, Inc. (SGEN) To Present Advances In Preclinical Research At American Cancer Research Annual Meeting," https://www.businesswire.com/news/home/20040324005219/en/Seattle-Genetics-Present-Advances-Preclinical-Research-AACR, 3 pages.
Press, O.W. et al. (Dec. 15, 1988). "Ricin A-Chain Containing Immunotoxins Directed Against Different Epitopes on the CD2 Molecule Differ In Their Ability to Kill Normal and Malignant T Cells," The Journal of Immunology 141(12):4410-4417.
Presta, L.G. (1992). "Antibody Engineering," Current Opinion in Structural Biology 2:593-596.
Reichmann, L. et al. (Mar. 1988). "Reshaping Human Antibodies for Therapy," Nature 332:323-327.

Roitt et al. "Binding Antibodies to Antigen," Immunology, eds. V.I. Kandror, A.N. Mats, L.A. Pevnitsky, and M.A. Serova, Mir Publishing House, p. 150, (2000), Excerpt, English translation.
Roitt, A. et al. (2000), "Immunology" English Translation by McElroy Translation Company, Moscow "Mir"p. 110-111, eight pages.
Roitt, A. et al., "Immunology" English Translation by McElroy Translation Company, Moscow "Mir" four pages, (2000).
Rosenblum, M.G. et al. (Apr. 1999). "Recombinant Immunotoxins Directed Against the c-erb-2/HER2/neu Oncogene Product: In Vitro Cytotoxicity Pharmacokinetics, and in Vivo Efficacy Studies in Xenograft Models," Clin. Cancer Res. 5:865-874.
Rowland, G.F. et al. (1986). "Drug Localisation And Growth Inhibition Studies of Vindesine-Monoclonal Anti-CEA Conjugates in a Human Tumour Xenograft," Cancer Immunol. Immunother. 21:183-187.
Rudikoff, S. et al. (Mar. 1982). "Single Amino Acid Substitution Altering Antigen-Binding Specificity," Proc. Natl. Acad. Sci. USA 79:1979-1983.
Rudinger, J. (Jun. 1976). "Characteristics of the Amino Acids as Components of a Peptide Hormone Sequence," in Peptide Hormones, Parsons, J.A. ed., National Institute for Medical Research, Mill Hill, London, pp. 1-7, total p. 9.
Rummel, M.J. et al. (Apr. 6, 2013, e-pub. Feb. 20, 2013). "Bendamustine Plus Rituximab Versus CHOP Plus Rituximab As First-Line Treatment For Patients With Indolent and Mantle-Cell Lymphomas: An Open-Label, Multicentre, Randomised, Phase 3 Non-Inferiority Trial," The Lancet 381(9873):1203-1210.
Russian Decision to Grant dated Feb. 24, 2015, for Russian application No. 2010136302, 38 pages with English Translation.
Sakahara, H. et al. "Effect of DTPA Conjugation On The Antigen Binding Activity And Biodisruption Of Monoclonal Antibodies Against α-Fetoprotein," J. Nuc. Med. 26:750-755, (1985).
Schier, R. et al. (1995). "Identification of Functional and Structural Amino-Acid Residues by Parsimonious Mutagenesis," Gene 169:147-155.
Schnell, R. et al. (1995). "Development of New Ricin A-Chain Immunotoxins With Potent Anti-Tumor Effects Against Human Hodgkin Cells In Vitro And Disseminated Hodgkin Tumors in SCID Mice Using High-Affinity Monoclonal Antibodies Directed Against The CD30 Antigen," Int. J. Cancer 63:238-244.
Schoffski, P. et al. (2004). "Phase I and Pharmacokinetic Study of TZT-1027, a Novel Synthetic Dolastatin 10 Derivative, Administered as a 1-hour Intravenous Infusion Every 3 Weeks in Patients with Advanced Refractory Cancer," Annals of Oncology 15:671-679.
Sehn, L.H et al. (Dec. 7, 2017). "Addition of Polatuzumab Vedotin to Bendamustine and Rituximab (BR) Improves Outcomes in Transplant-Ineligible Patients with Relapsed/Refractory (R/R) Diffuse Large B-Cell Lymphoma (DLBCL)Versus BR Alone: Results from a Randomized Phase 2 Study," BLOOD 130(1):2821, 8 pages.
Sehn, L.H. et al. (2018). "Randomized Phase 2 Trial of Polatuzumab Vedotin With Bendamustine and Rituximab in Relapsed/Refractory FL and DLBCL," presented at ASCO Annual Meeting, 2018, 20 pages.
Sehn, L.H. et al. (May 2018, e-pub. Jun. 1, 2018). "Randomized Phase 2 Trial of Polatuzumab Vedotin (pola) With Bendamustine and Rituximab (BR) in Relapsed/Refractory (r/r) FL and DLBCL," Journal of Clinical Oncology Abstract No. 7507, 5 pages.
Senter, P. et al. (2004), "Immunoconjugates Comprised Of Drugs With Impaired Cellular Permeability: A New Approach To Targeted Therapy, Abstract No. 623, presented on Mar. 28, 2004, Proceedings of the American Association for Cancer Research," 45:36, 4 pages.
Senter, P. et al. (Mar. 2002). "Cures and Regressions of Established Tumors with Monoclonal Antibody-Auristatin E Conjugates." Abstract No. 2062, Presentation at the 93rd Annual Meeting of the American Association for Cancer Research, Apr. 6-10, 2002, San Francisco, California, 43:415, 4 pages.
Severin et al. (2000). "Biochemistry," Medisina, ISBN: 5-225-04188-4, p. 7. (Translation of lines 6-8).
Shen, Z. et al. (Nov. 1, 2005). "Engineered Recombinant Single-Chain Fragment Variable Antibody for Immunosensors," Anal. Chem. 77(21):6834-6842, 23 pages.

(56) References Cited

OTHER PUBLICATIONS

Shioiri, T. et al. (1993). "Stereoselective Synthesis of Dolastatin 10 and its Congeners," Tetrahedron 49(9):1913-1924.
Smith, L.M. et al. (2008, e-pub. Jun. 10, 2008). "CDl33/Prominin-l is a Potential Therapeutic Target for Antibody-Drug Conjugates in Hepatocellular and Gastric Cancers," British Journal of Cancer 99(1):100-109.
Statement of Applicant filed on Feb. 7, 2017, in Response to Pre-Grant Opposition for Indian Patent Application No. 2111/DELNP/2006, 79 pages.
Sutherland, M.S.K. et al. (2006, e-pub. Feb. 16, 2006). "Lysosomal Trafficking and Cysteine Protease Metabolism Confer Target-specific Cytotoxicity by Peptide-linked Anti-CD30-Auristatin Conjugates," Journal of Biological Chemistry 281(15):10540-10547, 19 pages.
Sweet, F. et al. (1989). "Daunorubicin Conjugated to a Monoclonal Anti-CA125 Antibody Selectively Kills Human Ovarian Cancer Cells," Gynecologic Oncology 34(3):305-311.
Syrigos, K. et al. (1999). "Antibody Directed Enzyme Prodrug Therapy (ADEPT): A Review of the Experimental and Clinical Considerations," Anticancer Research 19:605-614.
Szatrowski, T.P. et al. (Mar. 15, 2003). "Lineage Specific Treatment Of Adult Patients With Acute Lymphoblastic Leukemia In First Remission With Anti-B4-Blocked Ricin Or High-Dose Cytarabine: Cancer and Leukemia Group B Study 93," Cancer 97(6):1471-1480.
Thornber, C. W. (1979). "Isosterism and Molecular Modification in Drug Design." Chem. Soc. Rev. 8(4):563-580.
Thorpe, (1985). "Antibody Carriers Of Cytotoxic Agents In Cancer Therapy: A Review," in Monoclonal Antibodies '84: Biological And Clinical Applications, Pincheraet al. (eds.), pp. 475-506.
Tobinai, K. (Aug. 2003). "Rituximab and Other Emerging Antibodies As Molecular Target-Based Therapy Of Lymphoma," Int. J. Clin. Oncol. 8(4):212-223.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
Toki, B.E. et al. (Apr. 2002). "Cures and Regressions of Established Tumor Xenographs With Monoclonal Antibody Auristatin E Conjugates," Abstract No. 147, 223rd ACS Meeting, Orlando FL, Apr. 7-11, 2002, 3 pages.
Tomioka, K. et al. (1991). "An Expeditious Synthesis of Dolastatin 10," Tetrahedron Letters 32(21):2395-2398.
Trail, P.A. et al. (Jan. 1, 1997). "Effects of Linker Variation on the Stability, Potency, and Efficacy of Carcinoma-Reactive BR64-Doxorubicin Immunoconjugates," Cancer Research 57:100-105.
Trail, P.A. et al. (Jul. 9, 1993). "Cure of Xenografted Human Carcinomas by BR-96-Doxorubicin Immunoconjugates," Science 261(5118):212-215.
Tsutsumi, Y. et al. (Jul. 18, 2000). "Site-Specific Chemical Modification with Polyethylene Glycol of Recombinant Immunotoxin Anti-Tac(Fv)-PE38(LMB-2) Improves Antitumor Activity and Reduces Animal Toxicity and Immunogenicity," Proc. Natl. Acad. Sci. U.S.A. 97(15):8548-8553.
Tu, B.P. et al. (Apr. 1999). "Protein Footprinting At Cysteines: Probing ATP-Modulated Contacts In Cysteine-Substitution Mutants Of Yeast DNA Topoisomerase II" Proc. Natl. Acad. Sci. USA. 96(9):4862-4867.
Van Den Bent, M.J. et al. (May 20, 2016). "Efficacy of a Novel Antibody-Drug Conjugate (ADC), ABT-414, as Monotherapy in Epidermal Growth Factor Receptor (EGFR) Amplified, Recurrent Glioblastoma (GBM)," J. Clin. Oncol .34(15S)(Suppl. Pt. 1):Abstract No. 2542, 2016 ASCO 52nd Annual Meeting Jun. 3-7, 2016, McCormick Place, Chicago, IL, p. 124S, 2 pages.
Van Dijk, M.A. et al. (Aug. 2001). "Human Antibodies as Next Generation Therapeutics," Curr. Opin. Che. Biology 5(4):368-374.
Vasile, S. et al. (1994). "Isolation and Chemical Characterization Of The Human B29 and mb-1 Proteins Of the B Cell Antigen Receptor Complex," Molecular Immunology 31(6):419-427.
Verdier-Pinard, P. et al. (2000). "Sustained Intracellular Retention of Dolastatin 10 Causes Its Potent Antimitotic Activity," Molecular Pharmacology 57:180-187.
Verhoeyen, M. et al. (Mar. 25, 1988). "Reshaping Human Antibodies: Grafting an Antilysozyme Activity," Science 239:1534-1536.
Vippagunta, S.R. et al. (2001). "Crystalline Solids," Advanced Drug Delivery Reviews 48:3-26.
Wahl, A. F. et al. (Jul. 2003). "Anti-Cancer Activity of High Potency Anti-CD20 Antibody-Drug Conjugates," Abstract No. 769 at the annual meeting of the American Association for Cancer Research, AACR, Washington, D.C., Jul. 11-14, 2003, 44:149, 3 pages.
WHO Drug Information, 2008, vol. 22, No. 2, pp. 123-124.
WHO Drug Information, 2012, vol. 26, No. 4, p. 453.
Wilson, G.L. et al. (Jan. 1, 1991). "cDNA Cloning of the B Cell Membrane Protein CD22: A Mediator of B-B Cell Interactions," J. Exp. Med. 173:137-146.
Winter, G. et al. (1993). "Antibody-Based Therapy. Humanized Antibodies," Immunology Today 14(6):243-246.
Winter, G. et al. (1994). "Making Antibodies by Phage Display Technology," Ann. Rev. Immunol. 12:433-455.
Winter. G. et al. (May 1993). "Antibody-Based Therapy. Humanized Antibodies," TiPS 14:139-143.
Woyke, T. et al. (Dec. 2002). "Effect of Auristatin PHE on Microtube Integrity and Nuclear Localization in Cryptococcus neoformans," Antimicrobial Agents and Chemotherapy 46(12):3802-3808.
Woyke, T. et al. (Dec. 2002). "In Vitro Activities and Postantifungal Effects of the Potent Dolastatin 10 Derivative Auristatin PHE," Antimicrobial Agents and Chemotherapy 45(12):3580-3584.
Written Opinion Of The International Searching Authority, dated Dec. 23, 2015, for PCT Application No. PCT/US2015/051760, filed Sep. 23, 2015, 6 pages.
Written Opinion Of The International Searching Authority, dated Jan. 19, 2010, for PCT Application No. PCT/US2008/070061, filed Jul. 15, 2008, 10 pages.
Wu, A.M. et al. (Sep. 2005, e-pub. Sep. 7, 2005). "Arming Antibodies: Prospects and Challenges for Immunoconjugates," Nature Biotechnology 23(9):1137-1146.
Yamada, N. et al. (1996). "Bone Morphogenetic Protein Type IB Receptor is Progressively Expressed in Malignant Glioma Tumours," British Journal of Cancer 73:624-629.
Yamashita, Y. et al. (Jul. 1, 1996). "Activation Mediated By RP105 But Not CD40 Makes Normal B Cells Susceptible To Anti-IgM-Induced Apoptosis: A Role For Fc Receptor Coligation," J. Exp. Med. 184(1):113-120.
Yelton, D.E. et al. (1995). "Affinity Maturation of the BR96 Anti-Carcinoma Antibody by Codon-Based Mutagenesis," J. Immunol. 155:1994-2004.
Zhang, W. et al. (Dec. 1, 2002). "Complete Disulfide Bond Assignment Of A Recombinant Immunoglobulin G4 Monoclonal Antibody," Analytical Biochemistry 311(1):1-9.
Zheng, B. et al. (Oct. 2009, e-pub. Oct. 6, 2009). "In Vivo Effects of Targeting CD79b With Antibodies and Antibody-Drug Conjugates," Mol. Cancer Ther. 8(10):2937-2946.
Zomas, A.P. et al. (Dec. 1996). "Expression Of The Immunoglobulin-Associated Protein B29 In B Cell Disorders With The Monoclonal Antibody SN8 (CD79b)," Leukemia 10:1966-1970.
U.S. Appl. No. 17/316,592, filed May 10, 2021, by Polson et al. (A copy of U.S. Patent Application is not submitted herewith pursuant to the waiver of 37 C.F.R § 1.98(a)(2)(iii) issued by the Office dated Sep. 21, 2004.).
Anonymous (Mar. 23, 2017). "Guideline on Clinical Development of Fixed Combination Medicinal Products," European Medicines Agency, 12 pages.
Baah, S. et al. (May 15, 2021). "Antibody-Drug Conjugates—A Tutorial Review," Molecules 26(2943):1-19.
Elmeliegy, M. et al. (2021, e-pub. Mar. 2, 2021). "Considerations on the Calculation of the Human Equivalent Dose from Toxicology Studies for Biologic Anticancer Agents," Clinical Pharmacokinetics 60:563-567.
Janeway, C.A. et al. (1997). Immunobiology, 3rd edition Garland Press, pp. 3.1-3.11, 14 pages.

(56) References Cited

OTHER PUBLICATIONS

Jin, Y. et al. (2022, e-pub. Jun. 24, 2021). "Stepping Forward in Antibody-Drug Conjugate Development," Pharmacology & Therapeutics 229:107917, 24 pages.

Tolcher, A.W. (2016). "Antibody Drug Conjugates: Lessons From 20 Years of Clinical Experience," Annal of Oncology 27:2168-2172.

Tolcher, A.W. (2022, e-pub. Jun. 20, 2022). "Antibody Drug Conjugates: The Dos and Don'ts in Clinical Development," Pharmacology & Therapeutics 240:108235, 8 pages.

Younes, A. et al. (Nov. 4, 2010). "Brentuximab Vedotin (SGN-35) for Relapsed CD30-Positive Lymphomas," New England Journal of Medicine 363(19):1812-1821.

Venetoclax (Jan. 31, 2011). Retrieved from the Internet <https://pubchem.ncbi.nlm.nih.gov/compound/Venetoclad>, last visited Aug. 11, 2023, 37 pages.

Bannerji, B. et al. (2021). "Abstract 7534, Polatuzumab Vedotin + Obinutuzumab + Venetoclax in Patients with Relapsed/Refractory (R/R) Follicular Lymphoma (FL): Primary Analysis of a Phase 1b/2 Trial," Journal of Clinical Oncology 2 pages.

Lasater, E.A. et al. (2023). "Targeting MCL-1 and BCL-2 with Polatuzumab Vedotin and Venetoclax Overcomes Treatment Resistance in R/R Non-Hodgkin Lymphoma: Results from Preclinical Models and a Phase 1b Study," Am. J. Hematol. 98:449-463.

Anonymous (May 19, 2020). "Non-Hodgkin Lymphoma Types," Retrieved from the Internet https://www.cancercenter.com/cancer-types/non-hodgkin-lymphoma/types, last visited May 19, 2020, 5 pages.

* cited by examiner

METHODS OF USING ANTI-CD79b IMMUNOCONJUGATES

CROSS REFERENCE TO RELATED APPLICATIONS

This application is a divisional of U.S. application Ser. No. 16/358,410, filed Mar. 19, 2019, which is a continuation of U.S. application Ser. No. 15/440,917, filed Feb. 23, 2017, now abandoned, which is a continuation of U.S. application Ser. No. 14/863,125, filed Sep. 23, 2015, now abandoned, which claims the benefit of U.S. Provisional Application Ser. No. 62/136,324, filed Mar. 20, 2015, U.S. Provisional Application Ser. No. 62/076,823, filed Nov. 7, 2014, and U.S. Provisional Application Ser. No. 62/054,257, filed Sep. 23, 2014, the contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392046010SEQLIST.TXT, date recorded: Jun. 23, 2020, size: 64 KB).

FIELD OF THE INVENTION

Provided herein are methods of treating B-cell proliferative disorders in particular Follicular Lymphoma and/or Diffuse Large B-Cell Lymphoma using immunoconjugates comprising anti-CD79b antibodies in combination with additional therapeutic agents.

BACKGROUND OF THE INVENTION

CD79b is the signaling component of the B-cell receptor which acts as a covalent heterodimer containing CD79a (i.e., Igα or mb-1) and CD79b (i.e., Igβ or B29). CD79b contains an extracellular immunoglobulin (Ig) domain, a transmembrane domain, and an intracellular signaling domain, an immunoreceptor tyrosine-based activation motif (ITAM) domain. CD79 is expressed on B-cells and, for example, in Non-Hodgkin's Lymphoma cells (NHLs) (Cabezudo et al., *Haematologica* 84:413-418 (1999); D'Arena et al., *Am. J. Hematol.* 64: 275-281 (2000); Olejniczak et al., *Immunol. Invest.* 35: 93-114 (2006)). CD79a and CD79b and sIg are all required for surface expression of the CD79 (Matsuuchi et al., *Curr. Opin. Immunol.* 13(3): 270-7)).

B-cell proliferative disorders are generally treated with some combination of surgery, radiation therapy and/or drug treatment. Accumulated empirical clinical experience, supported by animal models, supports the hypothesis that cytotoxic drugs may be more effective when given in combination to achieve additive or synergistic effects. However, a caveat to the hypothesis is that success requires the ability to combine drugs at their respective effective doses without unacceptable side-effects and avoiding possible pharmacokinetic interactions. Further, although it may seem reasonable to combine a targeted agent with the standard of care, clinical experience indicates that differences in administration regimens and the dosages of each agents has an effect on efficacy of the treatment. These factors have led to the clinical failure of many combinations. See, e.g., Al-Lazikani et al., *Nature Biotechnology* 30:679-692 (2012). There is a need in the art for new treatment regimens for treating B-cell proliferative disorders including treatments comprising agents that target CD79b (e.g., anti-CD79b immunoconjugates).

All references cited herein, including patent applications and publications, are incorporated by reference in their entirety.

SUMMARY

Provided herein are methods of treating a B-cell proliferative disorder in an individual comprising (a) an immunoconjugate comprising an antibody which binds CD79b linked to a cytotoxic agent and (b) an additional therapeutic agent.

In particular, provided herein are methods for treating a B-cell proliferative disorder in an individual comprising administering to the individual an effective amount of (a) an immunoconjugate comprising an anti-CD79b antibody linked to a cytotoxic agent and (b) an alkylating agent. In some embodiments, provided herein are methods for treating a B-cell proliferative disorder in an individual comprising administering to the individual an effective amount of (a) an immunoconjugate comprising an anti-CD79b antibody linked to a cytotoxic agent, (b) an anti-CD20 antibody, and (c) an alkylating agent.

In some embodiments of any of the methods, the anti-CD20 antibody is rituximab. In some embodiments, rituximab is administered at about 375 mg/m$^2$. In some embodiments of any of the methods, the anti-CD20 antibody is a humanized B-Ly1 antibody. In some embodiments, the humanized B-Ly1 antibody is obinutuzumab. In some embodiments, obinutuzumab is administered at about 1000 mg/m$^2$. In some embodiments of any of the methods, the anti-CD20 antibody is ofatumumab, ublituximab, and/or ibritumomab tiuxetan.

In some embodiments of any of the methods, the alkylating agent is 4-[5-[Bis(2-chloroethyl)amino]-1-methylbenzimidazol-2-yl]butanoic acid and salts thereof. In some embodiments of any of the methods, the alkylating agent is bendamustine. In some embodiments, bendamustine is administered at about 25-120 mg/m$^2$. In some embodiments, bendamustine is administered at about 90 mg/m$^2$.

In some embodiments of any of the methods, the cytotoxic agent is an antimitotic agent. In some embodiments, the antimitotic agent is an inhibitor of the polymerization of tubulin.

In some embodiments of any of the methods, the immunoconjugate has the formula Ab-(L-D)p, wherein: (a) Ab is the antibody which binds CD79b; (b) L is a linker; (c) D is the cytotoxic agent and the cytotoxic agent is selected from a maytansinoid or an auristatin; and (d) p ranges from 1-8.

In some embodiments of any of the methods, D is an auristatin. In some embodiments of any of the methods, D has formula DE

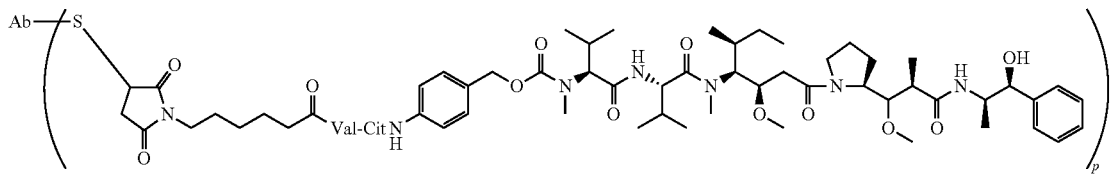

and wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl. In some embodiments of any of the methods, D is MMAE.

In some embodiments of any of the methods, the linker is cleavable by a protease. In some embodiments, the linker comprises a val-cit dipeptide or a Phe-homoLys dipeptide.

In some embodiments of any of the methods, the linker is acid-labile. In some embodiments, the linker comprises hydrazone.

In some embodiments of any of the methods, the formula is:

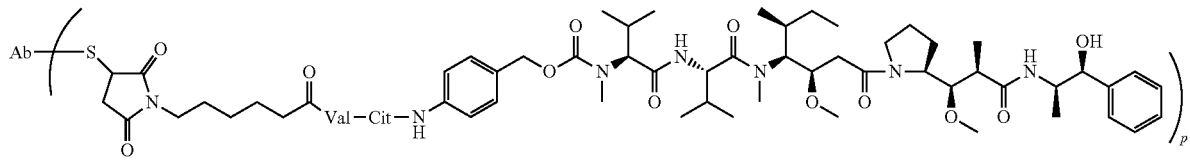

wherein S is a sulfur atom.

In some embodiments of any of the methods, p ranges from 2-5.

In some embodiments of any of the methods, the antibody is a monoclonal antibody. In some embodiments, the antibody is a human, humanized, or chimeric antibody.

In some embodiments of any of the methods, the antibody comprises (a) HVR-H1 comprising the amino acid sequence of SEQ ID NO:21; (b) HVR-H2 comprising the amino acid sequence of SEQ ID NO:22; (c) HVR-H3 comprising the amino acid sequence of SEQ ID NO:23; (d) HVR-L1 comprising the amino acid sequence of SEQ ID NO:24; (e) HVR-L2 comprising the amino acid sequence of SEQ ID NO:25; and (f) HVR-L3 comprising the amino acid sequence of SEQ ID NO:26.

In some embodiments of any of the methods, the antibody comprises (a) a VH comprising the amino acid sequence of SEQ ID NO:19 and (b) a VL sequence comprises the amino acid sequence of SEQ ID NO:20. In some embodiments of any of the methods, the antibody comprises (a) a heavy chain comprising the amino acid sequence of SEQ ID NO:36 and (b) a light chain comprising the amino acid sequence of SEQ ID NO:35.

In some embodiments of any of the methods, the antibody is a cysteine engineered antibody. In some embodiments, the antibody comprises an engineered cysteine at position 118 according to EU numbering convention of the heavy chain (A118C). In some embodiments, the antibody comprises an engineered cysteine at position 205 according to Kabat numbering convention of the light chain (V205C). In some embodiments of any of the methods, the cytotoxic agent is linked to the anti-CD79b antibody through the engineered cysteine (e.g., at position 118 according to EU numbering convention of the heavy chain and/or at position 205 according to Kabat numbering convention of the light chain). In some embodiments of any of the methods, the antibody comprises (a) a heavy chain comprising the amino acid sequence of SEQ ID NO:37 and (b) a light chain comprising the amino acid sequence of SEQ ID NO:35. In some embodiments of any of the methods, the antibody comprises (a) a heavy chain comprising the amino acid sequence of SEQ ID NO:36 and (b) a light chain comprising the amino acid sequence of SEQ ID NO:38.

In some embodiments of any of the methods, the B-cell proliferative disorder is cancer. In some embodiments, the B-cell proliferative disorder is lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma.

DETAILED DESCRIPTION

Figure 1:
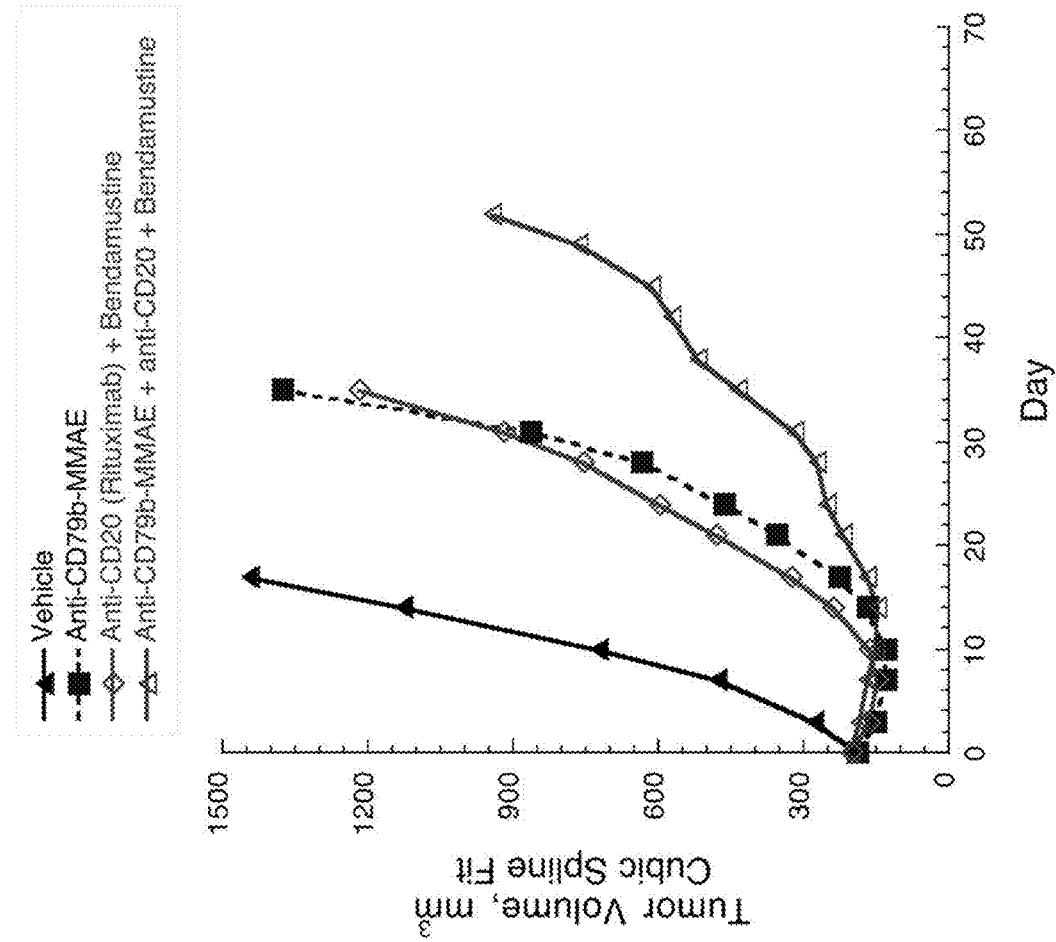
FIG. 1 shows change in tumor volume ($mm^3$) upon treatment of WSU-CLCL2 (Diffuse Large B-cell Lymphoma with (a) huMA79bv28-MC-vc-PAB-MMAE, (b) rituximab+bendamustine, and (c) huMA79bv28-MC-vc-PAB-MMAE+rituximab+bendamustine. huMA79bv28-MC-vc-PAB-MMAE: 2 mg/kg, iv, once on day 0; anti-CD20 (rituximab): 30 mg/kg, ip, once on day 0, and bendamustine: 30 mg/kg, iv, once on day 0.

Provided herein are methods of treating B-cell proliferative disorders such as indolent and aggressive NHL using combinations of immunoconjugates comprising an antibody which binds CD79b linked to a cytotoxic agent (i.e., anti-CD79b immunoconjugate) and additional therapeutic agents, in particular, in some embodiments, the immunoconjugates comprise an antimitotic agent such as an inhibitor of the polymerization of tubulin.

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

II. Definitions

The term "CD79b", as used herein, refers to any native CD79b from any vertebrate source, including mammals such as primates (e.g., humans, cynomolgus monkey (cyno)) and rodents (e.g., mice and rats), unless otherwise indicated. Human CD79b is also referred herein to as "Igβ," "B29," "DNA225786" or "PR036249." An exemplary CD79b sequence including the signal sequence is shown in SEQ ID NO:1. An exemplary CD79b sequence without the signal sequence is shown in SEQ ID NO:2. The term "CD79b" encompasses "full-length," unprocessed CD79b as well as any form of CD79b that results from processing in the cell. The term also encompasses naturally occurring variants of CD79b, e.g., splice variants, allelic variants and isoforms. The CD79b polypeptides described herein may be isolated from a variety of sources, such as from human tissue types or from another source, or prepared by recombinant or synthetic methods. A "native sequence CD79b polypeptide" comprises a polypeptide having the same amino acid sequence as the corresponding CD79b polypeptide derived from nature. Such native sequence CD79b polypeptides can be isolated from nature or can be produced by recombinant or synthetic means. The term "native sequence CD79b polypeptide" specifically encompasses naturally-occurring truncated or secreted forms of the specific CD79b polypeptide (e.g., an extracellular domain sequence), naturally-occurring variant forms (e.g., alternatively spliced forms) and naturally-occurring allelic variants of the polypeptide.

"CD20" as used herein refers to the human B-lymphocyte antigen CD20 (also known as CD20, B-lymphocyte surface antigen B1, Leu-16, Bp35, BM5, and LF5; the sequence is characterized by the SwissProt database entry P11836) is a hydrophobic transmembrane protein with a molecular weight of approximately 35 kD located on pre-B and mature B lymphocytes. (Valentine, M. A., et al., *J. Biol. Chem.* 264(19) (1989 11282-11287; Tedder, T. F., et al, *Proc. Nat. Acad. Sci. U.S.A.* 85 (1988) 208-12; Stamenkovic, I., et al., *J. Exp. Med.* 167 (1988) 1975-80; Einfeld, D. A. et al., *EMBO J.* 7 (1988) 711-7; Tedder, T. F., et al., *J. Immunol.* 142 (1989) 2560-8). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: Cell death/apoptosis induction, ADCC and CDC. Synonyms of CD20, as recognized in the art, include B-lymphocyte antigen CD20, B-lymphocyte surface antigen B1, Leu-16, Bp35, BM5, and LF5.

The term "expression of the CD20" antigen is intended to indicate a significant level of expression of the CD20 antigen in a cell, e.g., a T- or B-Cell. In one embodiment, patients to be treated according to the methods of this invention express significant levels of CD20 on a B-cell tumor or cancer. Patients having a "CD20 expressing cancer" can be determined by standard assays known in the art. e.g., CD20 antigen expression is measured using immunohistochemical (IHC) detection, FACS or via PCR-based detection of the corresponding mRNA.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "epitope" refers to the particular site on an antigen molecule to which an antibody binds.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "anti-CD79b antibody" or "an antibody that binds to CD79b" refers to an antibody that is capable of binding CD79b with sufficient affinity such that the antibody is useful as a diagnostic and/or therapeutic agent in targeting CD79b. Preferably, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 μM, ≤100 nM, ≤10 nM, ≤1 nM, or ≤0.1 nM. In certain embodiments, anti-CD79b antibody binds to an epitope of CD79b that is conserved among CD79b from different species.

The term "anti-CD20 antibody" according to the invention refers to an antibody that is capable of binding CD20 with sufficient affinity such that the antibody is useful as a diagnostic and/or therapeutic agent in targeting CD20. Preferably, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 μM, ≤100 nM, ≤10 nM, ≤1 nM, or ≤0.1 nM. In certain embodiments, anti-CD20 antibody binds to an epitope of CD20 that is conserved among CD20 from different species.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g., increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, and/or 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-1 axis binding antagonist and an anti-CD79b immunoconjugate (e.g., anti-CD79b-MC-vc-PAB-MMAE).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007). The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

"Isolated nucleic acid encoding an anti-CD79b antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, MD (1991) .) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B-cell receptor); and B-cell activation.

"CD79b polypeptide variant" means a CD79b polypeptide, preferably an active CD79b polypeptide, as defined herein having at least about 80% amino acid sequence identity with a full-length native sequence CD79b polypeptide sequence as disclosed herein, a CD79b polypeptide sequence lacking the signal peptide as disclosed herein, an extracellular domain of a CD79b polypeptide, with or without the signal peptide, as disclosed herein or any other fragment of a full-length CD79b polypeptide sequence as disclosed herein (such as those encoded by a nucleic acid that represents only a portion of the complete coding sequence for a full-length CD79b polypeptide). Such CD79b polypeptide variants include, for instance, CD79b polypeptides wherein one or more amino acid residues are added, or deleted, at the N- or C-terminus of the full-length native amino acid sequence. Ordinarily, a CD79b polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence CD79b polypeptide sequence as disclosed herein, a CD79b polypeptide sequence lacking the signal peptide as disclosed herein, an extracellular domain of a CD79b polypeptide, with or without the signal peptide, as disclosed herein or any other specifically defined fragment of a full-length CD79b polypeptide sequence as disclosed herein. Ordinarily, CD79b variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, CD79b variant polypeptides will have no more than one conservative amino acid substitution as compared to the native CD79b polypeptide sequence, alternatively no more than 2, 3, 4, 5, 6, 7, 8, 9, or 10 conservative amino acid substitution as compared to the native CD79b polypeptide sequence.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{21}$, $I^{131}$, $I^{125}$, $Y^{90}$, $Re^{186}$, $Re^{188}$, $Sm^{153}$, $B^{212}$, $P^{32}$, $Pb^{212}$ and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The terms "cancer" and "cancerous" refer to or describe the physiological condition in mammals that is typically characterized by unregulated cell growth. Examples of cancer include but are not limited to, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglubulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "effective amount" of an agent, e.g., a pharmaceutical formulation, refers to an amount effective, at dosages and for periods of time necessary, to achieve the desired therapeutic or prophylactic result.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, reduction of free light chain, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, the antibodies described herein are used to delay development of a disease or to slow the progression of a disease.

The term "CD79b-positive cancer" refers to a cancer comprising cells that express CD79b on their surface. In some embodiments, expression of CD79b on the cell surface is determined, for example, using antibodies to CD79b in a method such as immunohistochemistry, FACS, etc. Alternatively, CD79b mRNA expression is considered to correlate to CD79b expression on the cell surface and can be determined by a method selected from in situ hybridization and RT-PCR (including quantitative RT-PCR).

As used herein, "in conjunction with" refers to administration of one treatment modality in addition to another treatment modality. As such, "in conjunction with" refers to administration of one treatment modality before, during, or after administration of the other treatment modality to the individual.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitinib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, everolimus, sotrataurin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Additional examples include of chemotherapeutic agents include bendamustine (TREANDA®), ibrutinib, lenalidomide, and/or idelalisib (GS-1101).

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine.

In some embodiments, the chemotherapeutic agent includes topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

Chemotherapetuic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ublituximab, ofatumumab, ibritumomab tiuxetan, pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL 10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

The term "package insert" is used to refer to instructions customarily included in commercial packages of therapeutic products, that contain information about the indications, usage, dosage, administration, combination therapy, contraindications and/or warnings concerning the use of such therapeutic products.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_8$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

A "C$_1$-C$_{10}$ alkylene" is a straight chain, saturated hydrocarbon group of the formula —(CH$_2$)$_{1-10}$—. Examples of a C$_1$-C$_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

A "C$_5$-C$_{20}$ aryl" is an aryl group with 5 to 20 carbon atoms in the carbocyclic aromatic rings. Examples of C$_5$-C$_{20}$ aryl groups include, but are not limited to, phenyl, naphthyl and anthracenyl. A C$_5$-C$_{20}$ aryl group can be substituted or unsubstituted as described above for aryl groups. A "C$_5$-C$_{14}$ aryl" is an aryl group with 5 to 14 carbon atoms in the carbocyclic aromatic rings. Examples of C$_5$-C$_{14}$ aryl groups include, but are not limited to, phenyl, naphthyl and anthracenyl. A C$_5$-C$_{14}$ aryl group can be substituted or unsubstituted as described above for aryl groups.

An "arylene" is an aryl group which has two covalent bonds and can be in the ortho, meta, or para configurations as shown in the following structures:

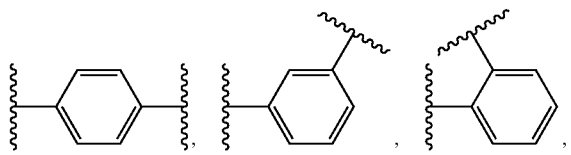

in which the phenyl group can be unsubstituted or substituted with up to four groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_{20}$R, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, C$_1$, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g., nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-*Hill Book Company*, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting of" and/or "consisting essentially of" aspects and variations.

A. Methods of Use

Provided herein are methods of treating a B-cell proliferative disorder in an individual comprising (a) an immunoconjugate comprising an antibody which binds CD79b linked to a cytotoxic agent and (b) an additional therapeutic agent. In some embodiments, the additional therapeutic agent is a chemotherapeutic agent. In some embodiments, the additional therapeutic agent is cytotoxic agent.

Provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate and (b) an alkylating agent. In particular, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) an alkylating agent. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the alkylating agent is 4-[5-[Bis(2-chloroethyl)amino]-1-methylbenzimidazol-2-yl]butanoic acid and salts thereof. In some embodiments, the alkylating agent is bendamustine. In some embodiments, the anti-CD79b immunoconjugate is huMA79bv28-MC-vc-PAB-MMAE.

In addition, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate) and (b) a BCL-2 inhibitor. In particular, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) a BCL-2 inhibitor. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the BCL-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and salts thereof. In some embodiments, the BCL-2 inhibitor is venetoclax (CAS #: 1257044-40-8). In some embodiments, the anti-CD79b immunoconjugate is huMA79bv28-MC-vc-PAB-MMAE.

Also provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate) and (b) a phosphoinositide 3-kinase (PI3K) inhibitor. For example, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) a phosphoinositide 3-kinase (PI3K) inhibitor. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the PI3K inhibitor inhibits delta isoform PI3K (i.e., P1106). In some embodiments, the PI3K inhibitor is 5-Fluoro-3-phenyl-2-[(1S)-1-(7H-purin-6-ylamino)propyl]-4(3H)-quinazolinone and salts thereof. In some embodiments, the PI3K inhibitor is idelalisib (CAS #: 870281-82-6). In some embodiments, the PI3K inhibitor inhibits alpha and delta isoforms of PI3K. In some embodiments, the PI3K inhibitor is 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide and salts thereof. In some embodiments, the anti-CD79b immunoconjugate is huMA79bv28-MC-vc-PAB-MMAE.

Also provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate) and (b) a Bruton's tyrosine kinase (BTK) inhibitor. In some embodiments, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) a Bruton's tyrosine kinase (BTK) inhibitor. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In some embodiments, the BTK inhibitor is ibrutinib (CAS #: 936563-96-1). In some embodiments, the anti-CD79b immunoconjugate is huMA79bv28-MC-vc-PAB-MMAE.

Provided herein are also methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate) and (b) thalidomide or a derivative thereof. For example, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) thalidomide or a derivative thereof. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the thalidomide or a derivative thereof is (RS)-3-(4-Amino-1-oxo 1,3-dihydro-2H-isoindol-2-yl)piperidine-2,6-dione and salts thereof. In some embodiments, the thalidomide or a derivative thereof is lendalidomide (CAS #: 191732-72-6). In some embodiments, the anti-CD79b immunoconjugate is huMA79bv28-MC-vc-PAB-MMAE.

Provided herein are also methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate) and (b) a PD-1 axis binding antagonist. For example, provided herein are methods for treating a B-cell proliferative disorder in an individual comprising administering to the individual an effective amount of (a) an immunoconjugate comprising an anti-CD79b antibody linked to a cytotoxic agent (i.e., anti-CD79b immunoconjugate), (b) an anti-CD20 antibody, and (c) a PD-1 axis binding agent. In some embodiments, the anti-CD20 antibody is rituximab. In some embodiments, the anti-CD20 antibody is a humanized B-Ly1 antibody. In some embodiments, the humanized B-Ly1 antibody is obinituzumab. In some embodiments, the anti-CD20 antibody is ofatumumab, ublituximab, and/or ibritumomab tiuxetan. In some embodiments, the anti-CD79b immunoconjugate is huMA79bv28-MC-vc-PAB-MMAE. In some embodiments, the PD-1 axis binding antagonist is selected from the group consisting of a PD-1 binding antagonist, a PD-L1 binding antagonist and a PD-L2 binding antagonist. PD-1 (programmed death 1) is also referred to in the art as "programmed cell death 1", PDCD1, CD279 and SLEB2. PD-L1 (programmed death ligand 1) is also referred to in the art as "programmed cell death 1 ligand 1", PDCD1LG1, CD274, B7-H, and PDL1. PD-L1 (programmed death ligand 1), also known as PDL1, B7-H1, B7-4, CD274, and B7-H, is a transmembrane protein, and its interaction with PD-1 inhibits T-cell activation and cytokine production. PD-L2 (programmed death ligand 2) is also referred to in the art as "programmed cell death 1 ligand 2", PDCD1LG2, CD273, B7-DC, Btdc, and PDL2. In some embodiments, PD-1, PD-L1, and PD-L2 are human PD-1, PD-L1 and PD-L2. In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the PD-1 binding antagonist is selected from the group consisting of MDX-1106 (nivolumab), MK-3475 (pembrolizumab, lambrolizumab), CT-011 (pidilizumab), and AMP-224. Nivolumab, also known as MDX-1106-04, MDX-1106, ONO-4538, BMS-936558, and OPDIVO®, is an anti-PD-1 antibody described in WO2006/121168. In some embodiments, the anti-PD-1 antibody is Nivolumab (CAS Registry Number: 946414-94-4). Pembrolizumab, also known as MK-3475, Merck 3475, lambrolizumab, KEYTRUDA®, and SCH-900475, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the PD-L1 binding antagonist is selected from the group consisting of: YW243.55.S70, MPDL3280A, MDX-1105, and MEDI4736. Antibody YW243.55.S70 is an anti-PD-L1 described in WO 2010/077634. MDX-1105, also known as BMS-936559, is an anti-PD-L1 antibody described in WO2007/005874. MEDI4736, is an anti-PD-L1 monoclonal antibody described in WO2011/066389 and US2013/034559. Examples of anti-PDL1 antibodies that can be used in the methods described herein are described in PCT patent application WO 2010/077634 A1 and U.S. Pat. No. 8,217,149, which are incorporated herein by reference. In some embodiments, the PD-1 axis binding antagonist is an antibody. In some embodiments, the PD-1 axis binding antagonist is a PD-L2 binding antagonist. In some embodiments, the PD-L2 binding antagonist is an antibody. In some embodiments, the PD-L2 binding antagonist is an immunoadhesin. In some embodiments, the combination method enhances inhibition of tumor growth, increased response rates and/or durable responses.

In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, method further comprises administration in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3, B7-H3, B7-H4, IDO, TIGIT, MICA/B, or arginase. In some embodiments, method further comprises administration in conjunction with a treatment comprising adoptive transfer of a T cell (e.g., a cytotoxic T cell or CTL) expressing a chimeric antigen receptor (CAR).

In some embodiments of any of the methods, the cytotoxic agent is an antimitotic agent. Antimitotic agents are known in the art as well as inhibitors of the polymerization of tubulin. See e.g., Perez, *Mol. Cancer Ther.* 8:2086-2095 (2009), Doronina et al., *Nat. Biotechnol.* 21:778-784 (2003), and Doronina et al., *Bioconjug Chem.* 17:114-124 (2006). In some embodiments, the antimitotic agent includes, but is not limited to, a maytansinoid, a dolastatin, an auristatin, and/or analogs and/or derivatives thereof. In some embodiments, the antimitotic agent is an auristatin and/or analog and/or derivative thereof. In some embodiments, the auristatin and/or analog and/or derivative thereof is MMAE. In some embodiments, the auristatin and/or analog and/or derivative thereof is MMAF.

In a further aspect, the invention provides for the use of an anti-CD79b immunoconjugate in the manufacture or preparation of a medicament for use in combination with an additional therapeutic agent. For example, provided herein is the use of an anti-CD79b immunoconjugate in the manufacture or preparation of a medicament for use in combination with an anti-CD20 antibody and an alkylating agent (e.g., bendamustine). In one such embodiment, the method further comprises administering to the individual an effective amount of at least one additional therapeutic agent.

An "individual" according to any of the above embodiments may be a human.

In one embodiment, B-cell proliferative disease includes, but is not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma, and/or j) Hodgkin's disease.

In some embodiments of any of the methods, the B-cell proliferative disorder is cancer. In some embodiments, the B-cell proliferative disorder is lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma (DLBCL). In some embodiments, the DLBCL is activated B cell DLBCL (ABC DLBCL). In some embodiments, the DLBCL is germinal center B-cell like DLBCL (GCB DLBCL). In some embodiment, the DLBCL is BCL2 positive (e.g., positive for BCL2 gene rearrangement, t(14; 18)(q32;q21)). In some embodiments, the DLBCL is BCL2 negative (e.g., negative for BCL2 gene rearrangement, t(14; 18)(q32;q21)).

In some embodiments of any of the methods, the B-cell proliferative disorder is a histologically confirmed FL (Grade 1, 2, or 3a) or DLBCL. In some embodiments, the individual has received at least one prior therapy for FL or DLBCL. In some embodiments, the patient has received prior bendamustine and the duration must have been >1 year (for patients who have relapse disease after a prior regimen). In some embodiments, at least one bi-dimensionally measurable lesion on imaging scan defined as >1.5 cm in its longest dimension; confirmed availability of archival or freshly collected tumor tissue meeting protocol-defined specifications prior to study enrollment; Life expectancy of at least 24 weeks; Eastern Cooperative Oncology Group (ECOG) Performance Status of 0, 1, or 2; adequate hematological function; and/or, for women of childbearing potential, a negative serum pregnancy test result within 7 days prior to commencement of dosing.

In some embodiments, the individual does not have a history of severe allergic or anaphylactic reactions to humanized or murine monoclonal antibodies (MAbs, or recombinant antibody-related fusion proteins) or known sensitivity or allergy to murine products, contraindication to bendamustine, rituximab, or obinutuzumab. In some embodiments, the individual does not have a history of sensitivity to mannitol, prior use of any MAb, radioimmunoconjugate, or antibody-drug conjugate (ADC) within 4 weeks before Cycle 1 Day 1, treatment with radiotherapy, chemotherapy, immunotherapy, immunosuppressive therapy, and/or any investigational agent for the purposes of treating cancer within 2 weeks prior to Cycle 1 Day 1, ongoing corticosteroid use >30 mg/day prednisone or equivalent, for purposes other than lymphoma symptom control, completion of autologous SCT within 100 days prior to Cycle 1 Day 1, prior allogeneic SCT, eligibility for autologous SCT (patients with relapsed/refractory DLBCL), Grade 3b FL, history of transformation of indolent disease to DLBCL, primary CNS lymphoma, current Grade >1 peripheral neuropathy, evidence of significant, uncontrolled concomitant diseases that could affect compliance with the protocol or interpretation of results, including significant cardiovascular disease (such as New York Heart Association Class III or IV cardiac disease, myocardial infarction within the last 6 months, unstable arrhythmias, or unstable angina) or significant pulmonary disease (including obstructive pulmonary disease and history of bronchospasm), known active bacterial, viral, fungal, mycobacterial, parasitic, or other infection (excluding fungal infections of nail beds) at study enrollment or any major episode of infection requiring treatment with intravenous (IV) antibiotics or hospitalization within 4 weeks prior to Cycle 1 Day 1, patients with suspected or latent tuberculosis, positive test results for chronic hepatitis B virus (HBV) infection or for hepatitis C virus (HCV) antibody, known infection with HIV or human T-cell leukemia virus 1 (HTLV-1) virus, women who are pregnant or lactating or who intend to become pregnant within a year of the last dose of rituximab or obinutuzumab, and/or evidence of laboratory abnormalities in standard renal, hepatic or coagulation function tests.

In some embodiments of any of the methods, the B-cell proliferative disorder is a relapsed or refractory B-cell proliferative disorder. In some embodiments, relapsed or refractory B-cell proliferative disorder as used herein includes patients who have received at least 1 prior chemotherapy containing treatment regimen. In some embodiments, relapsed patients generally have developed progressive disease following a response to the prior chemotherapy-containing treatment regimen. In some embodiments, refractory patients have generally failed to respond or relapsed within 6 months to the last prior chemotherapy-containing regimen. In some embodiments, relapsed/refractory follicular lymphoma (FL) patients who have relapsed to prior regimen(s) after having a documented history of response (complete response [CR], CR unconfirmed [CRu], or partial response [PR]) of >/=6 months in duration from completion of regimen(s); refractory to any prior regimen, defined as no response to the prior therapy, or progression within 6 months of completion of the last dose of therapy. In some embodiments, relapsed/refractory DLBCL patients are patients who are ineligible for second-line stem cell transplant (SCT), with progressive disease or no response (stable disease [SD])<6 months from start of initial therapy; patients who are ineligible for second-line SCT, with disease relapse after initial response of >/=6 months from start of initial therapy; patients who are ineligible for third-line (or beyond) SCT, with progressive disease or no response (SD)<6 months from start of prior therapy; patients who are ineligible for third-line (or beyond) SCT with disease relapse after initial response of >/=6 months from start of prior therapy.

In some embodiments, the individual having a B-cell proliferative disorder is previously untreated. In some embodiments, previously untreated as used herein includes patients diagnosed with a B-cell proliferative disease, but who have, in general, received no prior chemotherapy or immunotherapy. Patients with a history of emergency, loco-regional radiotherapy (e.g., for relief of compressive signs or symptoms) or corticosteroids can still be considered previously untreated.

An immunoconjugate provided herein (and any additional therapeutic agent) for use in any of the therapeutic methods described herein can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

In some embodiments of any of the methods, if the administration is intravenous the initial infusion time for the anti-CD79b immunoconjugate or the additional therapeutic agent may be longer than subsequent infusion times, for instance approximately 90 minutes for the initial infusion, and approximately 30 minutes for subsequent infusions (if the initial infusion is well tolerated).

The terms "co-administration" or "co-administering" refer to the administration of the anti-CD79b immunoconjugate and the additional therapeutic agent as two separate formulations (or as one single formulation). The co-administration can be simultaneous or sequential in either order, wherein preferably there is a time period while both (or all) active agents simultaneously exert their biological activities. The anti-CD79b immunoconjugate and the additional therapeutic agent are co-administered either simultaneously or sequentially. In some embodiments, when both therapeutic agents are co-administered sequentially the dose is administered either on the same day in two separate administrations, or one of the agents is administered on day 1 and the second is co-administered on day 2 to day 7, preferably on day 2 to 4. Thus in one embodiment the term "sequentially" means within 7 days after the dose of the first component, preferably within 4 days after the dose of the first component; and the term "simultaneously" means at the same time. The term "co-administration" with respect to the maintenance doses of said the anti-CD79b immunoconjugate and the additional therapeutic agent means that the maintenance doses can be either co-administered simultaneously, if the treatment cycle is appropriate for both drugs, e.g., every week. Or anti-CD79b immunoconjugate is e.g., administered e.g., every first to third day and the additional therapeutic is administered every week. Or the maintenance doses are co-administered sequentially, either within one or within several days.

Anti-CD79b immunoconjugates and additional therapeutic agents provided herein for use in any of the therapeutic methods described herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The immunoconjugate need not be, but is optionally formulated with one or more agents currently used to prevent or treat the disorder in question.

The amount of co-administration of the anti-CD79b immunoconjugate and the additional therapeutic agent and the timing of co-administration will depend on the type (species, gender, age, weight, etc.) and condition of the patient being treated and the severity of the disease or condition being treated. The anti-CD79b immunoconjugate and the additional therapeutic agent are suitably co-administered to the patient at one time or over a series of treatments e.g., on the same day or on the day after.

In some embodiments of any of the methods, the dosage of anti-CD79b immunoconjugate (such as huMA79bv28-MC-vc-PAB-MMAE) is between about any of 1.4-5 mg/kg, 1.8-4 mg/kg, 1.8-3.2 mg/kg, and/or 1.8-2.4 mg/kg. In some embodiments of any of the methods, the dosage of anti-CD79 immunoconjugate is about any of 1.4, 1.8, 2.0, 2.2, 2.4, 2.8, 3.2, 3.6, 4.0, 4.4, and/or 4.8 mg/kg. In some embodiments, the dosage of anti-CD79b immunoconjugate is about 1.8 mg/kg. In some embodiments, the dosage of anti-CD79b immunoconjugate is about 2.4 mg/kg. In some embodiments, the dosage of anti-CD79b immunoconjugate is about 3.2 mg/kg. In some embodiments, the dosage of anti-CD79b immunoconjugate is about 3.6 mg/kg. In some embodiments of any of the methods, the anti-CD79b immunoconjugate is administered q3wk. In some embodiments, the anti-CD79b immunoconjugate is administered via intravenous infusion. The dosage administered via infusion is in the range of about 1 µg/m2 to about 10,000 µg/m2 per dose, generally one dose per week for a total of one, two, three or four doses. Alternatively, the dosage range is of about 1 µg/m2 to about 1000 µg/m2, about 1 µg/m2 to about 800 µg/m2, about 1 µg/m2 to about 600 µg/m2, about 1 µg/m2 to about 400 µg/m2, about 10 µg/m2 to about 500 µg/m2, about 10 µg/m2 to about 300 µg/m2, about 10 µg/m2 to about 200 µg/m2, and about 1 µg/m2 to about 200 µg/m2. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the lymphoma, leukemia being treated. Administration may continue after remission or relief of symptoms is achieved where such remission or relief is prolonged by such continued administration.

In some embodiments of any of the methods, the dosage of the anti-CD20 antibody is between about 300-1600 mg/m² and/or 300-2000 mg In some embodiments of any of the methods, the dosage of the anti-CD20 antibody is about any of 300, 375, 600, 1000, or 1250 mg/m² and/or 300, 1000, or 2000 mg. In some embodiments, the anti-CD20 antibody is rituximab and the dosage administered is 375 mg/m². In some embodiments, the anti-CD20 antibody is obinutuzumab and the dosage administered is 1000 mg/m². In some embodiments, the anti-CD20 antibody is administered q3wk. In some embodiments, the dosage of said afucosylated anti-CD20 antibody (preferably the afucosylated humanized B-Ly1 antibody) may be 800 to 1600 mg (in one embodiment 800 to 1200 mg) on day 1, 8, 15 of a 3- to 6-weeks-dosage-cycle and then in a dosage of 400 to 1200 (in one embodiment 800 to 1200 mg) on day 1 of up to nine 3- to 4-weeks-dosage-cycles. In some embodiments, the dose is a flat dose 1000 mg in a three-weeks-dosage schedule, with the possibility of an additional cycle of a flat dose of 1000 mg in the second week.

Exemplary dosing regimens for the combination therapy of anti-CD79b immunoconjugates (such as huMA79bv28-MC-vc-PAB-MMAE) and other agents include, but are not limited to, anti-CD79 immunoconjugate (such as huMA79bv28-MC-vc-PAB-MMAE) administered at about 1.4-5 mg/kg q3wk, plus 375 mg/m² q3wk rituximab, and 25-120 mg/m² bendamustine (e.g., bendamustine hydrochloride) d1 and 2 of q3wk daily. In some embodiments, the anti-CD79 immunoconjugate is administered at about any of 1.8 mg/kg, 2.0 mg/kg, 2.2 mg/kg, 2.4 mg/kg, 3.2 mg/kg, or 4.0 mg/kg. In some embodiments, the anti-CD79b immunoconjugate is administered at about 1.8 mg/kg. In some embodiments, the anti-CD79b immunoconjugate is administered at about 2.4 mg/kg. In some embodiments, bendamustine is administered at about 90 mg/m².

Another exemplary dosage regime for the combination therapy of anti-CD79b immunoconjugates (such as huMA79bv28-MC-vc-PAB-MMAE) and other agents include, but are not limited to, anti-CD79 immunoconjugate (such as huMA79bv28-MC-vc-PAB-MMAE) administered 1.4-5 mg/kg q3wk, plus 1000 mg/m² q3wk obinutuzumab, and 25-120 mg/m² bendamustine d1 and 2 of q3wk daily. In some embodiments, the anti-CD79 immunoconjugate is administered at about any of 1.8 mg/kg, 2.0 mg/kg, 2.2 mg/kg, 2.4 mg/kg, 3.2 mg/kg, or 4.0 mg/kg. In some embodiments, the anti-CD79b immunoconjugate is administered at about 1.8 mg/kg. In some embodiments, the anti-CD79b immunoconjugate is administered at about 2.4 mg/kg. In some embodiments, bendamustine is administered at about 90 mg/m².

B. Agents for Use in the Methods Described Herein

Provided herein are anti-CD79b immunoconjugates and additional therapeutic agents for use in the methods described herein. In some embodiments, the additional therapeutic agent is an antibody. In some embodiments, the additional therapeutic agent is a small molecule. In some embodiments, the additional therapeutic agent is an anti-CD20 antibody and bendamustine.

1. Anti-CD79b Immunoconjugates Comprising Anti-CD79b Antibodies and

OTHER EMBODIMENTS

Provided herein are anti-CD79b antibodies for the anti-CD79b immunoconjugates for use in the methods described herein comprising anti-CD79b immunoconjugates and an additional therapeutic agent.

In some embodiments, the methods herein provide an immunoconjugate comprising an anti-CD79b antibody comprising at least one, two, three, four, five, or six HVRs selected from (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26. In some such embodiments, the immunoconjugate comprises at least one of: (i) HVR-H3 comprising the amino acid sequence of SEQ ID NO: 23, and/or (ii) HVR-L1 comprising an amino acid sequence of SEQ ID NO: 24.

In some embodiments, provided herein for use in the methods are immunoconjugates comprising an anti-CD79b antibody comprising at least one, two, three, four, five, or six HVRs selected from (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26. In some such embodiments, the immunoconjugate comprises at least one of: (i) HVR-H3 comprising the amino acid sequence of SEQ ID NO: 23, and/or (ii) HVR-L1 comprising the amino acid sequence of SEQ ID NO:24. In one aspect, provided herein are immunoconjugates comprising an anti-CD79b immunoconjugate comprising at least one, at least two, or all three VH HVR sequences selected from (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 23. In some embodiments, the immunoconjugate comprises HVR-H3 comprising the amino acid sequence of SEQ ID NO: 23. In another embodiment, the immunoconjugate comprises HVR-H3 comprising the amino acid sequence of SEQ ID NO: 23 and HVR-L3 comprising the amino acid sequence of SEQ ID NO: 26. In a further embodiment, the immunoconjugate comprises HVR-H3 comprising the amino acid sequence of SEQ ID NO: 23, HVR-L3 comprising the amino acid sequence of SEQ ID NO: 26, and HVR-H2 comprising the amino acid sequence of SEQ ID NO: 22. In a further embodiment, the immunoconjugate comprises (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 23.

In another aspect, the immunoconjugate comprises an anti-CD79b antibody comprising at least one, at least two, or all three VL HVR sequences selected from (a) HVR-L1 comprising an amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In another aspect, provided herein are immunoconjugates comprising at least one, at least two, or all three VL HVR sequences selected from (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In one embodiment, the immunoconjugate comprises (a) HVR-L1 comprising an amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In some embodiments, the immunoconjugate comprises an HVR-L1 comprising the amino acid sequence of SEQ ID NO: 24. In some embodiments, the immunoconjugate comprises an HVR-L1 comprising the amino acid sequence of SEQ ID NO: 24. In some embodiments, the immunoconjugate comprises (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26.

In another aspect, the immunoconjugate comprises an anti-CD79b antibody comprising (a) a VH domain comprising at least one, at least two, or all three VH HVR sequences selected from (i) HVR-H1 comprising the amino acid sequence of SEQ ID NO: 21, (ii) HVR-H2 comprising the amino acid sequence of SEQ ID NO: 22, and (iii) HVR-H3 comprising an amino acid sequence selected from SEQ ID NO:23; and (b) a VL domain comprising at least one, at least two, or all three VL HVR sequences selected from (i) HVR-L1 comprising an amino acid sequence of SEQ ID NO: 24, (ii) HVR-L2 comprising the amino acid sequence of SEQ ID NO: 25, and (iii) HVR-L3 comprising the amino acid sequence of SEQ ID NO: 26. In some such embodiments, the immunoconjugate comprises at least one of: (i) HVR-H3 comprising the amino acid sequence of SEQ ID NO: 23, and/or (ii) HVR-L1 comprising the amino acid sequence of SEQ ID NO: 24.

In another aspect, the provided herein are immunoconjugates comprising (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26. In some such embodiments, the immunoconjugate comprises at least one of: HVR-H3 comprising the amino acid sequence of SEQ ID NO: 23 and/or HVR-L1 comprising an amino acid sequence of SEQ ID NO: 24. In another aspect, provided are immunoconjugates comprising (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In any of the above embodiments, the anti-CD79b immunoconjugates comprises a humanized anti-CD79b antibody. In one embodiment, an anti-CD79b antibody comprises HVRs as in any of the above embodiments, and further comprises a human acceptor framework, e.g., a human immunoglobulin framework or a human consensus framework. In certain embodiments, the human acceptor framework is the human VL kappa 1 ($VL_{KI}$) framework and/or the VH framework $VH_{III}$. In some embodiments, a humanized anti-CD79b antibody comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26. In some embodiments, a humanized anti-CD79b antibody comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In another aspect, an anti-CD79b immunoconjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 19. In certain embodiments, a VH sequence having at least 90%, 91%, 92%, 93%, 94%, 95%, 96%, 97%, 98%, or 99% identity to the amino acid sequence of SEQ ID NO: 19 contains substitutions (e.g., conservative substitutions), insertions, or deletions relative to the reference sequence, but an anti-CD79b immunoconjugate comprising that sequence retains the ability to bind to CD79b. In certain embodiments, a total of 1 to 10 amino acids have been substituted, inserted and/or deleted in SEQ ID NO: 19. In certain embodiments, a total of 1 to 5 amino acids have been substituted, inserted and/or deleted in SEQ ID NO: 19. In certain embodiments, substitutions, insertions, or deletions occur in regions outside the HVRs (i.e., in the FRs).

Optionally, the anti-CD79b immunoconjugate comprises the VH sequence of any one of SEQ ID NO: 19, including post-translational modifications of that sequence. In some embodiments, the anti-CD79b immunoconjugate comprises the VH sequence of SEQ ID NO: 19, including post-translational modifications of that sequence. In a particular embodiment, the VH comprises one, two or three HVRs selected from: (a) HVR-H1 comprising the amino acid sequence of SEQ ID NO: 21, (b) HVR-H2 comprising the amino acid sequence of SEQ ID NO: 22, and (c) HVR-H3 comprising the amino acid sequence of SEQ ID NO: 17 or SEQ ID NO: 23.

In some embodiments, an anti-CD79b immunoconjugate comprises a light chain variable domain (VL) having at least 90%, 91%, 92%, 93%, 94%, 95%, 96%, 97%, 98%, 99%, or 100% sequence identity to the amino acid sequence of SEQ ID NO: 20. In certain embodiments, a VL sequence having at least 90%, 91%, 92%, 93%, 94%, 95%, 96%, 97%, 98%, or 99% identity to the amino acid sequence of SEQ ID NO: 20 contains substitutions (e.g., conservative substitutions), insertions, or deletions relative to the reference sequence, but an anti-CD79b immunoconjugate comprising that sequence retains the ability to bind to CD79b. In certain embodiments, a total of 1 to 10 amino acids have been substituted, inserted and/or deleted in SEQ ID NO: 20. In certain embodiments, a total of 1 to 5 amino acids have been substituted, inserted and/or deleted in SEQ ID NO: 20. In certain embodiments, the substitutions, insertions, or deletions occur in regions outside the HVRs (i.e., in the FRs). Optionally, the anti-CD79b immunoconjugate comprises the VL sequence of any one of SEQ ID NO: 20, including post-translational modifications of that sequence. In some embodiments, the anti-CD79b immunoconjugate comprises the VL sequence of SEQ ID NO: 20, including post-translational modifications of that sequence. In a particular embodiment, the VL comprises one, two or three HVRs selected from (a) HVR-L1 comprising an amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In some embodiments, the VL comprises one, two or three HVRs selected from (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26.

In another aspect, an anti-CD79b immunoconjugate comprises a VH as in any of the embodiments provided above, and a VL as in any of the embodiments provided above. In some embodiments, the antibody comprises the VH and VL sequences in SEQ ID NO: 19 and SEQ ID NO: 20, respectively, including post-translational modifications of those sequences.

In a further aspect, provided herein are anti-CD79b immunoconjugates that binds to the same epitope as an anti-CD79b antibody provided herein. For example, in certain embodiments, immunoconjugate is provided that binds to the same epitope as an anti-CD79b antibody comprising a VH sequence of SEQ ID NO: 19 and a VL sequence of SEQ ID NO: 20.

In a further aspect of the invention, an anti-CD79b immunoconjugate according to any of the above embodiments comprises a monoclonal antibody, including a chimeric, humanized or human antibody. In one embodiment, an anti-CD79b immunoconjugate comprises an antibody fragment, e.g., a Fv, Fab, Fab', scFv, diabody, or F(ab')$_2$ fragment. In another embodiment, the immunoconjugate comprises a substantially full length antibody, e.g., an IgG1 antibody or other antibody class or isotype as defined herein.

2. Anti-CD20 Antibodies and Other Embodiments

Provided herein are anti-CD20 antibodies for use in the methods described herein comprising anti-CD79b immunoconjugates and an additional therapeutic agent.

Depending on binding properties and biological activities of anti-CD20 antibodies to the CD20 antigen, two types of anti-CD20 antibodies (type I and type II anti-CD20 antibodies) can be distinguished according to Cragg, M. S., et al., *Blood* 103 (2004) 2738-2743; and Cragg, M. S., et al., *Blood* 101 (2003) 1045-1052, see Table 1.

TABLE 1

| Properties of type I and type II anti-CD20 antibodies | |
|---|---|
| Type I anti-CD20 antibodies | type II anti-CD20 antibodies |
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

Examples of type I anti-CD20 antibodies include e.g., rituximab, HI47 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312). In some embodiments, the anti-CD20 antibody is rituximab antibody. In some embodiments, the rituximab antibody (reference antibody; example of a type I anti-CD20 antibody) is a genetically engineered chimeric human gamma 1 murine constant domain containing monoclonal antibody directed against the human CD20 antigen. However, this antibody is not glycoengineered and not afucosylated and thus has an amount of fucose of at least 85%. This chimeric antibody contains human gamma 1 constant domains and is identified by the name "C2B8" in U.S. Pat. No. 5,736,137 (Andersen, et. al.) issued on Apr. 17, 1998, assigned to IDEC Pharmaceuticals Corporation. Rituximab is approved for the treatment of patients with relapsed or refracting low-grade or follicular, CD20 positive, B-cell non-Hodgkin's lymphoma. In vitro mechanism of action studies have shown that rituximab exhibits human complement-dependent cytotoxicity (CDC) (Reff, M. E., et. al, *Blood* 83(2) (1994) 435-445). Additionally, it exhibits activity in assays that measure antibody-dependent cellular cytotoxicity (ADCC).

In some embodiments, the anti-CD20 antibodies are an afucosylated anti-CD20 antibody.

Examples of type II anti-CD20 antibodies include e.g., humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype. In one embodiment said type II anti-CD20 antibody, e.g., a GA101 antibody, has increased antibody dependent cellular cytotoxicity (ADCC). In some embodiments, the type II anti-CD20 antibodies, more preferably an afucosylated humanized B-Ly1 antibody as described in WO 2005/044859 and WO 2007/031875.

In some embodiments, the anti-CD20 antibody is GA101 antibody. In some embodiments, the GA101 antibody as used herein refers to any one of the following antibodies that bind human CD20: (1) an antibody comprising an HVR-H1 comprising the amino acid sequence of SEQ ID NO:5, an HVR-H2 comprising the amino acid sequence of SEQ ID NO:6, an HVR-H3 comprising the amino acid sequence of SEQ ID NO:7, an HVR-L1 comprising the amino acid sequence of SEQ ID NO:8, an HVR-L2 comprising the amino acid sequence of SEQ ID NO:9, and an HVR-L3 comprising the amino acid sequence of SEQ ID NO:10; (2) an antibody comprising a VH domain comprising the amino acid sequence of SEQ ID NO:11 and a VL domain comprising the amino acid sequence of SEQ ID NO:12, (3) an antibody comprising an amino acid sequence of SEQ ID NO:13 and an amino acid sequence of SEQ ID NO: 14; (4) an antibody known as obinutuzumab, or (5) an antibody that comprises an amino acid sequence that has at least 95%, 96%, 97%, 98% or 99% sequence identity with amino acid sequence of SEQ ID NO:13 and that comprises an amino acid sequence that has at least 95%, 96%, 97%, 98% or 99% sequence identity with an amino acid sequence of SEQ ID NO: 14. In one embodiment, the GA101 antibody is an IgG1 isotype antibody.

In some embodiments, the anti-CD20 antibody is a humanized B-Ly1 antibody. In some embodiments, the humanized B-Ly1 antibody refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO: 3; variable region of the murine light chain (VL): SEQ ID NO: 4—see Poppema, S. and Visser, L., *Biotest Bulletin* 3 (1987) 131-139) by chimerization with a human constant domain from IgG1 and following humanization (see WO 2005/044859 and WO 2007/031875). The humanized B-Ly1 antibodies are disclosed in detail in WO 2005/044859 and WO 2007/031875.

In one embodiment, the humanized B-Ly1 antibody has variable region of the heavy chain (VH) selected from group of SEQ ID NO:15-16 and 40-55 (corresponding to B-HH2 to B-HH9 and B-HL8 to B-HL17 of WO 2005/044859 and WO 2007/031875). In one specific embodiment, such variable domain is selected from the group consisting of SEQ ID NO: 15, 16, 42, 44, 46, 48 and 50 (corresponding to B-HH2, BHH-3, B-HH6, B-HH8, B-HL8, B-HL11 and B-HL13 of WO 2005/044859 and WO 2007/031875). In one specific embodiment, the humanized B-Ly1 antibody has variable region of the light chain (VL) of SEQ ID NO:55 (corresponding to B-KV1 of WO 2005/044859 and WO 2007/031875). In one specific embodiment, the humanized B-Ly1 antibody has a variable region of the heavy chain (VH) of SEQ ID NO:42 (corresponding to B-HH6 of WO 2005/044859 and WO 2007/031875) and a variable region of the light chain (VL) of SEQ ID NO:55 (corresponding to B-KV1 of WO 2005/044859 and WO 2007/031875). Furthermore in one embodiment, the humanized B-Ly1 antibody is an IgG1 antibody. According to the invention, such afocusylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the afucosylated glyco-engineered humanized B-Ly1 is B-HH6-B-KV1 GE. In one embodiment, the anti-CD20 antibody is obinutuzumab (recommended INN, WHO Drug Information, Vol. 26, No. 4, 2012, p. 453). As used herein, obinutuzumab is synonymous for GA101 or RO5072759. This replaces all previous versions (e.g., Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In some embodiments, the humanized B-Ly1 antibody is an antibody comprising a heavy chain comprising the amino acid sequence of SEQ ID NO:17 and a light chain comprising the amino acid sequence of SEQ ID NO:18 or an antigen-binding fragment thereof. In some embodiments, the humanized B-Ly1 antibody comprises a heavy chain variable region comprising the three heavy chain CDRs of SEQ ID NO:17 and a light chain variable region comprising the three light chain CDRs of SEQ ID NO:18.

In some embodiments, the humanized B-Ly1 antibody is an afucosylated glyco-engineered humanized B-Ly1. Such glycoengineered humanized B-Ly1 antibodies have an altered pattern of glycosylation in the Fc region, preferably having a reduced level of fucose residues. Preferably the amount of fucose is about 60% or less of the total amount of oligosaccharides at Asn297 (in one embodiment the amount of fucose is between about 40% and about 60%, in another embodiment the amount of fucose is about 50% or less, and in still another embodiment the amount of fucose is about 30% or less). Furthermore the oligosaccharides of the Fc region are preferably bisected. These glycoengineered humanized B-Ly1 antibodies have an increased ADCC.

The "ratio of the binding capacities to CD20 on Raji cells (ATCC-No. CCL-86) of an anti-CD20 antibodies compared to rituximab" is determined by direct immunofluorescence measurement (the mean fluorescence intensities (MFI) is measured) using said anti-CD20 antibody conjugated with Cy5 and rituximab conjugated with Cy5 in a FACSArray (Becton Dickinson) with Raji cells (ATCC-No. CCL-86), as described in Example No. 2, and calculated as follows:

$$\text{Ratio of the binding capacities to } CD20 \text{ on Raji cells(ATCC-No. CCL-86)} = \frac{MFI(Cy5\text{-anti-}CD20 \text{ antibody})}{MFI(Cy5\text{-rituximab})} \times \frac{Cy5\text{-labeling ratio}(Cy5\text{-rituximab})}{Cy5\text{-labeling ratio}(Cy5\text{-anti-}CD20 \text{ antibody})}$$

MFI is the mean fluorescent intensity. The "Cy5-labeling ratio" as used herein means the number of Cy5-label molecules per molecule antibody.

Typically said type II anti-CD20 antibody has a ratio of the binding capacities to CD20 on Raji cells (ATCC-No. CCL-86) of said second anti-CD20 antibody compared to rituximab of 0.3 to 0.6, and in one embodiment, 0.35 to 0.55, and in yet another embodiment, 0.4 to 0.5.

By "antibody having increased antibody dependent cellular cytotoxicity (ADCC)", it is meant an antibody, as that term is defined herein, having increased ADCC as determined by any suitable method known to those of ordinary skill in the art.

One accepted in vitro ADCC assay is as follows:
1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at 5×10$^6$ cells/ml in RPMI cell culture medium;
   ii) the target cells are grown by standard tissue culture methods, harvested from the exponential growth phase with a viability higher than 90%, washed in RPMI cell culture medium, labeled with 100 microCuries of $^{51}$Cr, washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (VN) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector: target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter;

x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point V above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. In one embodiment, the increase in ADCC is relative to the ADCC, measured with the above assay, mediated by the same antibody, produced by the same type of host cells, using the same standard production, purification, formulation and storage methods, which are known to those skilled in the art, except that the comparator antibody (lacking increased ADCC) has not been produced by host cells engineered to overexpress GnTIII and/or engineered to have reduced expression from the fucosyltransferase 8 (FUT8) gene (e.g., including, engineered for FUT8 knock out).

In some embodiments, the "increased ADCC" can be obtained by, for example, mutating and/or glycoengineering of said antibodies. In one embodiment, the antibody is glycoengineered to have a biantennary oligosaccharide attached to the Fc region of the antibody that is bisected by GlcNAc. In another embodiment, the antibody is glycoengineered to lack fucose on the carbohydrate attached to the Fc region by expressing the antibody in a host cell that is deficient in protein fucosylation (e.g., Lec13 CHO cells or cells having an alpha-1,6-fucosyltransferase gene (FUT8) deleted or the FUT gene expression knocked down). In yet another embodiment, the antibody sequence has been engineered in its Fc region to enhance ADCC (e.g., in one embodiment, such engineered antibody variant comprises an Fc region with one or more amino acid substitutions at positions 298, 333, and/or 334 of the Fc region (EU numbering of residues)).

In some embodiments, the term "complement-dependent cytotoxicity (CDC)" refers to lysis of human tumor target cells by the antibody according to the invention in the presence of complement. CDC can be measured by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. In one embodiment, the assay is performed with $^{51}$Cr or Eu labeled tumor cells and measurement of released $^{51}$Cr or Eu. Controls include the incubation of the tumor target cells with complement but without the antibody.

In a further aspect of the invention, an anti-CD20 antibody according to any of the above embodiments is a monoclonal antibody, including a human antibody. In one embodiment, an anti-CD20 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an antibody according to any of the above embodiments may incorporate any of the features, singly or in combination, as described in below.

1. Antibody Affinity

In certain embodiments, an antibody provided herein has a dissociation constant (Kd) of ≤1 μM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{121}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies for use in the methods described herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody is useful in a method described herein. Multispecific antibodies are monoclonal antibodies that have binding specificities for at least two different sites. In certain embodiments, one of the binding specificities is for one antigen (e.g., CD79b) and the other is for any other antigen. In certain embodiments, one of the binding specificities is for one antigen (e.g., CD79b) and the other is for CD3. See, e.g., U.S. Pat. No. 5,821,337. In certain embodiments, bispecific antibodies may bind to two different epitopes of an antigen (e.g., CD79b). Bispecific antibodies may also be used to localize cytotoxic agents to cells which express the antigen (e.g., CD79b). Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bispecific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to CD79b as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Nonlimiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d. Cysteine Engineered Antibody Variants

In certain embodiments, it may be desirable to create cysteine engineered antibodies, e.g., "thioMAbs," in which one or more residues of an anti-CD79b antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Nonlimiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

C. Recombinant Methods and Compositions

Antibodies may be produced using recombinant methods and compositions, e.g., as described in U.S. Pat. No. 4,816, 567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

D. Assays

Antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to the target antigen. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized antigen is incubated in a solution comprising a first labeled antibody that binds to antigen (e.g., any of the antibodies described herein) and a second unlabeled antibody that is being tested for its ability to compete with the first antibody for binding to antigen. The second antibody may be present in a hybridoma supernatant. As a control, immobilized antigen is incubated in a solution comprising the first labeled antibody but not the second unlabeled antibody. After incubation under conditions permissive for binding of the first antibody to antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to antigen. See Harlow and Lane (1988) *Antibodies: A Laboratory Manual* ch. 14 (Cold Spring Harbor Laboratory, Cold Spring Harbor, NY).

E. Immunoconjugates

Provided herein are also immunoconjugates comprising an anti-CD79b antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate) for use in the methods described herein.

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Charm, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine. In some embodiments of any of the methods, the immunoconjugate has the formula Ab-(L-D)p, wherein: (a) Ab is the antibody which binds a MM cell surface protein; (b) L is a linker; (c) D is a cytotoxic agent; and (d) p ranges from 1-8.

An exemplary ADC has Formula I:

$$\text{Ab-(L-D)}_p \qquad \qquad \text{I}$$

wherein p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., *Cancer Research* 52:127-131 (1992); U.S. Pat. No. 5,208,020).

In certain embodiments, a linker has the following Formula II:

$$\text{-A}_a\text{-W}_w\text{—Y}_y\text{—} \qquad \qquad \text{II}$$

wherein A is a "stretcher unit", and a is an integer from 0 to 1; W is an "amino acid unit", and w is an integer from 0 to 12; Y is a "spacer unit", and y is 0, 1, or 2; and Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

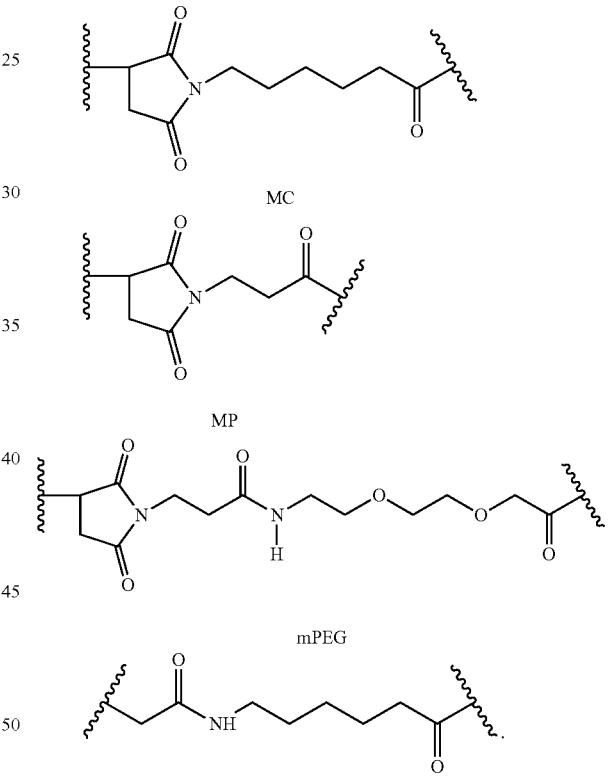

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit is p-aminobenzyloxycarbonyl (PAB). In some embodiments, an ADC comprising a self-immolative linker has the structure:

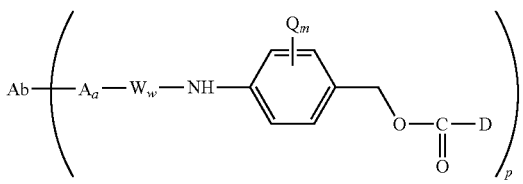

wherein Q is —$C_1$-$C_8$ alkyl, —O—($C_1$-$C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984) *J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

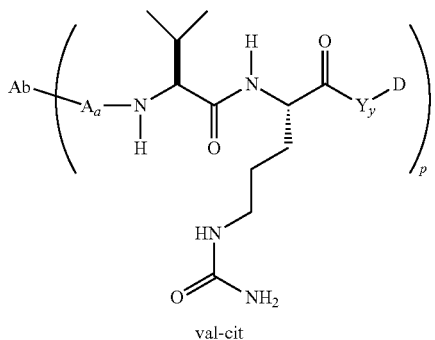

val-cit

-continued

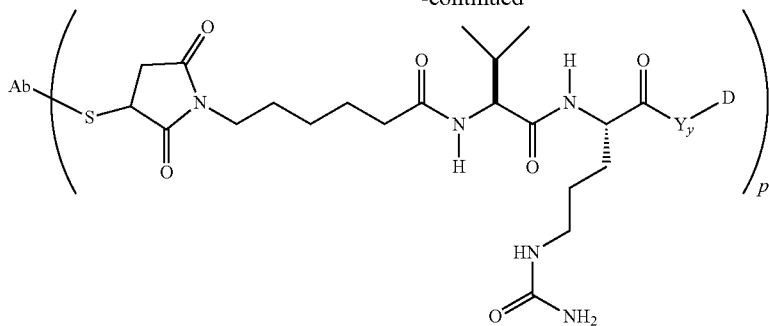

MC-val-cit

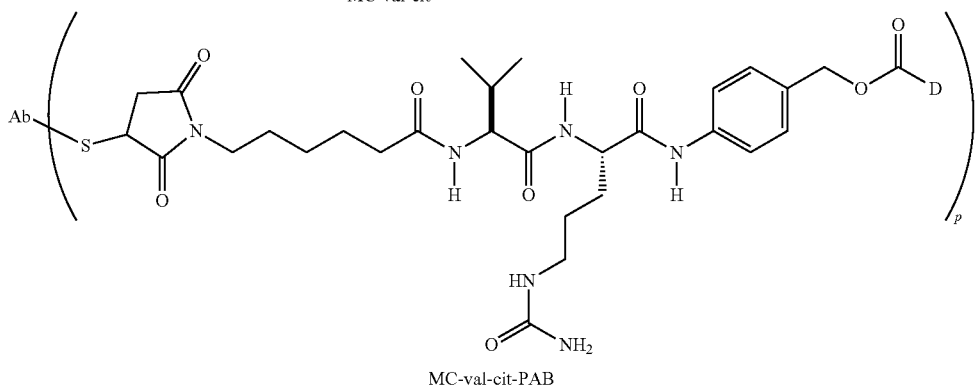

MC-val-cit-PAB

Further nonlimiting exemplary ADCs include the structures:

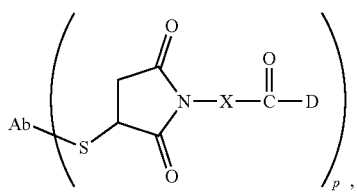

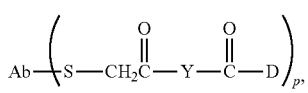

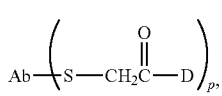

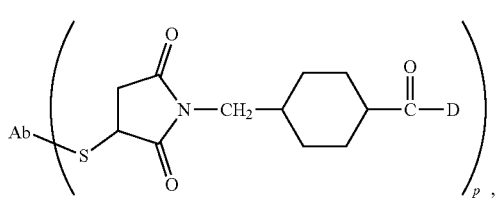

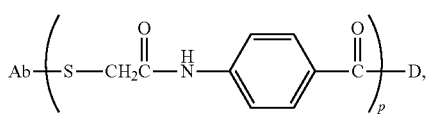

wherein X is:

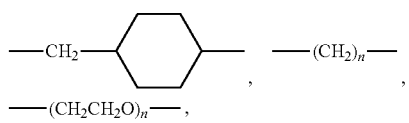

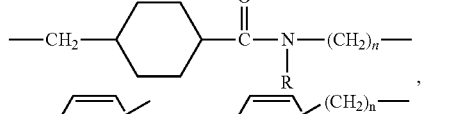

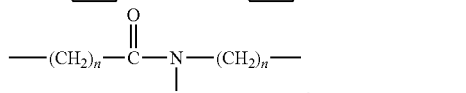

, or

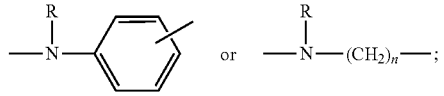

Y is:

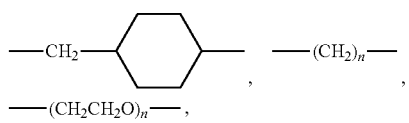

each R is independently H or $C_1$-$C_6$ alkyl; and n is 1 to 12.

Typically, peptide-type linkers can be prepared by forming a peptide bond between two or more amino acids and/or peptide fragments. Such peptide bonds can be prepared, for example, according to a liquid phase synthesis method (e.g., E. Schröder and K. Lübke (1965) "The Peptides", volume 1, pp 76-136, Academic Press).

In some embodiments, a linker is substituted with groups that modulate solubility and/or reactivity. As a nonlimiting example, a charged substituent such as sulfonate (—$SO_3$—)

or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion)$^a$ substituents, such that more than one drug is coupled to the antibody in the ADC of Formula I.

The compounds of the invention expressly contemplate, but are not limited to, ADC prepared with the following linker reagents: bis-maleimido-trioxyethyletne glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl)aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone) benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

Certain useful linker reagents can be obtained from various commercial sources, such as Pierce Biotechnology, Inc. (Rockford, IL), Molecular Biosciences Inc. (Boulder, CO), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) *PNAS* 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424, 219) (prepared, for example, by the reaction of maytansinol with H2S or P2S5); C-14-alkoxymethyl(demethoxy/ CH$_2$OR)(U.S. Pat. No. 4,331,598); C-14-hydroxymethyl or acyloxymethyl (CH$_2$OH or CH$_2$OAc) (U.S. Pat. No. 4,450, 254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315, 929) (for example, isolated from *Trewia nudlflora*); C-18-N-demethyl (U.S. Pat. Nos. 4,362,663 and 4,322,348) (prepared, for example, by the demethylation of maytansinol

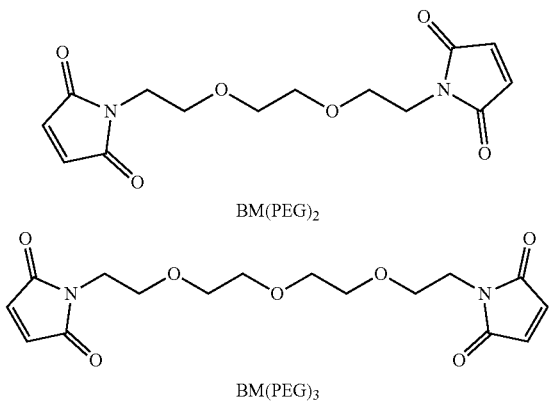

BM(PEG)$_2$

BM(PEG)$_3$ by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

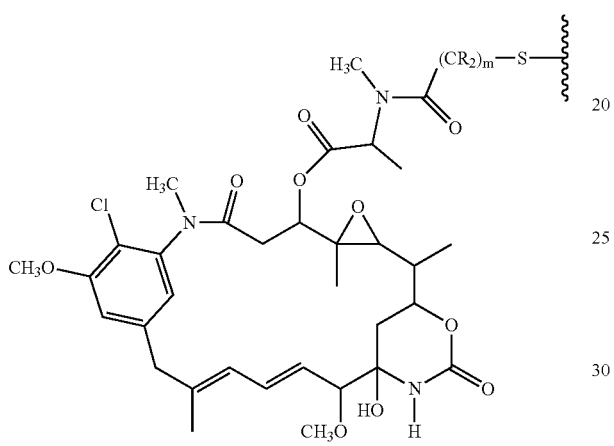

wherein the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. Nos. 633,410; 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

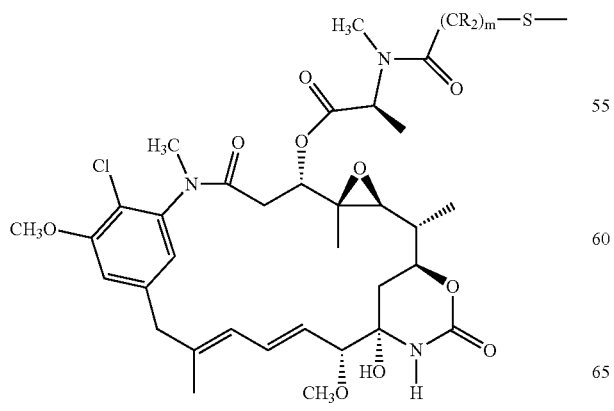

Exemplary embodiments of maytansinoid drug moieties include, but are not limited to, DM1; DM3; and DM4, having the structures:

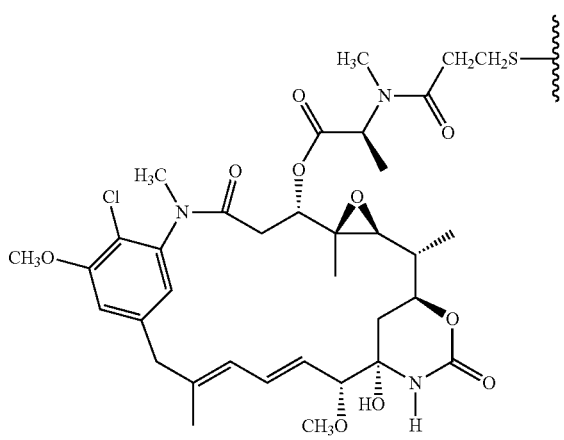

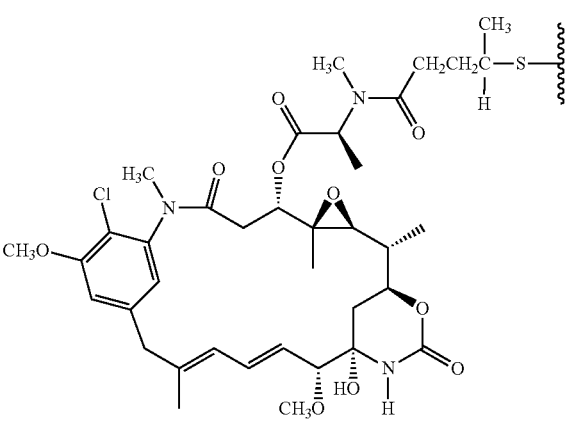

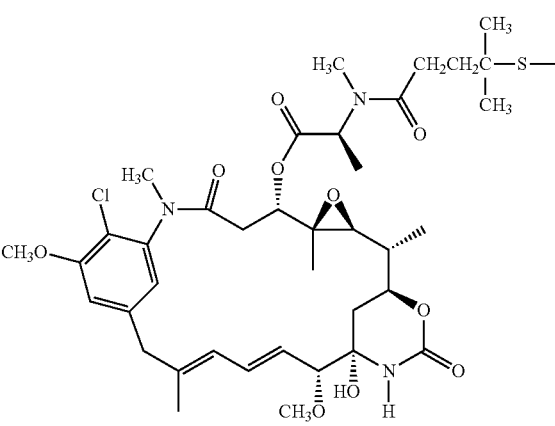

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):
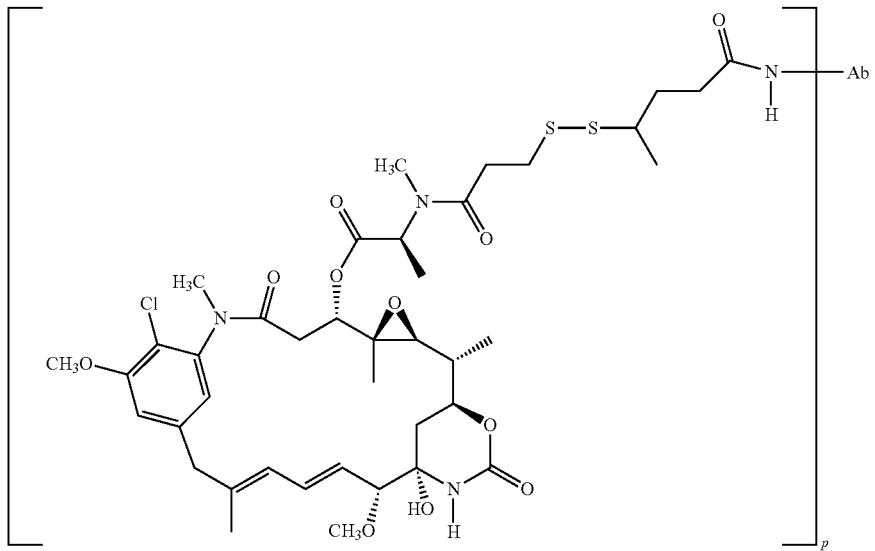
Ab-SPP-DM1
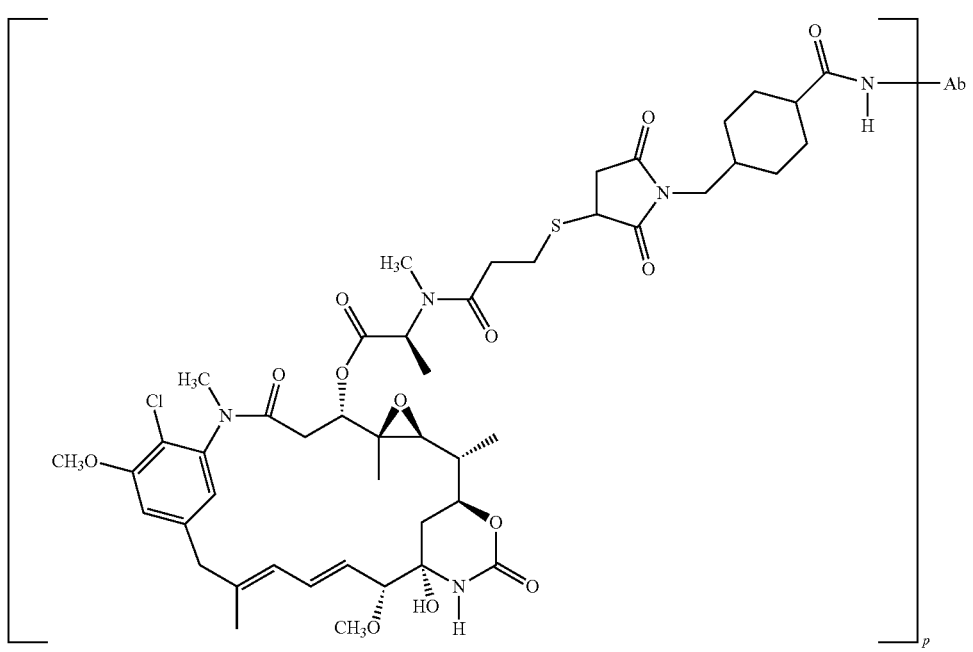
Ab-SMCC-DM1

Exemplary antibody-drug conjugates where DM1 is linked through a BMPEO linker to a thiol group of the antibody have the structure and abbreviation:

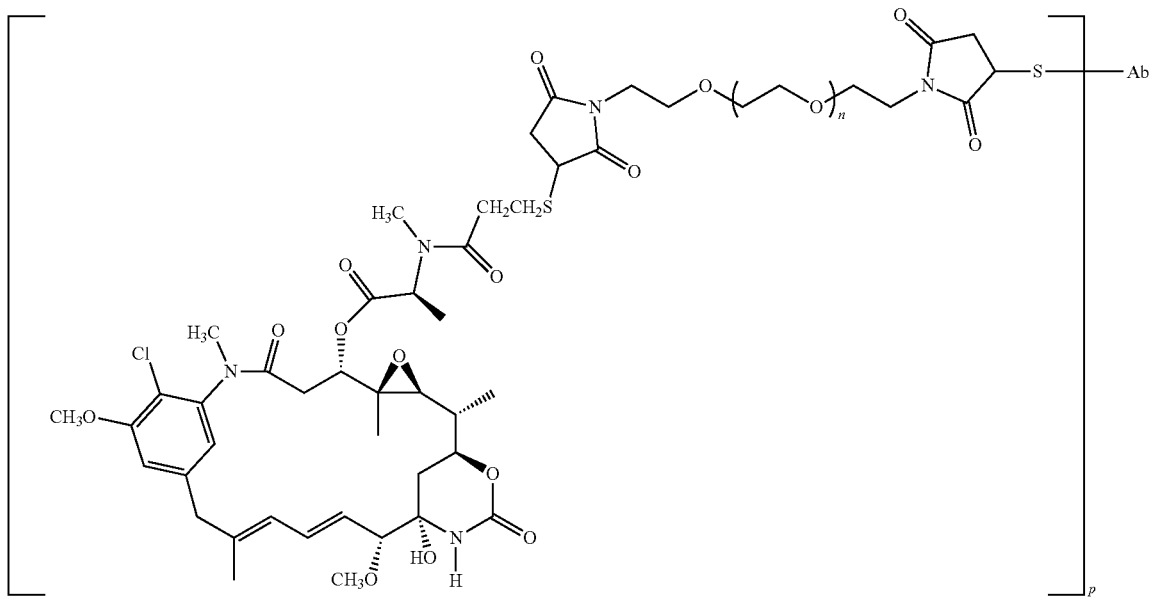

wherein Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties DE and DF, disclosed in U.S. Pat. Nos. 7,498,298 and 7,659,241, the disclosures of which are expressly incorporated by reference in their entirety:

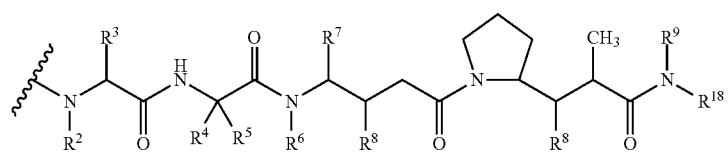

$D_E$

-continued $D_F$

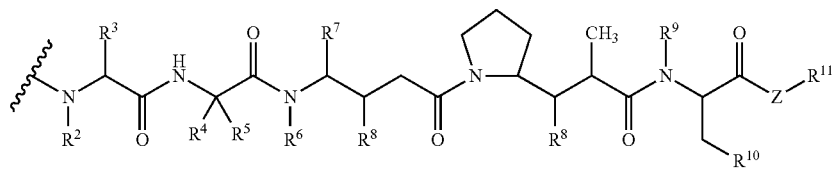

wherein the wavy line of DE and DF indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^2$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^5$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R'^8$ is selected from —$C(R^8)_2$—$C(R^8)_2$-aryl, —$C(R^8)_2$—$C(R^8)_2$—($C_3$-$C_8$ heterocycle), and —$C(R')_2$—$C(R')_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of R' is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of R' is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{11})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula DE is MMAE, wherein the wavy line indicates the covalent attachment to a linker (L) of an antibody-drug conjugate:

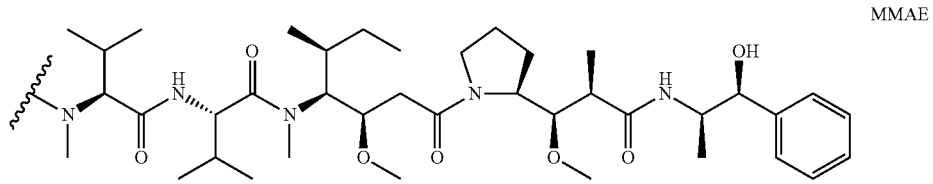 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula DF is MMAF, wherein the wavy line indicates the covalent attachment to a linker (L) of an antibody-drug conjugate:

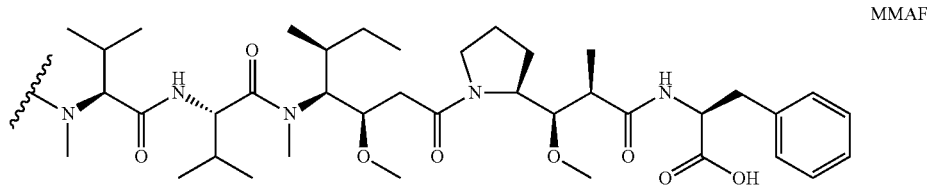 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 1 5:859-863; and Doronina (2003) *Nat. Biotechnol.* 21(7): 778-784.

In some embodiments, auristatin/dolastatin drug moieties of formulas DE such as MMAE, and DF, such as MMAF, and drug-linker intermediates and derivatives thereof, such

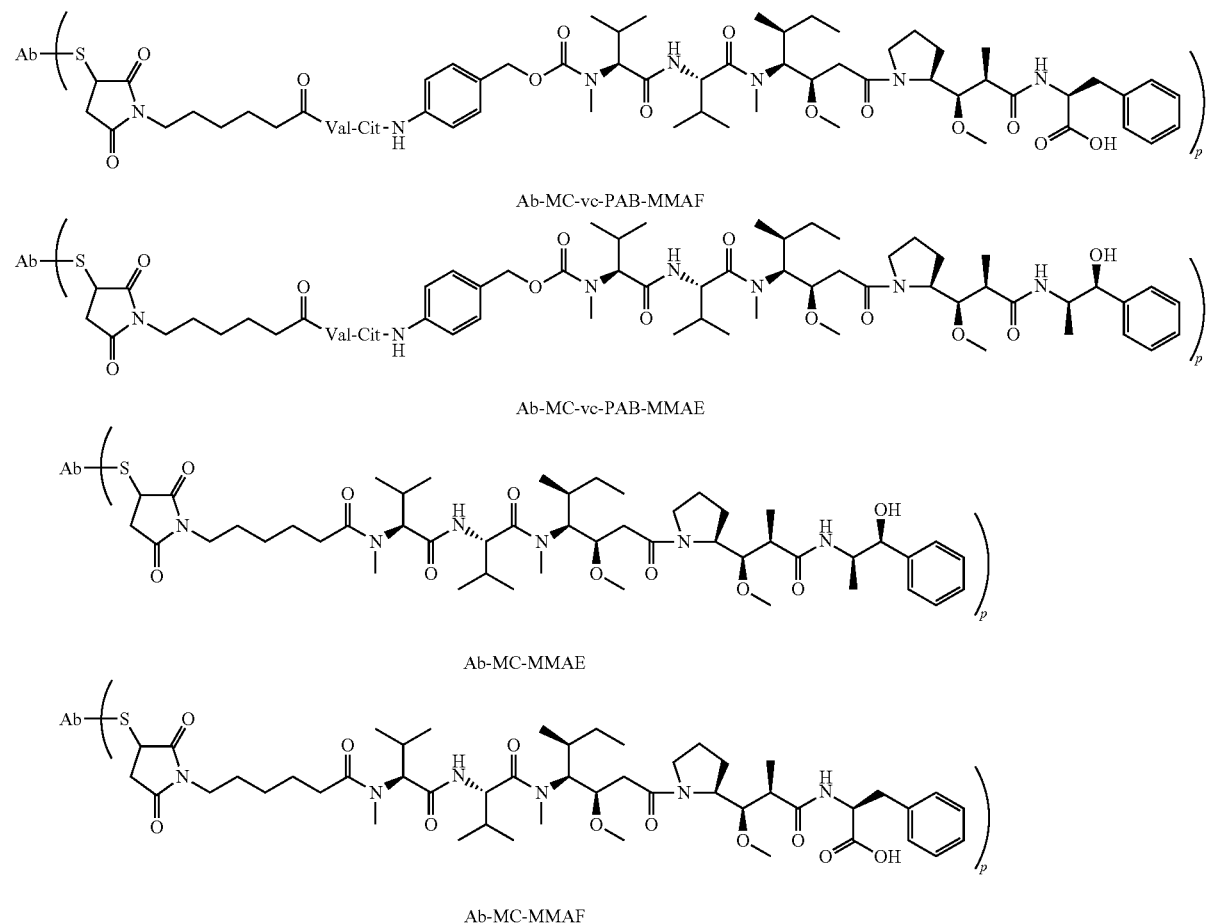

Ab-MC-vc-PAB-MMAF

Ab-MC-vc-PAB-MMAE

Ab-MC-MMAE

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schroder and K. Libke, "The Peptides", as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

(4) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as D-galactosidase and neuraminidase, which are useful for converting glycosylated prodrugs into free drugs; D-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g., p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g., hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

F. Methods and Compositions for Diagnostics and Detection

Provided herein are also methods and compositions for diagnosis and/or detection of CD79b antibodies for use in the methods described herein including detecting the presence of CD79b in a biological sample for use in selecting patients for treating using the methods described herein. The term "detecting" as used herein encompasses quantitative or qualitative detection. A "biological sample" comprises, e.g., a cell or tissue.

In one embodiment, an anti-CD79b antibody for use in a method of diagnosis or detection is provided. In a further aspect, a method of detecting the presence of CD79b in a biological sample is provided. In certain embodiments, the method comprises contacting the biological sample with an anti-CD79b antibody as described herein under conditions permissive for binding of the anti-CD79b antibody to CD79b, and detecting whether a complex is formed between the anti-CD79b antibody and CD79b in the biological sample. Such method may be an in vitro or in vivo method. In one embodiment, an anti-CD79b antibody is used to select subjects eligible for therapy with an anti-CD79b antibody, e.g., where CD79b is a biomarker for selection of patients. In a further embodiment, the biological sample is a cell and/or tissue (e.g., bone marrow and/or blood).

In a further embodiment, an anti-CD79b antibody is used in vivo to detect, e.g., by in vivo imaging, a CD79b-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a CD79b-positive cancer in a subject, the method comprising administering a labeled anti-CD79b antibody to a subject having or suspected of having a CD79b-positive cancer, and detecting the labeled anti-CD79b antibody in the subject, wherein detection of the labeled anti-CD79b antibody indicates a CD79b-positive cancer in the subject. In certain of such embodiments, the labeled anti-CD79b antibody comprises an anti-CD79b antibody conjugated to a positron emitter, such as $^{68}$Ga, $^{18}$F, $^{64}$Cu, $^{86}$Y, $^{76}$Br, $^{89}$Zr, and $^{24}$I. In a particular embodiment, the positron emitter is $^{89}$Zr.

In further embodiments, a method of diagnosis or detection comprises contacting a first anti-CD79b antibody immobilized to a substrate with a biological sample to be tested for the presence of CD79b, exposing the substrate to a second anti-CD79b antibody, and detecting whether the second anti-CD79b is bound to a complex between the first anti-CD79b antibody and CD79b in the biological sample. A substrate may be any supportive medium, e.g., glass, metal, ceramic, polymeric beads, slides, chips, and other substrates. In certain embodiments, a biological sample comprises a cell or tissue (e.g., blood and/or bone marrow). In certain embodiments, the first or second anti-CD79b antibody is any of the antibodies described herein.

Exemplary disorders that may be diagnosed or detected according to any of the above embodiments include CD79b-positive cancers, such as lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), Burkitt's lymphoma, diffuse B-cell lymphoma (DBCL), and mantle cell lymphoma, in particular, NHL, follicular lymphoma, and/or DBCL. In some embodiments, a CD79b-positive cancer is a cancer that expresses CD79b according to a reverse-transcriptase PCR (RT-PCR) assay that detects CD79b mRNA. In some embodiments, the RT-PCR is quantitative RT-PCR.

In certain embodiments, labeled anti-CD79b antibodies for use in the methods described herein are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, D-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

G. Pharmaceutical Formulations

Pharmaceutical formulations of any of the agents described herein (e.g., anti-CD79b immunoconjugates) for use in any of the methods as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g., films, or microcapsules.

The formulations to be used for in vivo administration are generally sterile. Sterility may be readily accomplished, e.g., by filtration through sterile filtration membranes.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1—Anti-CD79b Immunoconjugate in Combination with Anti-CD20 Antibody Plus Alkyating Agent (Bendamustine) in Lymphoma The combination efficacy of anti-CD79b immunoconjugate (anti-CD79b (huMA79b.v28)-MC-vc-PAB-MMAE ADC; polatuzumab vedotin; Pola; DCDS4501A) with anti-CD20 antibody (rituximab) and bendamustine was evaluated in a tumor xenograft model of WSU-DLCL2 human diffuse large B-cell lymphoma.

Female C.B-17 SCID mice (11-12 weeks old from Charles River Laboratories; Hollister, CA) were each inoculated subcutaneously in the flank with 20 million WSU-DLCL2 cells (DSMZ, German Collection of Microorganisms an Cell Cultures; Braunschweig, Germany). When the xenograft tumors reached desired volume, animals were randomized into groups of 9 mice each and received a single dose of treatments (referred to as Day 0). Anti-CD20 antibody (rituximab) was given intraperitoneally at 30 mg/kg. Anti-CD79b-MMAE ADC and bendamustine was given intravenously at 2 and 30 mg/kg, respectively.

Tumors were measured 1-2 times a week throughout the study using UltraCal-IV calipers and tumor volume was calculated using following formula: tumor volume $(mm^3)=0.5a \times b^2$, wherein a and b are the long and short diameters of the tumor, respectively.

To appropriately analyze the repeated measurement of tumor volumes from the same animals over time, a mixed modeling approach was used (Pinheiro J, et al. nlme: linear and nonlinear mixed effects models. 2009; R package, version 3.1-96). This approach addressed both repeated measurements and modest dropout rates due to non-treatment related removal of animals before the study end. Cubic regression splines were used to fit a non-linear profile to the time courses of log 2 tumor volume at each dose level. These non-linear profiles were then related to dose within the mixed model. The results were plotted as fitted tumor volume of each group over time.

In this study, as shown in FIG. 1, anti-CD79b-MMAE ADC demonstrated clear inhibition of tumor growth, and the anti-tumor activity was comparable with the combination of rituximab and bendamustine at the doses tested. Additionally, the triple combination of anti-CD79b-MMAE ADC with rituximab and bendamustine resulted in significantly greater efficacy than the ADC or rituximab/bendamustine doublet alone.

Example 2—a Study of CD79b-MC-Vc-PAB-MMAE in Combination with Anti-CD20 Antibody (Rituximab or Obinutuzumab) Plus Alkylating Agent (Bendamustine) in Patients with Relapsed or Refractory Follicular or Diffuse Large B-Cell Lymphoma A multicenter, open-label study of polatuzumab vedotin (anti-CD79b (huMA79b.v28)-MC-vc-PAB-MMAE; "Pola") administered by intravenous (IV) infusion in combination with standard doses of bendamustine (B) and rituximab (R) or obinutuzumab (G) in patients with relapsed or refractory follicular lymphoma (FL) or diffuse large B-cell lymphoma (DLBCL) is initiated. The study comprises first stage dose-escalation stage, stage 2, and stage 3, and the time on treatment is 18-24 weeks.

In the first stage, FL and DLBCL patients are enrolled into separate cohorts for dose escalation of Pola in combination with R and B or G and B. Pola is administered intravenously on Day 2 of Cycle 1, then on Day 1 of each subsequent cycle. R is administered at a dose of 375 mg/m² intravenously on Day 1 of Cycle 1 and on Day 1 of each subsequent cycle for up to six cycles. B is administered intravenously (90 mg/m²) on Days 2 and 3 of Cycle 1, then on Days 1 and 2 of each subsequent cycle. G is administered intravenously (1000 mg) on Days 1, 8, and 15 of Cycle 1 and on Day 1 of each subsequent cycle for up to six cycles. Complete response (CR) rate is measured by positron emission tomography (PET) scan and is determined by an Institutional Review Board.

In the second stage, randomized, separate FL and DLBCL cohorts receive (a) Pola in combination with R and B or (b) R and B alone. R is administered at a dose of 375 mg/m² intravenously on Day 1 of Cycle 1 and on Day 1 of each subsequent cycle for up to six cycles. B is administered intravenously (90 mg/m²) on Days 2 and 3 of Cycle 1, then on Days 1 and 2 of each subsequent cycle.

In the third stage, non-randomized, separate FL and DLBCL cohorts receive Pola in combination with G and B. B is administered intravenously (90 mg/m²) on Days 2 and 3 of Cycle 1, then on Days 1 and 2 of each subsequent cycle. G is administered intravenously (1000 mg) on Days 1, 8, and 15 of Cycle 1 and on Day 1 of each subsequent cycle for up to six cycles. Complete response (CR) rate is measured by positron emission tomography (PET) scan and is determined by an Institutional Review Board.

Inclusion criteria for patients on study includes:
Histologically confirmed FL (Grade 1, 2, or 3a) or DLBCL
Must have received at least one prior therapy for FL or DLBCL. Patients must have either relapsed or have become refractory to a prior regimen as defined below:
(a) Relapsed/Refractory FL: Patients who have relapsed to prior regimen(s) after having a documented history of response (complete response [CR], CR unconfirmed [CRu], or partial response [PR]) of >/=6 months in duration from completion of regimen(s); refractory to any prior regimen, defined as no response to the prior therapy, or progression within 6 months of completion of the last dose of therapy.
(b) Relapsed/Refractory DLBCL: Patients who are ineligible for second-line stem cell transplant (SCT), with progressive disease or no response (stable disease [SD])<6 months from start of initial therapy; patients who are ineligible for second-line SCT, with disease relapse after initial response of >/=6 months from start of initial therapy; patients who are ineligible for third-line (or beyond) SCT, with progressive disease or no response (SD)<6 months from start of prior therapy; patients who are ineligible for third-line (or beyond) SCT with disease relapse after initial response of >/=6 months from start of prior therapy.
If the patient has received prior bendamustine, response duration must have been >1 year (for patients who have relapse disease after a prior regimen).
At least one bi-dimensionally measurable lesion on imaging scan defined as >1.5 cm in its longest dimension; confirmed availability of archival or freshly collected tumor tissue meeting protocol-defined specifications prior to study enrollment; Life expectancy of at least 24 weeks; Eastern Cooperative Oncology Group (ECOG) Performance Status of 0, 1, or 2; adequate hematological function; and, for women of childbearing potential, a negative serum pregnancy test result within 7 days prior to commencement of dosing.

Exclusion criteria for patients on study includes: history of severe allergic or anaphylactic reactions to humanized or murine monoclonal antibodies (MAbs, or recombinant antibody-related fusion proteins) or known sensitivity or allergy to murine products, contraindication to bendamustine, rituximab, or obinutuzumab, history of sensitivity to mannitol, prior use of any MAb, radioimmunoconjugate, or antibody-drug conjugate (ADC) within 4 weeks before Cycle 1 Day 1, treatment with radiotherapy, chemotherapy, immunotherapy, immunosuppressive therapy, or any investigational agent for the purposes of treating cancer within 2 weeks prior to Cycle 1 Day 1, ongoing corticosteroid use >30 mg/day prednisone or equivalent, for purposes other than lymphoma symptom control, completion of autologous SCT within 100 days prior to Cycle 1 Day 1, prior allogeneic SCT, eligibility for autologous SCT (patients with relapsed/refractory DLBCL), Grade 3b FL, history of transformation of indolent disease to DLBCL, primary CNS lymphoma, current Grade >1 peripheral neuropathy, evidence of significant, uncontrolled concomitant diseases that could affect compliance with the protocol or interpretation of results, including significant cardiovascular disease (such as New York Heart Association Class III or IV cardiac disease, myocardial infarction within the last 6 months, unstable arrhythmias, or unstable angina) or significant pulmonary disease (including obstructive pulmonary disease and history of bronchospasm), known active bacterial, viral, fungal, mycobacterial, parasitic, or other infection (excluding fungal infections of nail beds) at study enrollment or any major episode of infection requiring treatment with intravenous (IV) antibiotics or hospitalization within 4 weeks prior to Cycle 1 Day 1, patients with suspected or latent tuberculosis, positive test results for chronic hepatitis B virus (HBV) infection or for hepatitis C virus (HCV) antibody, known infection with HIV or human T-cell leukemia virus 1 (HTLV-1) virus, women who are pregnant or lactating or who intend to become pregnant within a year of the last dose of rituximab or obinutuzumab, evidence of laboratory abnormalities in standard renal, hepatic or coagulation function tests.

Example 3—Anti-CD79b Immunoconjugate in Combination with Bcl2 Inhibitor in Lymphoma The combination efficacy of anti-CD79b-MMAE ADC (DCDS4501A) with a selective Bcl2 inhibitor (ABT-199 (i.e., venetoclax, GDC-0199, 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino] phenyl}sulfonyl)-2-(1H-pyrrolo[2,3-b]pyridin-5-yloxy) benzamide, and/or CAS #1257044-40-8) was evaluated in a tumor xenograft model of Granta-519 human mantle-cell lymphoma.

Female C.B-17 SCID mice (8 weeks old from Charles River Laboratories; Hollister, CA) were each inoculated in the flank with 20 million Granta-519 cells. When the xenograft tumors reached desired volume, animals were randomized into groups of 9 mice each and received treatments (Day 0 of the study). Anti-CD79b-MC-vc-PAB-MMAE ADC was dosed once intravenously at 1 mg/kg and ABT-199 were given orally once a day for 21 days at 100 mg/kg.

Tumors were measured 1-2 times a week throughout the study using UltraCal-IV calipers and tumor volume was calculated using following formula: tumor volume (mm³) $=0.5 \times a \times b^2$, wherein a and b are the long and short diameters of the tumor, respectively.

To appropriately analyze the repeated measurement of tumor volumes from the same animals over time, a mixed modeling approach was used (Pinheiro J, et al. nlme: linear and nonlinear mixed effects models. 2009; R package, version 3.1-96). This approach addresses both repeated measurements and modest dropout rates due to non-treatment related removal of animals before the study end. Cubic regression splines were used to fit a non-linear profile to the time courses of log 2 tumor volume at each dose level. These non-linear profiles were then related to dose within the mixed model. The results were plotted as fitted tumor volume of each group over time.

Figure 2:
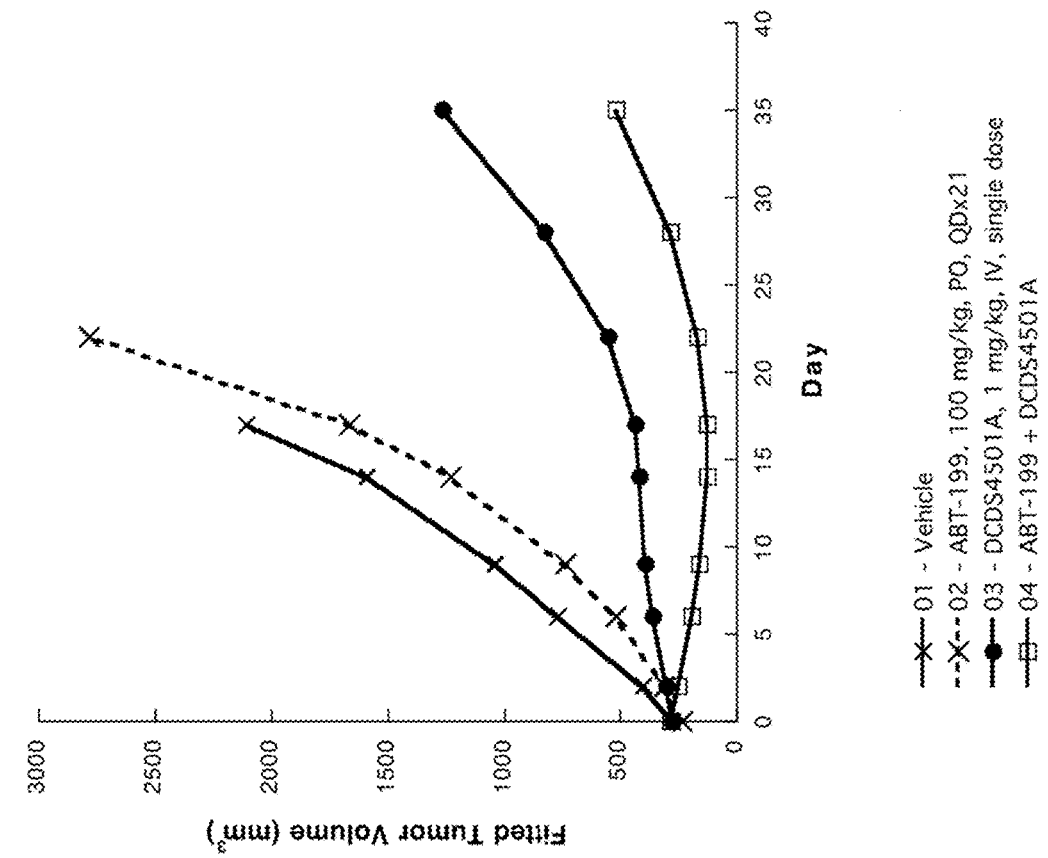
FIG. 2 shows change in tumor volume ($mm^3$) upon treatment of tumor xenografts model of Granta-519 human mantle-cell lymphoma with (a) vehicle, (b) huMA79bv28-MC-vc-PAB-MMAE (DCDS4501A), (c) ABT-199, and (d) huMA79bv28-MC-vc-PAB-MMAE (DCDS4501A)+ABT-199. huMA79bv28-MC-vc-PAB-MMAE (DCDS4501A): 1 mg/kg, iv, once on day 0 and ABT-199: 100 mg/kg, po, qd21.

In this study, as shown in FIG. 2, treatment with anti-CD79b-MC-vc-PAB-MMAE ADC alone caused modest tumor growth delay while ABT-199 monotherapy did not result in anti-tumor activity. However, the combination of anti-CD79b-MC-vc-PAB-MMAE ADC and ABT-199 resulted in greater efficacy, causing tumor regressions, than either agent alone. The combination of anti-CD79b-MC-vc-PAB-MMAE ADC and ABT-199 was well-tolerated based on minimal changes in animal body weights during the treatment period.

Example 4—Anti-CD79b Immunoconjugate in Combination Therapy in Lymphoma

The combination efficacy of anti-CD79b-MC-vc-PAB-MMAE ADC (DCDS4501A; huMA79bv28-MC-vc-PAB-MMAE) with various combination therapies was evaluated in a tumor xenograft model of WSU-DLCL2 (DLBCL).

Female C.B-17 SCID mice (14 weeks old from Charles River Laboratories; Hollister, CA) were each inoculated in the flank with 20 million WSU-DLCL2 (DLBCL) cells. When the xenograft tumors reached desired volume, animals were randomized and received treatments (Day 0 of the study). There were six treatment groups (1) vehicle, (2) anti-CD79b-vcMMAE, (3) G-CHP (GA101-cyclophosphamide, doxorubicin, and prednisone), (4) G-bendamustine (GA101-bendamustine), (5) G-CHP (GA101-cyclophosphamide, doxorubicin, and prednisone)+anti-CD79b-MC-vc-PAB-MMAE, and (6) G-bendamustine (GA101-bendamustine)+anti-CD79b-MC-vc-PAB-MMAE.

CD79b-MC-vc-PAB-MMAE ADC was dosed once intravenously at 2 mg/kg, iv, once. GA101 dosed 30 mg/kg, ip, once. CHP was dosed cyclophosphamide, 30 mg/kg, iv, once+doxorubicin, 2.475 mg/kg, iv, once+prednisone, 0.15 mg/kg, po, qdx5. Bendamustine was dosed 30 mg/kg, iv, once.

As described above, tumors were measured 1-2 times a week throughout the study using UltraCal-IV calipers and tumor volume was calculated using following formula: tumor volume (mm$^3$) -0.5a×b$^2$, wherein a and b are the long and short diameters of the tumor, respectively.

Figure 3B:
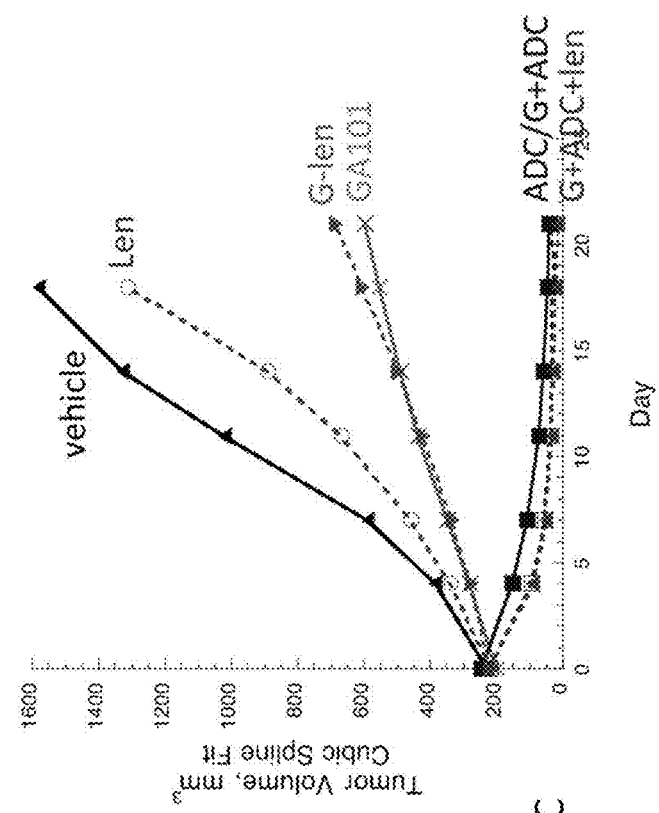
FIGS. 3A-3B show change in tumor volume ($mm^3$) upon treatment of tumor xenografts model of WSU-DLCL2 (DLBCL) and TMD8 (ABC-DLBCL) with various combination therapy regimens including huMA79bv28-MC-vc-PAB-MMAE.
Figure 3A:
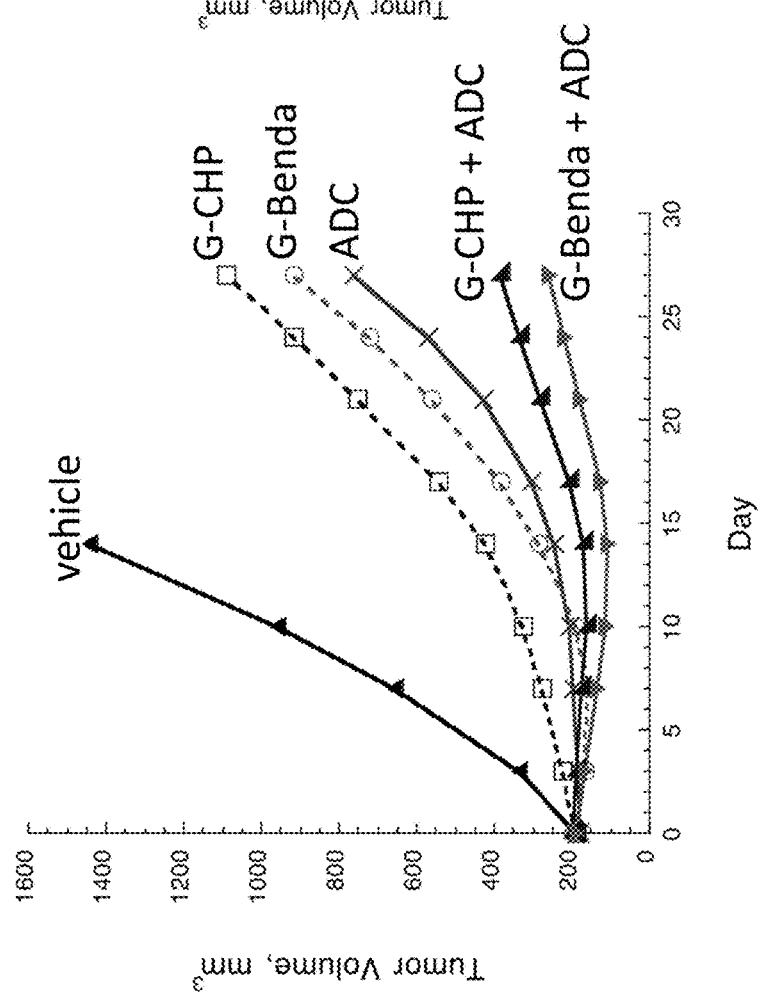

In this study, as shown in FIG. 3A, treatment with anti-CD79b-MC-vc-PAB-MMAE ADC combined well with G-CHP (or G-Benda) with better efficacy than the anti-CD79b-MC-vc-PAB-MMAE ADC or G-CHP (or G-Benda) alone. The combinations were well-tolerated based on minimal changes in animal body weights during the treatment period.

Example 5—Anti-CD79b Immunoconjugate in Combination Therapy in Lymphoma

The combination efficacy of anti-CD79b-MC-vc-PAB-MMAE ADC (DCDS4501A; huMA79bv28-MC-vc-PAB-MMAE) with various combination therapies was evaluated in a tumor xenograft model of TMD8 (ABC-DLBCL).

Female C.B-17 SCID mice (13 weeks old from Charles River Laboratories; Hollister, CA) were each inoculated in the flank with 5 million TMD8 (ABC-DLBCL) cells. When the xenograft tumors reached desired volume, animals were randomized and received treatments (Day 0 of the study). There were seven treatment groups (1) vehicle, (2) GA101, (3) anti-CD79b-MC-vc-PAB-MMAE, (4) lenalidomide, (5) GA101+anti-CD79b-MC-vc-PAB-MMAE, (6) GA101+lenalidomide, and (7) GA101+lenalidomide+anti-CD79b-MC-vc-PAB-MMAE. CD79b-MC-vc-PAB-MMAE ADC was dosed once intravenously at 2 mg/kg, iv, once. GA101 dosed 1 mg/kg, ip, qwx3. Lenalidomide was administered at 20 mg/kg, po, (qdx5)x3.

As described above, tumors were measured 1-2 times a week throughout the study using UltraCal-IV calipers and tumor volume was calculated using following formula: tumor volume (mm$^3$) -0.5a×b$^2$, wherein a and b are the long and short diameters of the tumor, respectively.

Literature (Br J Haematol 2013 Zhang et al.) reported that lenalidomide preferentially suppresses the growth of the activated B-cell-like (ABC) subtype, with minimal effect on non-ABC-DLBCL cells. In this study using ABC-DLBCL, as shown in FIG. 3B, treatment with lenalidomide monotherapy showed little efficacy in this model. Further, combining lenalidomide with GA101 did not provide additional efficacy over GA101 alone. However, use of anti-CD79b-MC-vc-PAB-MMAE ADC alone or in combination in the ABC subtype showed strong efficacy with tumor regression. In addition, all treatments were well tolerated.

Example 6—Anti-CD79b Immunoconjugate in Combination Therapy in Lymphoma

The combination efficacy of anti-CD79b-MC-vc-PAB-MMAE ADC (DCDS4501A; huMA79bv28-MC-vc-PAB-MMAE) with various combination therapies was evaluated in a tumor xenograft model of WSU-DLCL2 (DLBCL).

Female C.B-17 SCID mice (13 weeks old from Charles River Laboratories; Hollister, CA) were each inoculated in the flank with 20 million WSU-DLCL2 (DLBCL) cells. When the xenograft tumors reached desired volume, animals were randomized and received treatments (Day 0 of the study). There were twelve treatment groups (1) vehicle, (2) GA101, (3) Bcl2i (GDC-199), (4) PI3Ki (GDC-032), (5) anti-CD79b-MC-vc-PAB-MMAE ADC, (6) GA101+anti-CD79b-MC-vc-PAB-MMAE, (7) GA101+Bcl2i (GDC-199), (8) GA101+PI3Ki (GDC-032), (9) GA101+Bcl2i (GDC-199)+anti-CD79b-MC-vc-PAB-MMAE, (10) GA101+PI3Ki (GDC-032)+anti-CD79b-MC-vc-PAB-MMAE, (11) Rituximab, and (12) Rituximab+anti-CD79b-MC-vc-PAB-MMAE.

CD79b-MC-vc-PAB-MMAE ADC was dosed once intravenously at 2 mg/kg, iv, once. GA101 dosed 30 mg/kg, ip, once. Bcl2 inhibitor, GDC-199, was dosed at 100 mg/kg, po, qdx21. PI3K inhibitor, GDC-032 was dosed at 10 mg/kg, po, qdx21. Rituximab was dosed at 30 mg/kg, ip, once.

Figure 4:
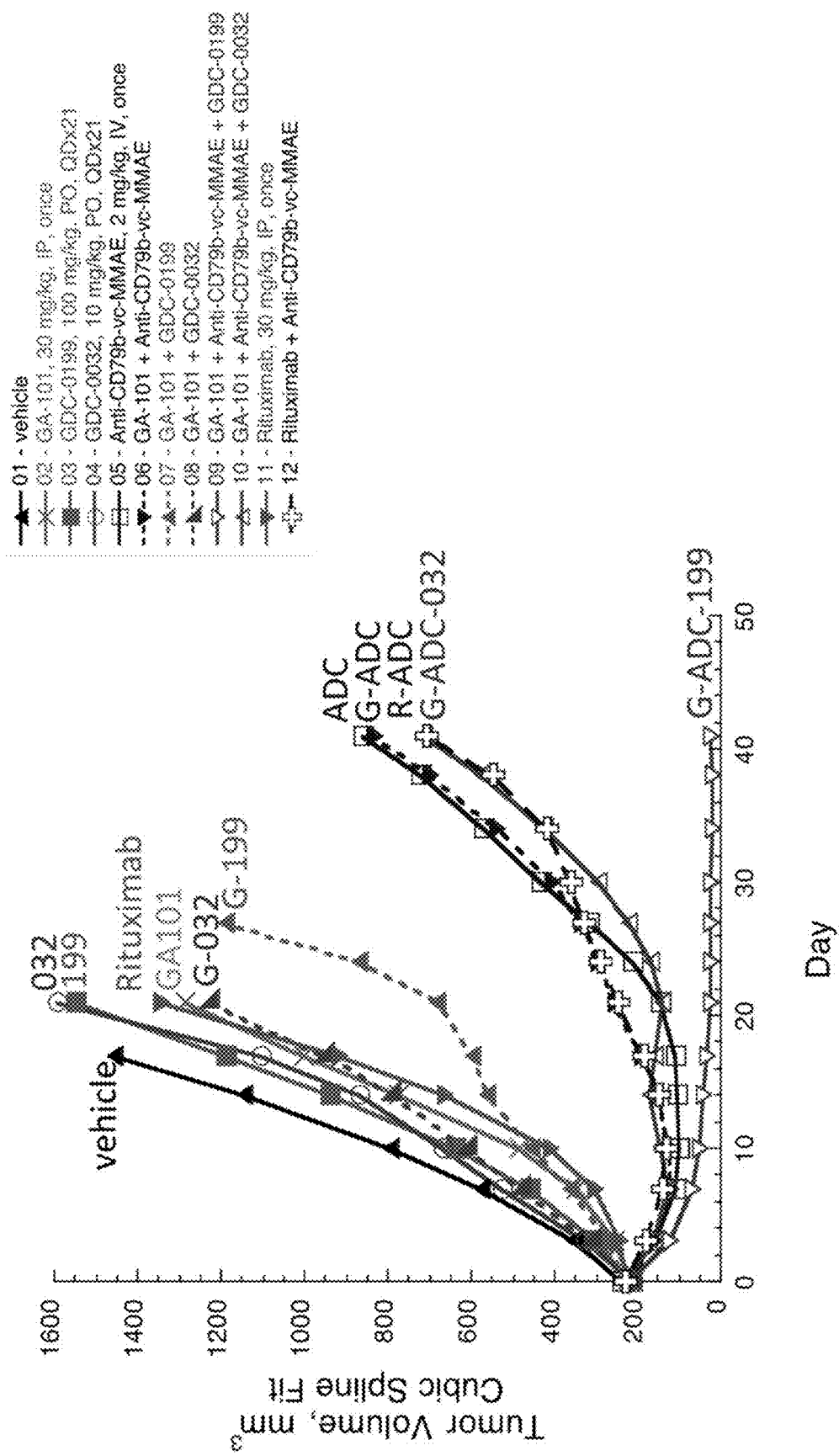
FIG. 4 shows change in tumor volume ($mm^3$) upon treatment of tumor xenografts model of WSU-DLCL2 (DLBCL) with various combination therapy regimens huMA79bv28-MC-vc-PAB-MMAE.

As described above, tumors were measured 1-2 times a week throughout the study using UltraCal-IV calipers and tumor volume was calculated using following formula: tumor volume (mm$^3$) -0.5a×b$^2$, wherein a and b are the long and short diameters of the tumor, respectively. Results are shown in FIG. 4. In this study, the Bcl2 inhibitor, GDC-0199, PI3K inhibitor, GDC-0032, and anti-CD20 (GA101 or Rituximab) monotherapy at the doses tested had little effect on the tumor growth. However, efficacy became more apparent when combining Bcl2 inhibitor GDC-0199 with anti-CD20, GA101. Furthermore, among all the different treatments evaluated the triple combination of anti-CD79b-vcMMAE, GA101 and Bcl2 inhibitor displayed the greatest efficacy, causing complete tumor remission.

Example 7—Anti-CD79b Immunoconjugate in Combination with Venetoclax

This study will evaluate the efficacy, safety, and pharmacokinetics of the combination of obinutuzumab (GA101 or G) plus polatuzumab vedotin (anti-CD79b(huMA79b.v23)-MC-vc-PAB-MMAE ADC (DCDS4501A) or pola) plus a selective Bcl2 inhibitor (ABT-199 (i.e., venetoclax, GDC-0199, 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, V, and/or CAS #1257044-40-8) (G+pola+V) in patients with relapse or refractory (R/R) follicular lymphoma (FL) or diffuse large B cell lymphoma (DLBCL).

Efficacy Objectives: Response will be determined on the basis of positron emission tomography and computed tomography (PET-CT) scans or CT scans alone, using Revised Lugano Response Criteria for Malignant Lymphoma, hereinafter referred to as Lugano 2014 criteria. Response will be determined by an Independent Review Committee (IRC) and by the investigator. The primary efficacy objective for this study is to evaluate the efficacy of G+Pola+V on the basis of the following endpoint: Complete response (CR) at end of induction (EOI), as determined by the IRC on the basis of PET-CT scans.

The secondary efficacy objective for this study is to evaluate the efficacy of G+Pola+V on the basis of the following endpoints: CR at EOI, as determined by the investigator on the basis of PET-CT scans, CR at EOI, as determined by the investigator on the basis of CT scans alone, Objective response (defined as a CR or partial response [PR]) at EOI, as determined by the IRC and by the investigator on the basis of PET-CT scans, Objective response (defined as a CR or PR) at EOI, as determined by the IRC and by the investigator on the basis of CT scans alone, Best response of CR or PR during the study, as determined by the investigator on the basis of CT scans alone.

The exploratory efficacy objective for this study is to evaluate the long-term efficacy of G+Pola+V on the basis of the following endpoints: for patients who have positive PET scans at EOJ: CR at 12 months, as determined by the IRC and by the investigator on the basis of PET-CT scans, progression-free survival, defined as the time from initiation of study treatment to first occurrence of disease progression or relapse, as determined by investigator on the basis of CT scans alone, or death from any cause, event-free survival, defined as the time from initiation of study treatment to any treatment failure, including disease progression or relapse, as determined by investigator on the basis of CT scans alone, initiation of new anti-lymphoma therapy, or death from any cause, whichever occurs first, disease-free survival, defined, among patients who achieve a CR, as the time from the first occurrence of a documented CR to relapse, as determined by the investigator on the basis of CT scans alone, or death from any cause, whichever occurs first, overall survival, and defined as the time from initiation of study treatment to death from any cause.

All patients enrolled in the dose-escalation phase will receive induction treatment, administered in 21-day cycles. When study treatments are given on the same day, they will be administered sequentially in the following order: venetoclax, obinutuzumab, and polatuzumab vedotin.

Cycle 1:
  Venetoclax 400, 600, or 800 mg by mouth (PO) once daily on Days 1-21
  Obinutuzumab 1000 mg IV on Days 1, 8, and 15
  Polatuzumab vedotin 1.4 or 1.8 mg/kg intravenously (IV) on Day 1

Cycles 2-6:
  Venetoclax 400, 600, or 800 mg PO once daily on Days 1-21
  Obinutuzumab 1000 mg IV on Day 1
  Polatuzumab vedotin 1.4 or 1.8 mg/kg IV on Day 1

After completion of induction treatment, patients with FL will continue to receive daily venetoclax treatment (during Month 1) until response is assessed at EOI. Venetoclax will be discontinued if response assessments at EOI indicate that a patient is not eligible for post-induction treatment (referred to as maintenance). Patients who achieve a CR, PR, or SD at EOI will receive maintenance treatment with obinutuzumab and venetoclax. Polatuzumab vedotin will not be given as maintenance treatment. Maintenance treatment will continue until disease progression or unacceptable toxicity for up to 24 months. When study treatments are given on the same day, venetoclax will be administered prior to obinutuzumab.

Treatments will be administered as follows:
  Venetoclax 400, 600, or 800 mg PO once daily for 8 months (Months 1-8)
  Obinutuzumab 1000 mg IV on Day 1 of every other month (i.e., every 2 months) for 24 months, starting with Month 2 (e.g., Months 2, 4, 6, 8, etc.).

A 3+3 dose-escalation schema will be used. The obinutuzumab dose will remain fixed at 1000 mg during the dose-escalation phase. The starting doses in Cohort 1 are 1.4 mg/kg for polatuzumab vedotin and 400 mg for venetoclax. In Cohorts 2-6, dose escalation of polatuzumab vedotin and venetoclax will proceed in increments that parallel the magnitude of dose increases tested in ongoing Phase Ib trials. For polatuzumab vedotin, there are 2 possible dose levels: 1.4 or 1.8 mg/kg. For venetoclax, there are 3 possible dose levels: 400, 600, or 800 mg. Intrapatient dose escalation is not allowed.

All patients enrolled in the expansion phase will receive induction treatment, administered in 21-day cycles. When study treatments are given on the same day, they will be administered sequentially in the following order: venetoclax, obinutuzumab, and polatuzumab vedotin.

Cycle 1:
  Venetoclax at the RP2D (mg) PO once daily on Days 1-21
  Obinutuzumab 1000 mg IV on Days 1, 8, and 15
  Polatuzumab vedotin at the RP2D (mg/kg) IV on Day 1

Cycles 2-6:
  Venetoclax at the RP2D (mg) PO once daily on Days 1-21
  Obinutuzumab 1000 mg IV on Day 1
  Polatuzumab vedotin at the RP2D (mg/kg) IV on Day 1

After completion of induction treatment, patients will continue to receive daily venetoclax treatment (during Month 1) until response is assessed at EOI. Venetoclax will be discontinued if response assessments at EOI indicate that a patient is not eligible for post-induction treatment. Patients with DLBCL who achieve a CR or PR at EOI will receive post-induction treatment (referred to as consolidation) with obinutuzumab and venetoclax, and patients with FL who achieve a CR, PR, or SD at EOI will receive post-induction treatment (referred to as maintenance) with obinutuzumab and venetoclax. Polatuzumab vedotin will not be given as post-induction treatment. Post-induction treatment will continue until disease progression or unacceptable toxicity for up to 8 months for consolidation treatment or 24 months for maintenance treatment. When study treatments are given on the same day, venetoclax will be administered prior to obinutuzumab.

Diffuse Large B-Cell Lymphoma: Consolidation treatment consisting of the following, administered for 8 months (Months 1-8):

Venetoclax at the RP2D (mg) PO once daily for 8 months (Months 1-8)

Obinutuzumab 1000 mg IV on Day 1 of every other month (i.e., every 2 months), starting with Month 2 (i.e., Months 2, 4, 6, and 8)

Follicular Lymphoma: Maintenance treatment consisting of the following, administered for 24 months (Months 1-24):

Venetoclax at the RP2D (mg) PO once daily for 8 months (Months 1-8)

Obinutuzumab 1000 mg IV on Day 1 of every other month (i.e., every 2 months) for 24 months, starting with Month 2 (e.g., Months 2, 4, 6, 8, etc.).

Inclusion Criteria: Patients must meet the following criteria for study entry: signed Informed Consent Form, age ≥18 years, Eastern Cooperative Oncology Group Performance Status of 0, 1, or 2, for patients enrolled in the dose-escalation phase: R/R FL after treatment with at least 1 prior chemoimmunotherapy regimen that included an anti-CD20 monoclonal antibody and for which no other more appropriate treatment option exists, as determined by the investigator, for patients enrolled in the expansion phase: B-cell lymphoma classified as either of the following: —R/R FL after treatment with at least 1 prior chemoimmunotherapy regimen that included an anti-CD20 monoclonal antibody and for which no other more appropriate treatment option exists, as determined by the investigator—R/R DLBCL after treatment with at least 1 prior chemoimmunotherapy regimen that included an anti-CD20 monoclonal antibody, with no curative option as determined by the investigator, histologically documented CD20-positive non-Hodgkin's lymphoma as determined by the local laboratory, fluorodeoxyglucose-avid lymphoma (i.e., PET-positive lymphoma), at least one bi-dimensionally measurable lesion (>1.5 cm in its largest dimension by CT scan or magnetic resonance imaging), availability of a representative tumor specimen and the corresponding pathology report for retrospective central confirmation of the diagnosis of FL or DLBCL. If the archival tissue is unavailable or unacceptable, a pretreatment core, excisional, or incisional tumor biopsy is required. Cytological or fine-needle aspiration samples are not acceptable. If the patient received anti-lymphoma treatment between the time of the most recent available biopsy and initiation of study treatment, a core-needle biopsy is strongly recommended.

Exclusion Criteria: Patients who meet any of the following criteria will be excluded from study entry: known CD20-negative status at relapse or progression, prior allogeneic stem cell transplant (SCT), completion of autologous SCT within 100 days prior to Day 1 of Cycle 1, prior standard or investigational anti-cancer therapy as specified: —Radioimmunoconjugate within 12 weeks prior to Day 1 of Cycle 1, —Monoclonal antibody or antibody-drug conjugate therapy within 4 weeks prior to Day 1 of Cycle 1, and —Radiotherapy, chemotherapy, hormonal therapy, or targeted small-molecule therapy within 2 weeks prior to Day 1 of Cycle 1, clinically significant toxicity (other than alopecia) from prior therapy that has not resolved to Grade ≤2 (per NCI CTCAE v4.0) prior to Day 1 of Cycle 1, current Grade >1 peripheral neuropathy, •CNS lymphoma or leptomeningeal infiltration, treatment with systemic corticosteroids >20 mg/day prednisone or equivalent, patients who are receiving corticosteroids ≤20 mg/day prednisone or equivalent must be documented to be on a stable dose for at least 4 weeks prior to Day 1 of Cycle 1. If corticosteroid treatment is urgently required for lymphoma symptom control prior to the start of study treatment, up to 100 mg/day of prednisone or equivalent can be given for a maximum of 5 days, but all tumor assessments must be completed prior to start of corticosteroid treatment. History of severe allergic or anaphylactic reaction to humanized or murine monoclonal antibodies known sensitivity or allergy to murine products or any component of the obinutuzumab, polatuzumab vedotin, or venetoclax formulations, active bacterial, viral, fungal, or other infection, caution should be exercised when considering the use of obinutuzumab in patients with a history of recurring or chronic infections, requirement for warfarin treatment (because of potential drug-drug interactions that may increase the exposure of warfarin), treatment with the following agents within 7 days prior to the first dose of venetoclax: —Strong CYP3A inhibitors such as fluconazole, ketoconazole, and clarithromycin and —Strong CYP3A inducers such as rifampin and carbamazepine, consumption of grapefruit, grapefruit products, Seville oranges (including marmalade that contains Seville oranges), or star fruit within 3 days prior to the first dose of venetoclax, clinically significant history of liver disease, including viral or other hepatitis, current alcohol abuse, or cirrhosis, positive for hepatitis B surface antigen, total hepatitis B core antibody, or hepatitis C virus antibody at screening, known history of HIV positive status, for patients with unknown HIV status, HIV testing will be performed at screening if required by local regulations, history of progressive multifocal leukoencephalopathy, vaccination with a live virus vaccine within 28 days prior to Day 1 of Cycle 1, history of other malignancy that could affect compliance with the protocol or interpretation of results, with the exception of the following: —Curatively treated carcinoma in situ of the cervix, good-prognosis ductal carcinoma in situ of the breast, basal- or squamous-cell skin cancer, Stage I melanoma, or low-grade, early-stage localized prostate cancer —Any previously treated malignancy that has been in remission without treatment for ≥2 years prior to enrollment, evidence of any significant, uncontrolled concomitant disease that could affect compliance with the protocol or interpretation of results, including significant cardiovascular disease (such as New York Heart Association Class III or IV cardiac disease, myocardial infarction within the previous 6 months, unstable arrhythmia, or unstable angina) or significant pulmonary disease (such as obstructive pulmonary disease or history of bronchospasm), major surgical procedure other than for diagnosis within 28 days prior to Day 1 of Cycle 1, or anticipation of a major surgical procedure during the course of the study, inadequate hematologic function (unless due to underlying lymphoma), defined as follows: —Hemoglobin <9 g/dL, —ANC <1.5×10$^9$/L, and —Platelet count <75×10$^9$/L.

Example 8—Anti-CD79b Immunoconjugate in Combination with Lenalidomide

This study will evaluate the safety, efficacy, and pharmacokinetics of induction treatment consisting of obinutuzumab (GA101 or G) in combination with polatuzumab vedotin (anti-CD79b(huMA79b.v23)-MC-vc-PAB-MMAE ADC (DCDS4501A) or pola) and lenalidomide (Len) (G+Pola+Len) in patients with relapsed or refractory follicular lymphoma (FL) or diffuse large B-cell lymphoma (DLBCL), followed by post induction treatment with obinutuzumab in combination with lenalidomide in patients with FL who achieve a complete response (CR), partial response (PR), or stable disease at end of induction (EOI) and in patients with DLBCL who achieve a CR or PR at EOI. Specific objectives and corresponding endpoints for the study are outlined below.

Response will be determined on the basis of positron emission tomography (PET) and computed tomography (CT) scans or CT scans alone, using Revised Lugano Response Criteria for Malignant Lymphoma, hereinafter referred to as the Lugano 2014 criteria. Response will be determined by an Independent Review Committee (IRC) and by the investigator.

Primary Efficacy Objective: The primary efficacy objective for this study is to evaluate the efficacy of induction treatment with G+Pola+Len on the basis of the following endpoint: CR at EOI, as determined by the IRC on the basis of PET-CT scans.

Secondary Efficacy Objectives: The secondary efficacy objective for this study is to evaluate the efficacy of induction treatment with G+Pola+Len on the basis of the following endpoints: CR at EOI, as determined by the investigator on the basis of PET-CT scans, CR at EOI, as determined by the investigator on the basis of CT scans alone, Objective response (defined as a CR or PR) at EOI, as determined by the IRC and by the investigator on the basis of PET-CT scans, Objective response (defined as a CR or PR) at EOI, as determined by the IRC and by the investigator on the basis of CT scans alone, Best response of CR or PR during the study, as determined by the investigator on the basis of CT scans alone.

Exploratory Efficacy Objective: The exploratory efficacy objective for this study is to evaluate the long-term efficacy of G+Pola+Len on the basis of the following endpoints: for patients who have positive PET scans at EOJ: CR at 12 months, as determined by the IRC and by the investigator on the basis of PET-CT scans, PFS, defined as the time from initiation of study treatment to first occurrence of disease progression or relapse, as determined by investigator on the basis of CT scans alone, or death from any cause, EFS, defined as the time from initiation of study treatment to any treatment failure, including disease progression or relapse, as determined by investigator on the basis of CT scans alone, initiation of new anti-lymphoma therapy, or death from any cause, whichever occurs first, disease-free survival, defined, among patients achieving a CR, as the time from the first occurrence of a documented CR to relapse, as determined by the investigator on the basis of CT scans alone, or death from any cause, whichever occurs first, and overall survival, defined as the time from initiation of study treatment to death from any cause.

Inclusion Criteria: Patients must meet the following criteria for study entry: signed Informed Consent Form, age ≥18 years, Eastern Cooperative Oncology Group Performance Status of 0, 1, or 2. For patients enrolled in the dose-escalation phase: relapsed or refractory FL after treatment with at least one prior chemoimmunotherapy regimen that included an anti-CD20 monoclonal antibody and for which no other more appropriate treatment option exists as determined by the investigator. For patients enrolled in the expansion phase: lymphoma classified as either of the following: relapsed or refractory FL after treatment with at least one prior chemoimmunotherapy regimen that included an anti-CD20 monoclonal antibody and for which no other more appropriate treatment option exists as determined by the investigator, relapsed or refractory DLBCL after treatment with at least one prior chemoimmunotherapy regimen in patients who are not eligible for autologous stem-cell transplantation or who have experienced disease progression following treatment with high-dose chemotherapy plus autologous stem-cell transplantation, histologically documented CD20-positive B-cell lymphoma as determined by the local laboratory, fluorodeoxyglucose-avid lymphoma (i.e., PET-positive lymphoma), at least one bi-dimensionally measurable lesion (>1.5 cm in its largest dimension by CT scan or magnetic resonance imaging), availability of a representative tumor specimen and the corresponding pathology report for retrospective central confirmation of the diagnosis of FL or DLBCL. If the archival tissue is unavailable or unacceptable, a pretreatment core-needle, excisional, or incisional tumor biopsy is required. Cytological or fine-needle aspiration samples are not acceptable.

Exclusion Criteria: Patients who meet any of the following criteria will be excluded from study entry: known CD20-negative status at relapse or progression, central nervous system lymphoma or leptomeningeal infiltration, prior allogeneic stem-cell transplantation (SCT), completion of autologous SCT within 100 days prior to Day 1 of Cycle 1, history of resistance to lenalidomide or response duration of <1 year (for patients who had a response to a prior lenalidomide-containing regimen), prior standard or investigational anti-cancer therapy as specified: Lenalidomide, fludarabine, or alemtuzumab within 12 months prior to Day 1 of Cycle1, radioimmunoconjugate within 12 weeks prior to Day 1 of Cycle 1, monoclonal antibody or antibody-drug conjugate therapy within 4 weeks prior to Day 1 of Cycle 1, radiotherapy, chemotherapy, hormonal therapy, or targeted small-molecule therapy within 2 weeks prior to Day 1 of Cycle 1, clinically significant toxicity (other than alopecia) from prior therapy that has not resolved to Grade ≤2 (per NCI CTCAE, Version 4.0) prior to Day 1 of Cycle 1, treatment with systemic immunosuppressive medications, including, but not limited to, prednisone, azathioprine, methotrexate, thalidomide, and anti-tumor necrosis factor agents within 2 weeks prior to Day 1 of Cycle 1. Treatment with inhaled corticosteroids and mineralocorticoids is permitted, if corticosteroid treatment is urgently required for lymphoma symptom control prior to the start of study treatment, up to 100 mg/day of prednisone or equivalent can be given for a maximum of 5 days, but all tumor assessments must be completed prior to initiation of corticosteroid treatment, history of severe allergic or anaphylactic reaction to humanized or murine monoclonal antibodies, known sensitivity or allergy to murine products or any component of obinutuzumab, polatuzumab vedotin, or lenalidomide formulations, history of erythema multiforme, Grade ≥3 rash, or desquamation (blistering) following prior treatment with immunomodulatory derivatives such as thalidomide and lenalidomide, active bacterial, viral, fungal, or other infection, caution should be exercised when considering the use of obinutuzumab in patients with a history of recurring or chronic infections, positive for hepatitis B surface antigen, total hepatitis B core antibody, or hepatitis C virus antibody at screening, known history of HIV positive status, history of progressive multifocal leukoencephalopathy, vaccination with a live virus vaccine within 28 days prior to Day 1 of Cycle 1, history of other malignancy that could affect compliance with the protocol or interpretation of results, with the exception of the following: curatively treated carcinoma in situ of the cervix; good-prognosis ductal carcinoma in situ of the breast; basal- or squamous-cell skin cancer; Stage I melanoma; or low-grade, early-stage localized prostate cancer, any previously treated malignancy that has been in remission without treatment for ≥2 years prior to enrollment, contraindication to treatment for TE prophylaxis, Grade ≥2 neuropathy, evidence of any significant, uncontrolled concomitant disease that could affect compliance with the protocol or interpretation of results, including significant cardiovascular disease (such as New York Heart Association Class III or IV cardiac disease, myocardial infarction within the previous 6 months, unstable arrhythmia, or unstable angina) or significant pulmonary disease (such as obstructive pulmonary disease or history of bronchospasm), major surgical procedure other than for diagnosis within 28 days prior to Day 1 of Cycle 1 or anticipation of a major surgical procedure during the course of the study, inadequate hematologic function (unless due to underlying lymphoma), defined as follows: Hemoglobin <9 g/dL, ANC <1.5×10⁹/L, Platelet count <75×10⁹/L, any of the following abnormal laboratory values (unless due to underlying lymphoma): calculated creatinine clearance <60 mL/min (using the Cockcroft-Gault formula), AST or ALT >2.5× upper limit of normal (ULN), serum total bilirubin >1.5×ULN (or >3×ULN for patients with Gilbert syndrome), INR or PT >1.5×ULN in the absence of therapeutic anticoagulation, or PTT or aPTT >1.5×ULN in the absence of a lupus anticoagulant.

Obinutuzumab: Induction-Patients will receive obinutuzumab 1000 mg intravenously on Days 1, 8, and 15 of Cycle 1 and on Day 1 of each subsequent 28-day cycle for up to 6 cycles. Post-Induction—For consolidation treatment, patients with DLBCL will receive obinutuzumab 1000 mg intravenously on Day 1 of every other month for approximately 6 months of additional treatment. For maintenance treatment, patients with FL will receive obinutuzumab 1000 mg intravenously on Day 1 of every other month for approximately 24 months of additional treatment.

Polatuzumab Vedotin: Induction-Patients will receive polatuzumab vedotin 1.4 or 1.8 mg/kg intravenously on Day 1 of each 28-day cycle for up to 6 cycles. •In the Phase Ib portion of the study, the total dose of polatuzumab vedotin for each patient will depend on dose-level assignment and the patient's weight on Day 1 of Cycle 1 (or within 96 hours before Day 1 of Cycle 1). In the Phase II portion of the study, the total dose of polatuzumab vedotin for each patient will depend on the RP2D established in the Phase Ib portion and the patient's weight on Day 1 of Cycle 1 (or within 96 hours before Day 1 of Cycle 1). Post-Induction-No polatuzumab vedotin will be administered.

Lenalidomide: Induction-Patients will receive lenalidomide 10, 15, or 20 mg orally once daily on Days 1-21 of each 28-day cycle for up to 6 cycles. In the Phase Ib portion of the study, the dose of lenalidomide for each patient will depend on dose-level assignment on Day 1 of Cycle 1. In the Phase II portion of the study, the dose of lenalidomide for each patient will depend on the RP2D established in the Phase Ib portion of the study. Post-Induction-Patients will receive lenalidomide 10 mg orally once daily on Days 1-21 of each month. For consolidation treatment for patients with DLBCL will receive lenalidomide 10 mg orally once daily on Days 1-21 of each month (starting Month 1 and continuing through Month 6) for approximately 6 months of additional treatment. For maintenance treatment, patients with FL will receive lenalidomide 10 mg orally once daily on Days 1-21 of each month (starting Month 1 and continuing through Month 12) for approximately 12 months of additional treatment.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| NAME | SEQUENCE | SEQ ID NO |
|---|---|---|
| Human CD79b precursor; Acc. No. NP_000617.1; signal sequence = amino acids 1 to 28 | RFIARKRGFT VKMHCYMNSA SGNVSWLWKQ EMDENPQQLK LEKGRMEESQ NESLATLTIQ GIRFEDNGIY FCQQKCNNTS EVYQGCGTEL RVMGFSTLAQ LKQRNTLKDG IIMIQTLLII LFIIVPIFLL LDKDDSKAGM EEDHTYEGLD IDQTATYEDI VTLRTGEVKW SVGEHPGQE | 1 |
| Human mature CD79b, without signal sequence; amino acids 29 to 229 | AR SEDRYRNPKG SACSRIWQSP RFIARKRGFT VKMHCYMNSA SGNVSWLWKQ EMDENPQQLK LEKGRMEESQ NESLATLTIQ GIRFEDNGIY FCQQKCNNTS EVYQGCGTEL RVMGFSTLAQ LKQRNTLKDG IIMIQTLLII LFIIVPIFLL LDKDDSKAGM EEDHTYEGLD IDQTATYEDI VTLRTGEVKW SVGEHPGQE | 2 |
| VH of mMAb anti-CD20 antibody B-Ly1 | Gly Pro Glu Val Lys Pro Gly Ala Ser Val Lys Ile Ser Cys Lys 1 5 10 15 Ala Ser Gly Tyr Ala Phe Ser Tyr Ser Trp Met Asn Trp Val Lys Leu 20 25 30 Arg Pro Gly Gln Gly Leu Glu Trp Ile Gly Arg Ile Phe Pro Gly Asp 35 40 45 GLy Asp Thr Asp Tyr Asn Gly Lys Phe Lys Gly Lys Ala Thr Leu Thr 50 55 60 Ala Asp Lys Ser Ser Asn Thr Ala Tyr Met Gln Leu Thr Ser Leu Thr 65 70 75 80 Ser Val Asp Ser Ala Val Tyr Leu Cys Ala Arg Asn Val Phe Asp Gly 85 90 95 Tyr Trp Leu Val Tyr Trp Gly Gln Gly Thr Leu Val Thr Val Ser Ala 100 105 110 | 3 |
| VL of mMAb anti-CD20 antibody B-Ly1 | Asn Pro Val Thr Leu Gly Thr Ser Ala Ser Ile Ser Cys Arg Ser Ser 1 5 10 15 Lys Ser Leu Leu His Ser Asn Gly Ile Thr Tyr Leu Tyr Trp Tyr Leu 20 25 30 Gln Lys Pro Gly Gln Ser Pro Gln Leu Leu Ile Tyr Gln Met Ser Asn 35 40 45 | 4 |

| NAME | SEQUENCE | SEQ ID NO |
|---|---|---|
| | Leu Val Ser Gly Val Pro Asp Arg Phe Ser Ser Gly Ser Gly Thr<br>        50                      55                      60<br>Asp Phe Thr Leu Arg Ile Ser Arg Val Glu Ala Glu Asp Val Gly Val<br>65                  70                      75                      80<br>Tyr Tyr Cys Ala Gln Asn Leu Glu Leu Pro Tyr Thr Phe Gly Gly Gly<br>                 85                      90                      95<br>Thr Lys Leu Glu Ile Lys Arg<br>                 100 | |
| GA101 HVR-H1 | Gly Tyr Ala Phe Ser Tyr<br>1                5 | 5 |
| GA101 HVR-H2 | Phe Pro Gly Asp Gly Asp Thr Asp<br>1                5 | 6 |
| GA101 HVR-H3 | Asn Val Phe Asp Gly Tyr Trp Leu Val Tyr<br>1                5                      10 | 7 |
| GA101 HVR-L1 | Arg Ser Ser Lys Ser Leu Leu His Ser Asn Gly Ile Thr Tyr Leu Tyr<br>1                5                      10                      15 | 8 |
| GA101 HVR-L2 | Gln Met Ser Asn Leu Val Ser<br>1                5 | 9 |
| GA101 HVR-L3 | Ala Gln Asn Leu Glu Leu Pro Tyr Thr<br>1                5 | 10 |
| GA101 VH | Gln Val Gln Leu Val Gln Ser Gly Ala Glu Val Lys Lys Pro Gly Ser<br>1                5                      10                      15<br>Ser Val Lys Val Ser Cys Lys Ala Ser Gly Tyr Ala Phe Ser Tyr Ser<br>                 20                      25                      30<br>Trp Ile Asn Trp Val Arg Gln Ala Pro Gly Gln Gly Leu Glu Trp Met<br>                 35                      40                      45<br>Gly Arg Ile Phe Pro Gly Asp Gly Asp Thr Asp Tyr Asn Gly Lys Phe<br>                 50                      55                      60<br>Lys Gly Arg Val Thr Ile Thr Ala Asp Lys Ser Thr Ser Thr Ala Tyr<br>65                  70                      75                      80<br>Met Glu Leu Ser Ser Leu Arg Ser Glu Asp Thr Ala Val Tyr Tyr Cys<br>                 85                      90                      95<br>Ala Arg Asn Val Phe Asp Gly Tyr Trp Leu Val Tyr Trp Gly Gln Gly<br>                 100                     105                   110<br>Thr Leu Val Thr Val Ser Ser<br>                 115 | 11 |
| GA101 VL | Asp Ile Val Met Thr Gln Thr Pro Leu Ser Leu Pro Val Thr Pro Gly<br>1                5                      10                      15<br>Glu Pro Ala Ser Ile Ser Cys Arg Ser Ser Lys Ser Leu Leu His Ser<br>                 20                      25                      30<br>Asn Gly Ile Thr Tyr Leu Tyr Trp Tyr Leu Gln Lys Pro Gly Gln Ser<br>                 35                      40                      45<br>Pro Gln Leu Leu Ile Tyr Gln Met Ser Asn Leu Val Ser Gly Val Pro<br>                 50                      55                      60<br>Asp Arg Phe Ser Gly Ser Gly Ser Gly Thr Asp Phe Thr Leu Lys Ile<br>65                  70                      75                      80<br>Ser Arg Val Glu Ala Glu Asp Val Gly Val Tyr Tyr Cys Ala Gln Asn<br>                 85                      90                      95<br>Leu Glu Leu Pro Tyr Thr Phe Gly Gly Gly Thr Lys Val Glu Ile Lys<br>                 100                     105                   110<br>Arg Thr Val<br>                 115 | 12 |
| GA101 Heavy Chain | Gln Val Gln Leu Val Gln Ser Gly Ala Glu Val Lys Lys Pro Gly Ser<br>1                5                      10                      15<br>Ser Val Lys Val Ser Cys Lys Ala Ser Gly Tyr Ala Phe Ser Tyr Ser<br>                 20                      25                      30<br>Trp Ile Asn Trp Val Arg Gln Ala Pro Gly Gln Gly Leu Glu Trp Met<br>                 35                      40                      45<br>Gly Arg Ile Phe Pro Gly Asp Gly Asp Thr Asp Tyr Asn Gly Lys Phe<br>                 50                      55                      60<br>Lys Gly Arg Val Thr Ile Thr Ala Asp Lys Ser Thr Ser Thr Ala Tyr<br>65                  70                      75                      80<br>Met Glu Leu Ser Ser Leu Arg Ser Glu Asp Thr Ala Val Tyr Tyr Cys<br>                 85                      90                      95<br>Ala Arg Asn Val Phe Asp Gly Tyr Trp Leu Val Tyr Trp Gly Gln Gly<br>                 100                     105                   110<br>Thr Leu Val Thr Val Ser Ser Ala Ser Thr Lys Gly Pro Ser Val Phe<br>                 115                     120                   125 | 13 |

| NAME | SEQUENCE | SEQ ID NO |
|---|---|---|
| | Pro Leu Ala Pro Ser Ser Lys Ser Thr Ser Gly Gly Thr Ala Ala Leu<br>130                              135                      140<br>Gly Cys Leu Val Lys Asp Tyr Phe Pro Glu Pro Val Thr Val Ser Trp<br>145                              150                      155                      160<br>Asn Ser Gly Ala Leu Thr Ser Gly Val His Thr Phe Pro Ala Val Leu<br>                      165                      170                      175<br>Gln Ser Ser Gly Leu Tyr Ser Leu Ser Ser Val Val Thr Val Pro Ser<br>                180                      185                      190<br>Ser Ser Leu Gly Thr Gln Thr Tyr Ile Cys Asn Val Asn His Lys Pro<br>      195                      200                      205<br>Ser Asn Thr Lys Val Asp Lys Val Glu Pro Lys Ser Cys Asp Lys<br>210                      215                      220<br>Thr His Thr Cys Pro Pro Cys Pro Ala Pro Glu Leu Leu Gly Gly Pro<br>225                              230                      235                      240<br>Ser Val Phe Leu Phe Pro Pro Lys Pro Lys Asp Thr Leu Met Ile Ser<br>                      245                      250                      255<br>Arg Thr Pro Glu Val Thr Cys Val Val Val Asp Val Ser His Glu Asp<br>                260                      265                      270<br>Pro Glu Val Lys Phe Asn Trp Tyr Val Asp Gly Val Glu Val His Asn<br>            275                      280                      285<br>Ala Lys Thr Lys Pro Arg Glu Glu Gln Tyr Asn Ser Thr Tyr Arg Val<br>290                              295                      300<br>Val Ser Val Leu Thr Val Leu His Gln Asp Trp Leu Asn Gly Lys Glu<br>305                              310                      315                      320<br>Tyr Lys Cys Lys Val Ser Asn Lys Ala Leu Pro Ala Pro Ile Glu Lys<br>                  325                      330                      335<br>Thr Ile Ser Lys Ala Lys Gly Gln Pro Arg Glu Pro Gln Val Tyr Thr<br>                340                      345                      350<br>Leu Pro Pro Ser Arg Asp Glu Leu Thr Lys Asn Gln Val Ser Leu Thr<br>            355                      360                      365<br>Cys Leu Val Lys Gly Phe Tyr Pro Ser Asp Ile Ala Val Glu Trp Glu<br>370                              375                      380<br>Ser Asn Gly Gln Pro Glu Asn Asn Tyr Lys Thr Thr Pro Pro Val Leu<br>385                              390                      395                      400<br>Asp Ser Asp Gly Ser Phe Phe Leu Tyr Ser Lys Leu Thr Val Asp Lys<br>                  405                      410                      415<br>Ser Arg Trp Gln Gln Gly Asn Val Phe Ser Cys Ser Val Met His Glu<br>                420                      425                      430<br>Ala Leu His Asn His Tyr Thr Gln Lys Ser Leu Ser Leu Ser Pro Gly<br>            435                      440                      445 | |
| GA101 Light Chain | Asp Ile Val Met Thr Gln Thr Pro Leu Ser Leu Pro Val Thr Pro Gly<br>1                    5                      10                      15<br>Glu Pro Ala Ser Ile Ser Cys Arg Ser Ser Lys Ser Leu Leu His Ser<br>            20                      25                      30<br>Asn Gly Ile Thr Tyr Leu Tyr Trp Tyr Leu Gln Lys Pro Gly Gln Ser<br>               35                      40                      45<br>Pro Gln Leu Leu Ile Tyr Gln Met Ser Asn Leu Val Ser Gly Val Pro<br>      50                      55                      60<br>Asp Arg Phe Ser Gly Ser Gly Ser Gly Thr Asp Phe Thr Leu Lys Ile<br>65                              70                      75                      80<br>Ser Arg Val Glu Ala Glu Asp Val Gly Val Tyr Tyr Cys Ala Gln Asn<br>               85                      90                      95<br>Leu Glu Leu Pro Tyr Thr Phe Gly Gly Gly Thr Lys Val Glu Ile Lys<br>            100                      105                      110<br>Arg Thr Val Ala Ala Pro Ser Val Phe Ile Phe Pro Pro Ser Asp Glu<br>            115                      120                      125<br>Gln Leu Lys Ser Gly Thr Ala Ser Val Val Cys Leu Leu Asn Asn Phe<br>130                              135                      140<br>Tyr Pro Arg Glu Ala Lys Val Gln Trp Lys Val Asp Asn Ala Leu Gln<br>145                              150                      155                      160<br>Ser Gly Asn Ser Gln Glu Ser Val Thr Glu Gln Asp Ser Lys Asp Ser<br>                165                      170                      175<br>Thr Tyr Ser Leu Ser Ser Thr Leu Thr Leu Ser Lys Ala Asp Tyr Glu<br>                180                      185                      190<br>Lys His Lys Val Tyr Ala Cys Glu Val Thr His Gln Gly Leu Ser Ser<br>            195                      200                      205<br>Pro Val Thr Lys Ser Phe Asn Arg Gly Glu Cys<br>210                      215 | 14 |
| VH of humanized B-Ly1 antibody (B-HH2) | Gln Val Gln Leu Val Gln Ser Gly Ala Glu Val Lys Lys Pro Gly Ser<br>1                    5                      10                      15<br>Ser Val Lys Val Ser Cys Lys Ala Ser Gly Tyr Ala Phe Ser Tyr Ser<br>            20                      25                      30<br>Trp Met Asn Trp Val Arg Gln Ala Pro Gly Gln Gly Leu Glu Trp Met<br>               35                      40                      45 | 15 |

| NAME | SEQUENCE | SEQ ID NO |
|---|---|---|
| | Gly Arg Ile Phe Pro Gly Asp Gly Asp Thr Asp Tyr Asn Gly Lys Phe<br>          50                        55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Tyr Cys<br>                    85                        90                    95<br>Ala Arg Asn Val Phe Asp Gly Tyr Trp Leu Val Tyr Trp Gly Gln Gly<br>            100                        105                      110<br>Thr Leu Val Thr Val Ser Ser<br>            115 | |
| VH of humanized B-Ly1 antibody (B-HH3) | Gln Val Gln Leu Val Gln Ser Gly Ala Glu Val Lys Lys Pro Gly Ser<br>1                      5                    10                    15<br>Ser Val Lys Val Ser Cys Lys Ala Ser Gly Tyr Ala Phe Ser Tyr Ser<br>            20                        25                    30<br>Trp Met Asn Trp Val Arg Gln Ala Pro Gly Gln Gly Leu Glu Trp Met<br>        35                        40                    45<br>Gly Arg Ile Phe Pro Gly Asp Gly Asp Thr Asp Tyr Asn Gly Lys Phe<br>            50                        55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Leu Cys<br>                    85                        90                    95<br>Ala Arg Asn Val Phe Asp Gly Tyr Trp Leu Val Tyr Trp Gly Gln Gly<br>            100                        105                      110<br>Thr Leu Val Thr Val Ser Ser<br>            115 | 16 |
| humanized B-Ly1 Heavy Chain | QVQLVQSGAE VKKPGSSVKV SCKASGYAFS YSWINWVRQA<br>PGQGLEWMGR IFPGDGDTDY NGKFKGRVTI TADKSTSTAY<br>MELSSLRSED TAVYYCARNV FDGYWLVYWG QGTLVTVSSA<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPELLGGP<br>SVFLFPPKPK DTLMISRTPE VTCVVVDVSH EDPEVKFNWY<br>VDGVEVHNAK TKPREEQYNS TYRVVSVLTV LHQDWLNGKE<br>YKCKVSNKAL PAPIEKTISK AKGQPREPQV YTLPPSRDEL<br>TKNQVSLTCL VKGFYPSDIA VEWESNGQPE NNYKTTPPVL<br>DSDGSFFLYS KLTVDKSRWQ QGNVFSCSVM HEALHNHYTQ KSLSLSPG | 17 |
| humanized B-Ly1 Light Chain | DIVMTQTPLS LPVTPGEPAS ISCRSSKSLL HSNGITYLYW<br>YLQKPGQSPQ LLIYQMSNLV SGVPDRFSGS GSGTDFTLKI<br>SRVEAEDVGV YYCAQNLELP YTFGGGTKVE IKRTVAAPSV<br>FIFPPSDEQL KSGTASVVCL LNNFYPREAK VQWKVDNALQ<br>SGNSQESVTE QDSKDSTYSL SSTLTLSKAD YEKHKVYACE<br>VTHQGLSSPV TKSFNRGEC | 18 |
| huMA79bv28 heavy chain variable region | EVQLVESGGG LVQPGGSLRL SCAASGYTFS SYWIEWVRQA<br>PGKGLEWIGE ILPGGGDTNY NEIFKGRATF SADTSKNTAY<br>LQMNSLRAED TAVYYCTRRV PIRLDYWGQG TLVTVSS | 19 |
| huMA79bv28 light chain variable region | DIQLTQSPSS LSASVGDRVT ITCKASQSVD YEGDSFLNWY<br>QQKPGKAPKL LIYAASNLES GVPSRFSGSG SGTDFTLTIS<br>SLQPEDFATY YCQQSNEDPL TFGQGTKVEI KR | 20 |
| huMA79bv28 HVR H1 | GYTFSSYWIE | 21 |
| huMA79bv28 HVR H2 | GEILPGGGDTNYNEIFKG | 22 |
| huMA79bv28 HVR H3 | TRRVPIRLDY | 23 |
| huMA79bv28 HVR L1 | KASQSVDYEGDSFLN | 24 |
| huMA79bv28 HVR L2 | AASNLES | 25 |
| huMA79bv28 HVR L3 | QQSNEDPLT | 26 |

| NAME | SEQUENCE | SEQ ID NO |
|---|---|---|
| huMA79bv28 heavy chain (HC) framework region (FR) 1 | EVQLVESGGGLVQPGGSLRLCAAS | 27 |
| huMA79bv28 HC FR2 | WVRQAPGKGLEWI | 28 |
| huMA79bv28 HC FR3 | RATFSADTSKNTAYLQMNSLRAEDTAVYYC | 29 |
| huMA79bv28 HC FR4 | WGQGTLVTVSS | 30 |
| huMA79bv28 light chain (LC) FR1 | DIQLTQSPSSLSASVGDRVTITC | 31 |
| huMA79bv28 LC FR2 | WYQQKPGKAPKLLIY | 32 |
| huMA79bv28 LC FR3 | GVPSRFSGSGSGTDFTLTISSLQPEDFATYYC | 33 |
| huMA79bv28 LC FR4 | FGQGTKVEIKR | 34 |
| huMA79bv28 light chain (Igκ) | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC | 35 |
| huMA79bv28 heavy chain (IgG1) | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG | 36 |
| huMA79bv28 A118C cysteine engineered heavy chain (IgG1) | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSSCST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG | 37 |
| huMA79bv28 V205C cysteine engineered light chain (Igκ) | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPCT KSFNRGEC | 38 |
| huMA79bv28 S400C cysteine engineered heavy chain (IgG1) | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK | 39 |

| NAME | SEQUENCE | SEQ ID NO |
|---|---|---|
| | CKVSNKALPA PIEKTISKAK GQPREPQVYT LPPSREEMTK<br>NQVSLTCLVK GFYPSDIAVE WESNGQPENN YKTTPPVLDC<br>DGSFFLYSKL TVDKSRWQQG NVFSCSVMHE ALHNHYTQKS LSLSPGK | |
| VH of humanized B-Ly1 antibody (B-HH4) | Gln Val Gln Leu Val Gln Ser Gly Ala Glu Val Lys Lys Pro Gly Ala<br>1               5                   10                  15<br>Ser Val Lys Val Ser Cys Lys Val Ser Gly Tyr Ala Phe Ser Tyr Ser<br>            20                  25                  30<br>Trp Met Asn Trp Val Arg Gln Ala Pro Gly Gln Gly Leu Glu Trp Met<br>        35                  40                  45<br>Gly Arg Ile Phe Pro Gly Asp Gly Asp Thr Asp Tyr Asn Gly Lys Phe<br>            50                  55                  60<br>Lys Gly Arg Val Thr Ile Thr Ala Asp Lys Ser Thr Ser Thr Ala Tyr<br>65                  70                  75                  80<br>Met Glu Leu Ser Ser Leu Arg Ser Glu Asp Thr Ala Val Tyr Tyr Cys<br>            85                  90                  95<br>Ala Arg Asn Val Phe Asp Gly Tyr Trp Leu Val Tyr Trp Gly Gln Gly<br>            100                 105                 110<br>Thr Leu Val Thr Val Ser Ser<br>            115 | 40 |
| VH of humanized B-Ly1 antibody (B-HH5) | Gln Val Gln Leu Val Gln Ser Gly Ala Glu Val Lys Lys Pro Gly Ser<br>1               5                   10                  15<br>Ser Val Lys Val Ser Cys Lys Ala Ser Gly Tyr Ala Phe Ser Tyr Ser<br>            20                  25                  30<br>Trp Met Ser Trp Val Arg Gln Ala Pro Gly Gln Gly Leu Glu Trp Met<br>        35                  40                  45<br>Gly Arg Ile Phe Pro Gly Asp Gly Asp Thr Asp Tyr Asn Gly Lys Phe<br>            50                  55                  60<br>Lys Gly Arg Val Thr Ile Thr Ala Asp Lys Ser Thr Ser Thr Ala Tyr<br>65                  70                  75                  80<br>Met Glu Leu Ser Ser Leu Arg Ser Glu Asp Thr Ala Val Tyr Tyr Cys<br>            85                  90                  95<br>Ala Arg Asn Val Phe Asp Gly Tyr Trp Leu Val Tyr Trp Gly Gln Gly<br>            100                 105                 110<br>Thr Leu Val Thr Val Ser Ser<br>            115 | 41 |
| VH of humanized B-Ly1 antibody (B-HH6) | Gln Val Gln Leu Val Gln Ser Gly Ala Glu Val Lys Lys Pro Gly Ser<br>1               5                   10                  15<br>Ser Val Lys Val Ser Cys Lys Ala Ser Gly Tyr Ala Phe Ser Tyr Ser<br>            20                  25                  30<br>Trp Ile Asn Trp Val Arg Gln Ala Pro Gly Gln Gly Leu Glu Trp Met<br>        35                  40                  45<br>Gly Arg Ile Phe Pro Gly Asp Gly Asp Thr Asp Tyr Asn Gly Lys Phe<br>            50                  55                  60<br>Lys Gly Arg Val Thr Ile Thr Ala Asp Lys Ser Thr Ser Thr Ala Tyr<br>65                  70                  75                  80<br>Met Glu Leu Ser Ser Leu Arg Ser Glu Asp Thr Ala Val Tyr Tyr Cys<br>            85                  90                  95<br>Ala Arg Asn Val Phe Asp Gly Tyr Trp Leu Val Tyr Trp Gly Gln Gly<br>            100                 105                 110<br>Thr Leu Val Thr Val Ser Ser<br>            115 | 42 |
| VH of humanized B-Ly1 antibody (B-HH7) | Gln Val Gln Leu Val Gln Ser Gly Ala Glu Val Lys Lys Pro Gly Ser<br>1               5                   10                  15<br>Ser Val Lys Val Ser Cys Lys Ala Ser Gly Tyr Ala Phe Ser Tyr Ser<br>            20                  25                  30<br>Trp Ile Ser Trp Val Arg Gln Ala Pro Gly Gln Gly Leu Glu Trp Met<br>        35                  40                  45<br>Gly Arg Ile Phe Pro Gly Asp Gly Asp Thr Asp Tyr Asn Gly Lys Phe<br>            50                  55                  60<br>Lys Gly Arg Val Thr Ile Thr Ala Asp Lys Ser Thr Ser Thr Ala Tyr<br>65                  70                  75                  80<br>Met Glu Leu Ser Ser Leu Arg Ser Glu Asp Thr Ala Val Tyr Tyr Cys<br>            85                  90                  95<br>Ala Arg Asn Val Phe Asp Gly Tyr Trp Leu Val Tyr Trp Gly Gln Gly<br>            100                 105                 110<br>Thr Leu Val Thr Val Ser Ser<br>            115 | 43 |
| VH of humanized B-Ly1 antibody (B-HH8) | Gln Val Gln Leu Val Gln Ser Gly Ala Glu Val Lys Lys Pro Gly Ala<br>1               5                   10                  15<br>Ser Val Lys Val Ser Cys Lys Ala Ser Gly Tyr Thr Phe Thr Tyr Ser<br>            20                  25                  30 | 44 |

| NAME | SEQUENCE | SEQ ID NO |
|------|----------|-----------|
| | Trp Met Asn Trp Val Arg Gln Ala Pro Gly Gln Gly Leu Glu Trp Met<br>        35                        40                  45<br>Gly Arg Ile Phe Pro Gly Asp Gly Asp Thr Asp Tyr Asn Gly Lys Phe<br>    50                       55                      60<br>Lys Gly Arg Val Thr Ile Thr Ala Asp Lys Ser Thr Ser Thr Ala Tyr<br>65                        70                        75                      80<br>Met Glu Leu Ser Ser Leu Arg Ser Glu Asp Thr Ala Val Tyr Tyr Cys<br>                        85                        90                      95<br>Ala Arg Asn Val Phe Asp Gly Tyr Trp Leu Val Tyr Trp Gly Gln Gly<br>            100                    105                  110<br>Thr Leu Val Thr Val Ser Ser<br>            115 | |
| VH of humanized B-Ly1 antibody (B-HH9) | Gln Val Gln Leu Val Gln Ser Gly Ala Glu Val Lys Lys Pro Gly Ala<br>1                    5                        10                      15<br>Ser Val Lys Val Ser Cys Lys Ala Ser Gly Tyr Thr Phe Ser Tyr Ser<br>                20                        25                      30<br>Trp Met Asn Trp Val Arg Gln Ala Pro Gly Gln Gly Leu Glu Trp Met<br>            35                        40                  45<br>Gly Arg Ile Phe Pro Gly Asp Gly Asp Thr Asp Tyr Asn Gly Lys Phe<br>    50                       55                      60<br>Lys Gly Arg Val Thr Ile Thr Ala Asp Lys Ser Thr Ser Thr Ala Tyr<br>65                        70                        75                      80<br>Met Glu Leu Ser Ser Leu Arg Ser Glu Asp Thr Ala Val Tyr Tyr Cys<br>                        85                        90                      95<br>Ala Arg Asn Val Phe Asp Gly Tyr Trp Leu Val Tyr Trp Gly Gln Gly<br>            100                    105                  110<br>Thr Leu Val Thr Val Ser Ser<br>            115 | 45 |
| VH of humanized B-Ly1 antibody (B-HL8) | Glu Val Gln Leu Val Glu Ser Gly Gly Gly Leu Val Lys Pro Gly Gly<br>1                    5                        10                      15<br>Ser Leu Arg Leu Ser Cys Ala Ala Ser Gly Phe Thr Phe Ser Tyr Ser<br>                20                        25                      30<br>Trp Met Asn Trp Val Arg Gln Ala Pro Gly Lys Gly Leu Glu Trp Val<br>            35                        40                  45<br>Gly Arg Ile Phe Pro Gly Asp Gly Asp Thr Asp Tyr Asn Gly Lys Phe<br>    50                       55                      60<br>Lys Gly Arg Val Thr Ile Thr Ala Asp Lys Ser Thr Ser Thr Ala Tyr<br>65                        70                        75                      80<br>Met Glu Leu Ser Ser Leu Arg Ser Glu Asp Thr Ala Val Tyr Tyr Cys<br>                        85                        90                      95<br>Ala Arg Asn Val Phe Asp Gly Tyr Trp Leu Val Tyr Trp Gly Gln Gly<br>            100                    105                  110<br>Thr Leu Val Thr Val Ser Ser<br>            115 | 46 |
| VH of humanized B-Ly1 antibody (B-HL10) | Glu Val Gln Leu Val Glu Ser Gly Gly Gly Leu Val Lys Pro Gly Gly<br>1                    5                        10                      15<br>Ser Leu Arg Leu Ser Cys Ala Ala Ser Gly Phe Ala Phe Ser Tyr Ser<br>                20                        25                      30<br>Trp Met Asn Trp Val Arg Gln Ala Pro Gly Lys Gly Leu Glu Trp Val<br>            35                        40                  45<br>Gly Arg Ile Phe Pro Gly Asp Gly Asp Thr Asp Tyr Asn Gly Lys Phe<br>    50                       55                      60<br>Lys Gly Arg Val Thr Ile Thr Ala Asp Lys Ser Thr Ser Thr Ala Tyr<br>65                        70                        75                      80<br>Met Glu Leu Ser Ser Leu Arg Ser Glu Asp Thr Ala Val Tyr Tyr Cys<br>                        85                        90                      95<br>Ala Arg Asn Val Phe Asp Gly Tyr Trp Leu Val Tyr Trp Gly Gln Gly<br>            100                    105                  110<br>Thr Leu Val Thr Val Ser Ser<br>            115 | 47 |
| VH of humanized B-Ly1 antibody (B-HL11) | Gln Val Gln Leu Val Glu Ser Gly Gly Gly Leu Val Lys Pro Gly Gly<br>1                    5                        10                      15<br>Ser Leu Arg Leu Ser Cys Ala Ala Ser Gly Phe Thr Phe Ser Tyr Ser<br>                20                        25                      30<br>Trp Met Asn Trp Val Arg Gln Ala Pro Gly Lys Gly Leu Glu Trp Val<br>            35                        40                  45<br>Gly Arg Ile Phe Pro Gly Asp Gly Asp Thr Asp Tyr Asn Gly Lys Phe<br>    50                       55                      60<br>Lys Gly Arg Val Thr Ile Thr Ala Asp Lys Ser Thr Ser Thr Ala Tyr<br>65                        70                        75                      80<br>Met Glu Leu Ser Ser Leu Arg Ser Glu Asp Thr Ala Val Tyr Tyr Cys<br>                        85                        90                      95 | 48 |

-continued

| NAME | SEQUENCE | SEQ ID NO |
|---|---|---|
| | Ala Arg Asn Val Phe Asp Gly Tyr Trp Leu Val Tyr Trp Gly Gln Gly<br>           100                    105                    110<br>Thr Leu Val Thr Val Ser Ser<br>           115 | |
| VH of humanized B-Ly1 antibody (B-HL12) | Glu Val Gln Leu Val Glu Ser Gly Ala Gly Leu Val Lys Pro Gly Gly<br>1              5                    10                    15<br>Ser Leu Arg Leu Ser Cys Ala Ala Ser Gly Phe Thr Phe Ser Tyr Ser<br>           20                    25                    30<br>Trp Met Asn Trp Val Arg Gln Ala Pro Gly Lys Gly Leu Glu Trp Met<br>           35                    40                    45<br>Gly Arg Ile Phe Pro Gly Asp Gly Asp Thr Asp Tyr Asn Gly Lys Phe<br>           50                    55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Tyr Cys<br>                85                    90                    95<br>Ala Arg Asn Val Phe Asp Gly Tyr Trp Leu Val Tyr Trp Gly Gln Gly<br>           100                    105                    110<br>Thr Leu Val Thr Val Ser Ser<br>           115 | 49 |
| VH of humanized B-Ly1 antibody (B-HL13) | Glu Val Gln Leu Val Glu Ser Gly Gly Gly Val Val Lys Pro Gly Gly<br>1              5                    10                    15<br>Ser Leu Arg Leu Ser Cys Ala Ala Ser Gly Phe Thr Phe Ser Tyr Ser<br>           20                    25                    30<br>Trp Met Asn Trp Val Arg Gln Ala Pro Gly Lys Gly Leu Glu Trp Met<br>           35                    40                    35<br>Gly Arg Ile Phe Pro Gly Asp Gly Asp Thr Asp Tyr Asn Gly Lys Phe<br>           50                    55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Tyr Cys<br>                85                    90                    95<br>Ala Arg Asn Val Phe Asp Gly Tyr Trp Leu Val Tyr Trp Gly Gln Gly<br>           100                    105                    110<br>Thr Leu Val Thr Val Ser Ser<br>           115 | 50 |
| VH of humanized B-Ly1 antibody (B-HL14) | Glu Val Gln Leu Val Glu Ser Gly Gly Gly Leu Lys Lys Pro Gly Gly<br>1              5                    10                    15<br>Ser Leu Arg Leu Ser Cys Ala Ala Ser Gly Phe Thr Phe Ser Tyr Ser<br>           20                    25                    30<br>Trp Met Asn Trp Val Arg Gln Ala Pro Gly Lys Gly Leu Glu Trp Met<br>           35                    40                    45<br>Gly Arg Ile Phe Pro Gly Asp Gly Asp Thr Asp Tyr Asn Gly Lys Phe<br>           50                    55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Tyr Cys<br>                85                    90                    95<br>Ala Arg Asn Val Phe Asp Gly Tyr Trp Leu Val Tyr Trp Gly Gln Gly<br>           100                    105                    110<br>Thr Leu Val Thr Val Ser Ser<br>           115 | 51 |
| VH of humanized B-Ly1 antibody (B-HL15) | Glu Val Gln Leu Val Glu Ser Gly Gly Gly Leu Val Lys Pro Gly Ser<br>1              5                    10                    15<br>Ser Leu Arg Leu Ser Cys Ala Ala Ser Gly Phe Thr Phe Ser Tyr Ser<br>           20                    25                    30<br>Trp Met Asn Trp Val Arg Gln Ala Pro Gly Lys Gly Leu Glu Trp Met<br>           35                    40                    45<br>Gly Arg Ile Phe Pro Gly Asp Gly Asp Thr Asp Tyr Asn Gly Lys Phe<br>           50                    55                    60<br>Lys Gly Arg Val Thr Ile Thr Ala Asp Lys Ser Thr Ser Thr Ala Tyr<br>65                       70                    75                    80<br>Met Glu Leu Ser Ser Leu Arg Ser Glu Asp Thr Ala Val Tyr Tyr Cys<br>                85                    90                    95<br>Ala Arg Asn Val Phe Asp Gly Tyr Trp Leu Val Tyr Trp Gly Gln Gly<br>           100                    105                    110<br>Thr Leu Val Thr Val Ser Ser<br>           115 | 52 |
| VH of humanized B-Ly1 antibody (B-HL16) | Glu Val Gln Leu Val Glu Ser Gly Gly Gly Leu Val Lys Pro Gly Gly<br>1              5                    10                    15<br>Ser Leu Arg Val Ser Cys Ala Ala Ser Gly Phe Thr Phe Ser Tyr Ser<br>           20                    25                    30 | 53 |

| NAME | SEQUENCE | SEQ ID NO |
|---|---|---|
| | Trp Met Asn Trp Val Arg Gln Ala Pro Gly Lys Gly Leu Glu Trp Met<br>         35                   40                 45<br>Gly Arg Ile Phe Pro Gly Asp Gly Asp Thr Asp Tyr Asn Gly Lys Phe<br>50                 55                 60<br>Lys Gly Arg Val Thr Ile Thr Ala Asp Lys Ser Thr Ser Thr Ala Tyr<br>65                 70                 75               80<br>Met Glu Leu Ser Ser Leu Arg Ser Glu Asp Thr Ala Val Tyr Tyr Cys<br>               85                 90               95<br>Ala Arg Asn Val Phe Asp Gly Tyr Trp Leu Val Tyr Trp Gly Gln Gly<br>            100                105              110<br>Thr Leu Val Thr Val Ser Ser<br>            115 | |
| VH of humanized B-Ly1 antibody (B-HL17) | Glu Val Gln Leu Val Glu Ser Gly Gly Gly Leu Val Lys Pro Gly Gly<br>1                 5                 10               15<br>Ser Leu Arg Leu Ser Cys Ala Ala Ser Gly Phe Thr Phe Ser Tyr Ser<br>               20                 25               30<br>Trp Met Asn Trp Val Arg Gln Ala Pro Gly Lys Gly Leu Glu Trp Met<br>               35                 40               45<br>Gly Arg Ile Phe Pro Gly Asp Gly Asp Thr Asp Tyr Asn Gly Lys Phe<br>50                 55                 60<br>Lys Gly Arg Val Thr Ile Thr Ala Asp Lys Ser Thr Ser Thr Ala Tyr<br>65                 70                 75               80<br>Met Glu Leu Ser Ser Leu Arg Ser Glu Asp Thr Ala Val Tyr Tyr Cys<br>               85                 90               95<br>Ala Arg Asn Val Phe Asp Gly Tyr Trp Leu Val Tyr Trp Gly Gln Gly<br>            100                105              110<br>Thr Leu Val Thr Val Ser Ser<br>            115 | 54 |
| VL of humanized B-Ly1 antibody (B-KVI) | Asp Ile Val Met Thr Gln Thr Pro Leu Ser Leu Pro Val Thr Pro Gly<br>1                 5                 10               15<br>Glu Pro Ala Ser Ile Ser Cys Arg Ser Ser Lys Ser Leu Leu His Ser<br>               20                 25               30<br>Asn Gly Ile Thr Tyr Leu Tyr Trp Tyr Leu Gln Lys Pro Gly Gln Ser<br>               35                 40               45<br>Pro Gln Leu Leu Ile Tyr Gln Met Ser Asn Leu Val Ser Gly Val Pro<br>50                 55                 60<br>Asp Arg Phe Ser Gly Ser Gly Ser Gly Thr Asp Phe Thr Leu Lys Ile<br>65                 70                 75               80<br>Ser Arg Val Glu Ala Glu Asp Val Gly Val Tyr Tyr Cys Ala Gln Asn<br>               85                 90               95<br>Leu Glu Leu Pro Tyr Thr Phe Gly Gly Gly Thr Lys Val Glu Ile Lys<br>            100                105              110<br>Arg Thr Val<br>            115 | 55 |

What is claimed is:

1. A method of treating diffuse large B-cell lymphoma (DLBCL) in an individual, comprising administering to the individual an effective amount of (a) an immunoconjugate comprising an anti-CD79b antibody linked to monomethyl auristatin E (MMAE), (b) obinutuzumab, and (c) a BCL2 inhibitor or a pharmaceutically acceptable salt thereof, wherein the BCL2 inhibitor is venetoclax; and wherein the anti-CD79b antibody comprises: a hypervariable region-H1 (HVR-H1) comprising the amino acid sequence of SEQ ID NO: 21, an HVR-H2 comprising the amino acid sequence of SEQ ID NO: 22, an HVR-H3 comprising the amino acid sequence of SEQ ID NO: 23, a hypervariable region-L1 (HVR-L1) comprising the amino acid sequence of SEQ ID NO: 24, an HVR-L2 comprising the amino acid sequence of SEQ ID NO: 25, and an HVR-L3 comprising the amino acid sequence of SEQ ID NO: 26.

2. The method of claim 1, wherein the immunoconjugate is polatuzumab vedotin.

3. The method of claim 1, wherein the anti-CD79b antibody comprises (i) a heavy chain variable domain comprising the amino acid sequence of SEQ ID NO: 19, and (ii) a light chain variable domain comprising the amino acid sequence of SEQ ID NO: 20.

4. The method of claim 1, wherein the anti-CD79b antibody comprises:
(i) a heavy chain comprising the amino acid sequence of SEQ ID NO: 36, and a light chain comprising the amino acid sequence of SEQ ID NO: 35;
(ii) a heavy chain comprising the amino acid sequence of SEQ ID NO: 37, and a light chain comprising the amino acid sequence of SEQ ID NO: 35; or
(iii) a heavy chain comprising the amino acid sequence of SEQ ID NO: 36, and a light chain comprising the amino acid sequence of SEQ ID NO: 38.

5. The method of claim 1, wherein the anti-CD79b antibody comprises a heavy chain comprising the amino acid sequence of SEQ ID NO: 36, and a light chain comprising the amino acid sequence of SEQ ID NO: 35.

6. The method of claim 1, wherein the immunoconjugate comprises the formula Ab-(L-D)p, wherein:
(a) Ab is the anti-CD79b antibody;
(b) L is a linker;
(c) D is MMAE; and
(d) p is between 1 and 8.

7. The method of claim 6, wherein the linker comprises (i) a val-cit dipeptide; (ii) a Phe-homoLys dipeptide; or (iii) hydrazine.

8. The method of claim 1, wherein the immunoconjugate comprises the formula

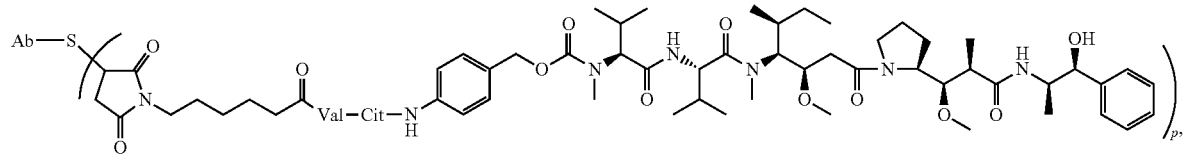

wherein Ab is the anti-CD79b antibody, Val is valine, Cit is citrulline, and p is between 1 and 8.

9. The method of claim 8, wherein the immunoconjugate is administered to the individual at a dose of about 1.4 mg/kg or about 1.8 mg/kg.

10. The method of claim 9, wherein the immunoconjugate is administered to the individual at a dose of about 1.8 mg/kg.

11. The method of claim 1, wherein obinutuzumab is administered to the individual at a dose of about 1000 mg.

12. The method of claim 1, wherein the DLBCL is relapsed or refractory DLBCL (RR DLBCL), wherein the immunoconjugate is polatuzumab vedotin, wherein polatuzumab vedotin, obinutuzumab, and venetoclax are administered during an induction phase comprising six 21-day cycles, and wherein
(i) polatuzumab vedotin is administered intravenously on Day 1 of the first 21-day cycle at a dose of about 1.4 mg/kg or about 1.8 mg/kg, venetoclax is administered orally at a dose of 400 mg, 600 mg, or 800 mg once daily on Days 1-21 of the first 21-day cycle, and obinutuzumab is administered intravenously at a dose of about 1000 mg on each of Days 1, 8, and 15 of the first 21-day cycle, and
(ii) polatuzumab vedotin is administered intravenously at a dose of about 1.4 mg/kg or about 1.8 mg/kg on Day 1 of each of the second, third, fourth, fifth, and sixth 21-day cycles, venetoclax is administered orally at a dose of 400 mg, 600 mg, or 800 mg once daily on Days 1-21 of each of the second, third, fourth, fifth, and sixth 21-day cycles, and obinutuzumab is administered intravenously at a dose of about 1000 mg on Day 1 of each of the second, third, fourth, fifth, and sixth 21-day cycles.

13. The method of claim 12, wherein
(i) venetoclax is administered prior to obinutuzumab and obinutuzumab is administered prior to polatuzumab vedotin on Day 1 of the first 21-day cycle, and venetoclax is administered prior to obinutuzumab on Days 8 and 15 of the first 21-day cycle; and
(ii) venetoclax is administered prior to obinutuzumab and obinutuzumab is administered prior to polatuzumab vedotin on Day 1 of each of the second, third, fourth, fifth, and sixth 21-day cycles.

14. The method of claim 1, wherein the method is for treating RR DLBCL.

15. The method of claim 12, wherein venetoclax and obinutuzumab are further administered during a consolidation phase after the sixth 21-day cycle of the induction phase, wherein venetoclax is administered orally at a dose of 400 mg, 600 mg, or 800 mg once per day for 8 months during the consolidation phase, and wherein obinutuzumab is administered intravenously at a dose of about 1000 mg once every two months for 8 months during the consolidation phase.

16. The method of claim 15, wherein obinutuzumab is administered during the consolidation phase starting on Day 1 of the second month (Month 2) after the sixth 21-day cycle of the induction phase.

17. The method of claim 16, wherein venetoclax is administered prior to obinutuzumab on Day 1 of each of Month 2, 4, 6, and 8 during the consolidation phase.

18. The method of claim 12, wherein polatuzumab vedotin is administered intravenously on Day 1 of the first 21-day cycle at a dose of about 1.8 mg/kg, and polatuzumab vedotin is administered intravenously at a dose of about 1.8 mg/kg on Day 1 of each of the second, third, fourth, fifth, and sixth 21-day cycles.

* * * * *

SEQUENCE LISTING

<160> NUMBER OF SEQ ID NOS: 55

<210> SEQ ID NO 1
<211> LENGTH: 179
<212> TYPE: PRT
<213> ORGANISM: Homo sapiens

<400> SEQUENCE: 1

Arg Phe Ile Ala Arg Lys Arg Gly Phe Thr Val Lys Met His Cys Tyr
1               5                   10                  15

Met Asn Ser Ala Ser Gly Asn Val Ser Trp Leu Trp Lys Gln Glu Met
            20                  25                  30

Asp Glu Asn Pro Gln Gln Leu Lys Leu Glu Lys Gly Arg Met Glu Glu
        35                  40                  45

Ser Gln Asn Glu Ser Leu Ala Thr Leu Thr Ile Gln Gly Ile Arg Phe
    50                  55                  60

Glu Asp Asn Gly Ile Tyr Phe Cys Gln Gln Lys Cys Asn Asn Thr Ser
65                  70                  75                  80

```
Glu Val Tyr Gln Gly Cys Gly Thr Glu Leu Arg Val Met Gly Phe Ser
            85                  90                  95

Thr Leu Ala Gln Leu Lys Gln Arg Asn Thr Leu Lys Asp Gly Ile Ile
        100                 105                 110

Met Ile Gln Thr Leu Leu Ile Ile Leu Phe Ile Ile Val Pro Ile Phe
        115                 120                 125

Leu Leu Leu Asp Lys Asp Ser Lys Ala Gly Met Glu Glu Asp His
        130                 135                 140

Thr Tyr Glu Gly Leu Asp Ile Asp Gln Thr Ala Thr Tyr Glu Asp Ile
145                 150                 155                 160

Val Thr Leu Arg Thr Gly Glu Val Lys Trp Ser Val Gly Glu His Pro
                165                 170                 175

Gly Gln Glu

<210> SEQ ID NO 2
<211> LENGTH: 201
<212> TYPE: PRT
<213> ORGANISM: Homo sapiens

<400> SEQUENCE: 2

Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45

Leu Trp Lys Gln Glu Met Asp Glu Asn Pro Gln Gln Leu Lys Leu Glu
    50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
                85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Gly Ile Ile Met Ile Gln Thr Leu Leu Ile Ile Leu Phe
    130                 135                 140

Ile Ile Val Pro Ile Phe Leu Leu Leu Asp Lys Asp Ser Lys Ala
145                 150                 155                 160

Gly Met Glu Glu Asp His Thr Tyr Glu Gly Leu Asp Ile Asp Gln Thr
                165                 170                 175

Ala Thr Tyr Glu Asp Ile Val Thr Leu Arg Thr Gly Glu Val Lys Trp
            180                 185                 190

Ser Val Gly Glu His Pro Gly Gln Glu
        195                 200

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Pro Glu Leu Val Lys Pro Gly Ala Ser Val Lys Ile Ser Cys Lys
```

```
                 1               5                  10                 15
Ala Ser Gly Tyr Ala Phe Ser Tyr Ser Trp Met Asn Trp Val Lys Leu
                20                  25                 30

Arg Pro Gly Gln Gly Leu Glu Trp Ile Gly Arg Ile Phe Pro Gly Asp
                35                  40                 45

Gly Asp Thr Asp Tyr Asn Gly Lys Phe Lys Gly Lys Ala Thr Leu Thr
        50                  55                 60

Ala Asp Lys Ser Ser Asn Thr Ala Tyr Met Gln Leu Thr Ser Leu Thr
 65                 70                  75                 80

Ser Val Asp Ser Ala Val Tyr Leu Cys Ala Arg Asn Val Phe Asp Gly
                    85                  90                 95

Tyr Trp Leu Val Tyr Trp Gly Gln Gly Thr Leu Val Thr Val Ser Ala
                100                 105                110
```

<210> SEQ ID NO 4
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
                20                  25                  30

Gln Lys Pro Gly Gln Ser Pro Gln Leu Leu Ile Tyr Gln Met Ser Asn
                35                  40                  45

Leu Val Ser Gly Val Pro Asp Arg Phe Ser Ser Gly Ser Gly Thr
        50                  55                  60

Asp Phe Thr Leu Arg Ile Ser Arg Val Glu Ala Glu Asp Val Gly Val
 65                 70                  75                  80

Tyr Tyr Cys Ala Gln Asn Leu Glu Leu Pro Tyr Thr Phe Gly Gly Gly
                    85                  90                  95

Thr Lys Leu Glu Ile Lys Arg
                100
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Tyr Ala Phe Ser Tyr
1               5
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Phe Pro Gly Asp Gly Asp Thr Asp
1               5
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Val Phe Asp Gly Tyr Trp Leu Val Tyr
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Ser Lys Ser Leu Leu His Ser Asn Gly Ile Thr Tyr Leu Tyr
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Met Ser Asn Leu Val Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gln Asn Leu Glu Leu Pro Tyr Thr
1               5

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Arg Thr Val
        115

<210> SEQ ID NO 13
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 14
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
```

20                  25                  30
Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 17
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
    435                 440                 445

<210> SEQ ID NO 18
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125
```

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

```
Ser Leu Gln Pro Glu Asp Phe Ala Thr Tyr Tyr Cys Gln Gln Ser Asn
            85                   90                  95

Glu Asp Pro Leu Thr Phe Gly Gln Gly Thr Lys Val Glu Ile Lys Arg
           100                 105                 110

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Ser Ser Tyr Trp Ile Glu
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Glu Ile Leu Pro Gly Gly Gly Asp Thr Asn Tyr Asn Glu Ile Phe
1               5                   10                  15

Lys Gly

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Arg Arg Val Pro Ile Arg Leu Asp Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ala Ser Gln Ser Val Asp Tyr Glu Gly Asp Ser Phe Leu Asn
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ser Asn Leu Glu Ser
1               5
```

```
<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Ser Asn Glu Asp Pro Leu Thr
1               5

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Val Arg Gln Ala Pro Gly Lys Gly Leu Glu Trp Ile
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Arg Ala Thr Phe Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Gly Gln Gly Thr Leu Val Thr Val Ser Ser
1               5                   10

<210> SEQ ID NO 31
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Tyr Gln Gln Lys Pro Gly Lys Ala Pro Lys Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Gly Gln Gly Thr Lys Val Glu Ile Lys Arg
1               5                   10

<210> SEQ ID NO 35
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45
```

```
Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 36
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Tyr
             20                  25                  30

Trp Ile Glu Trp Val Arg Gln Ala Pro Gly Lys Gly Leu Glu Trp Ile
         35                  40                  45

Gly Glu Ile Leu Pro Gly Gly Gly Asp Thr Asn Tyr Asn Glu Ile Phe
 50                  55                  60

Lys Gly Arg Ala Thr Phe Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 37
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu

```
            100                 105                 110
Val Thr Val Ser Ser Cys Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 38
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Leu Thr Gln Ser Pro Ser Ser Leu Ser Ala Ser Val Gly
1               5                   10                  15
```

Asp Arg Val Thr Ile Thr Cys Lys Ala Ser Gln Ser Val Asp Tyr Glu
             20                  25                  30

Gly Asp Ser Phe Leu Asn Trp Tyr Gln Gln Lys Pro Gly Lys Ala Pro
         35                  40                  45

Lys Leu Leu Ile Tyr Ala Ala Ser Asn Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Cys Thr Lys Ser Phe Asn Arg Gly Glu Cys
    210                 215

<210> SEQ ID NO 39
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

-continued

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Cys
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
```

```
            65                  70                  75                  80
Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asn Val Phe Asp Gly Tyr Trp Leu Val Tyr Trp Gly Gln Gly
            100                 105                 110

Thr Leu Val Thr Val Ser Ser
```

115

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

```
Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
50                      55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
                20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
50                      55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
                20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
50                      55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Lys Pro Gly Ser
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 55
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115